(12) United States Patent
Athey et al.

(10) Patent No.: US 12,176,087 B2
(45) Date of Patent: *Dec. 24, 2024

(54) PHARMACOGENOMIC DECISION SUPPORT FOR MODULATORS OF THE NMDA, GLYCINE, AND AMPA RECEPTORS

(71) Applicant: THE REGENT OF THE UNIVERSITY OF MICHIGAN, Ann Arbor, MI (US)

(72) Inventors: Brian D. Athey, Ann Arbor, MI (US); Alex Ade, Ann Arbor, MI (US); Gerald A. Higgins, Ann Arbor, MI (US); Alexandr Kalinin, Ann Arbor, MI (US); Narathip Reamaroon, Ann Arbor, MI (US); James S. Burns, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1158 days.

This patent is subject to a terminal disclaimer.

(21) Appl. No.: 16/749,737

(22) Filed: Jan. 22, 2020

(65) Prior Publication Data

US 2020/0234810 A1 Jul. 23, 2020

Related U.S. Application Data

(60) Provisional application No. 62/795,705, filed on Jan. 23, 2019, provisional application No. 62/795,710, filed on Jan. 23, 2019.

(51) Int. Cl.
*G16H 20/10* (2018.01)
*G16B 5/00* (2019.01)
(Continued)

(52) U.S. Cl.
CPC .............. *G16H 20/10* (2018.01); *G16B 5/00* (2019.02); *G16B 5/10* (2019.02); *G16B 30/00* (2019.02);
(Continued)

(58) Field of Classification Search
CPC .......... G16B 5/00; G16H 50/20; G16H 50/50
See application file for complete search history.

(56) References Cited

U.S. PATENT DOCUMENTS 10,098,854 B2 10/2018 Drevets et al.
10,249,389 B2 4/2019 Athey et al.
(Continued)

FOREIGN PATENT DOCUMENTS

JP 2012524124 A 10/2012
JP 2014522530 A 9/2014
(Continued)

OTHER PUBLICATIONS

Vialou V, Feng J, Robison AJ, Nestler EJ. Epigenetic mechanisms of depression and antidepressant action. Annu Rev Pharmacol Toxicol. 2013;53:59-87. doi: 10.1146/annurev-pharmtox-010611-134540. Epub Sep. 27, 2012. PMID: 23020296; PMCID: PMC3711377. (Year: 2013).*
(Continued)

*Primary Examiner* — Karlheinz R. Skowronek
*Assistant Examiner* — Emilie A Neulen
(74) *Attorney, Agent, or Firm* — MARSHALL, GERSTEIN & BORUN LLP

(57) ABSTRACT

Methods for identifying patients diagnosed with treatment resistant or refractory depression, pain or other clinical indications who are eligible to receive N-methyl-D-aspartate receptor antagonist, glycine receptor beta (GLRB) modulator, or α-amino-3-hydroxy-5-methyl-4-isoxazolepropionic acid receptor (AMPAR)-based therapies to include deter-
(Continued)

mining the appropriate medication, an optimal dose for each patient, and determining which patients are not eligible to receive the therapy. The pharmacogenomic clinical decision support assays include targeted single nucleotide polymorphisms and clinical values or a combination of targeted single nucleotide polymorphisms, targeted ketamine-specific expansion and contraction of topologically associated domains, and clinical values. The methods described herein allow for a more effective determination of which patients will experience drug efficacy and which patients will experience adverse drug events. The methods provide personalized patient recommendations for dose, the frequency of medication administration, and recommendations on drug choice.

11 Claims, 31 Drawing Sheets

(51) Int. Cl.
    *G16B 5/10*     (2019.01)
    *G16B 30/00*     (2019.01)
    *G16B 40/00*     (2019.01)
    *G16B 45/00*     (2019.01)
    *G16B 50/10*     (2019.01)
    *G16H 50/20*     (2018.01)
    *G16H 50/50*     (2018.01)

(52) U.S. Cl.
    CPC ............. *G16B 40/00* (2019.02); *G16B 45/00* (2019.02); *G16B 50/10* (2019.02); *G16H 50/20* (2018.01); *G16H 50/50* (2018.01)

(56) References Cited

U.S. PATENT DOCUMENTS

| | | | |
|---|---|---|---|
| 2005/0048666 A1* | 3/2005 | Larson | G01N 33/946 422/400 |
| 2012/0041778 A1 | 2/2012 | Kraft | |
| 2014/0274764 A1* | 9/2014 | Zhu | C12Q 1/6883 506/9 |
| 2018/0330824 A1 | 11/2018 | Athey et al. | |

FOREIGN PATENT DOCUMENTS

| | | |
|---|---|---|
| JP | 2015520375 A | 7/2015 |
| JP | 2015522565 A | 8/2015 |
| JP | 2016521987 A | 7/2016 |
| JP | 2016529903 A | 9/2016 |
| WO | WO-02/055995 A2 | 7/2002 |
| WO | WO-2010/123898 A1 | 10/2010 |
| WO | WO-2012/168481 A1 | 12/2012 |
| WO | WO-2013/176694 A1 | 11/2013 |
| WO | WO-2013186399 A1 | 12/2013 |
| WO | WO-2014/202541 A1 | 12/2014 |
| WO | WO-2015/031808 A2 | 3/2015 |

OTHER PUBLICATIONS

Tanaka et al., "Pharmacogenomics of Cardiovascular Pharmacology: Pharmacogenomic Network of Cardiovascular Disease Models", Journal of Pharmacological Sciences, vol. 107, Issue 1, 2008, pp. 8-14, https://doi.org/10.1254/jphs.08R03FM. (Year: 2008).*
Licinio et al., Pharmacogenomics of antidepressant treatment effects, Dialogues Clin. Neurosci., 13(1):63-71 (2011).
International Application No. PCT/US2020/014536, International Search Report and Written Opinion, dated May 12, 2020.
International Application No. PCT/US2020/014549, International Search Report and Written Opinion, dated May 11, 2020.
International Application No. PCT/US2020/014536, International Preliminary Report on Patentability (Chapter II), dated Apr. 26, 2021.
Way et al., Implicating candidate genes at GWAS signals by leveraging topologically associating domains, Eur. J. Hum. Genet., 25(11):1286-9 (Nov. 2017).
Turner et al., Parsing interindividual drug variability: an emerging role for systems pharmacology, Wiley Interdiscip. Rev. Syst. Biol. Med., 7(4):221-41 (2015).
Higgins et al., The epigenome, 4D nucleome and next-generation neuropsychiatric pharmacogenomics, Pharmacogenomics, 16(14):1649-69 (2015).
Tang et al., CTCF-Mediated Human 3D Genome Architecture Reveals Chromatin Topology for Transcription, Cell, 163(7):1611-27 (2015).
Glusman et al., Mapping genetic variations to three-dimensional protein structures to enhance variant interpretation: a proposed framework, Genome Med., 9(1):113 (2017), 10 pages.
Reiling et al., New Pharmacogenomics Research Network: An Open Community Catalyzing Research and Translation in Precision Medicine, Clin. Pharmacol. Ther., 102(6):897-902 (2017).
Hansen et al., Generating genome-scale candidate gene lists for pharmacogenomics, Clin. Pharm. & Ther., 86(2):183-9 (2009).
Jayavelu et al., Iterative sub-network component analysis enables reconstruction of large scale genetic networks, BMC Bioinformatics, 16:366 (2015), 13 pages.
Lu et al., 3DSNP: a database for linking human noncoding SNPs to their three-dimensional interacting genes, Nucleic Acids Res., 45(d1):D643-D649 (2017).
Cirillo et al., A review of pathway-based analysis tools that visualize genetic variants, Frontiers in Genetics, 8:174 (2017), 11 pages.
Niciu et al., Glutamate receptor antagonists as fast-acting therapeutic alternatives for the treatment of depression: ketamine and other compounds. *Annual review of pharmacology and toxicology* 54, 119-139 (2014).
Zanos et al., Ketamine and Ketamine Metabolite Pharmacology: Insights into Therapeutic Mechanisms. *Pharmacological reviews* 70, 621-660 (2018).
Guo et al., Exploratory genome-wide association analysis of response to ketamine and a polygenic analysis of response to scopolamine in depression. *Translational psychiatry* 8, 280 (2018), 8 pages.
Duman et al., Signaling pathways underlying the rapid antidepressant actions of ketamine. *Neuropharmacology* 62, 35-41 (2012).
Higgins et al., Epigenomic mapping and effect sizes of noncoding variants associated with psychotropic drug response. *Pharmacogenomics* 16, 1565-1583 (2015).
Higgins et al., A glutamatergic network mediates lithium response in bipolar disorder as defined by epigenome pathway analysis. *Pharmacogenomics* 16, 1547-1563 (2015).
Kalinin et al., Deep learning in pharmacogenomics: from gene regulation to patient stratification. *Pharmacogenomics* 19, 629-650 (2018).
U.S. Appl. No. 16/749,694, filed Jan. 22, 2020.
Griebel et al., Neuropeptide receptor ligands as drugs for psychiatric diseases: the end of the beginning?, Nat. Rev. Drug Discov., 11(6):462-78 (2012).
Sulman et al., Molecular predictors of outcome and response to bevacizumab (BEV) based on analysis of RTOG 0825, a phase III trial comparing chemoradiation (CRT) with and without BEV in patients with newly diagnosed gliobastoma (GBM), J. Clin. Oncol., 31(18 Suppl) (Jun. 2013). [abstract].
Chiu et al., Application of the Cockcroft-Gault method to estimate lithium dosage requirement, Psychiatry and Clinical Neurosciences, 61.3:269-74 (2007).
Higgins et al., Network reconstruction reveals that valproic acid activates neurogenic transcriptional programs in adult brain following traumatic injury, Pharm. Res., 34:1658-72 (2017).
Kantae et al., Integration of pharmacometabolomics with pharmacokinetics and pharmacodynamics: towards personalized drug therapy, Metabolomics, 13:1-11 (2017).

(56) References Cited

OTHER PUBLICATIONS

Lee et al., DeSigN: connecting gene expression with therapeutics for drug repurposing and development, BMC Genomics, 18.1:1-11 (2017).

* cited by examiner

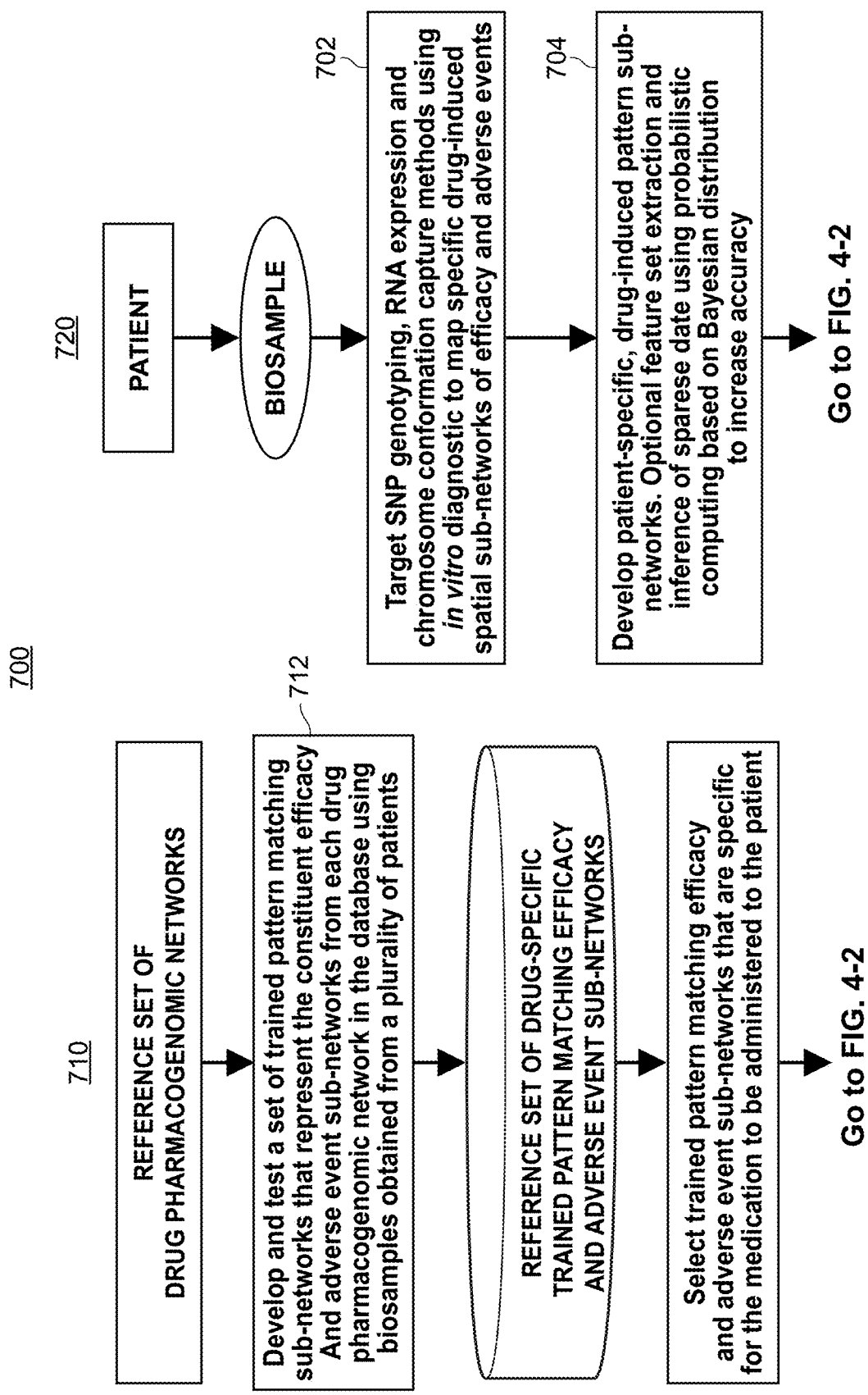

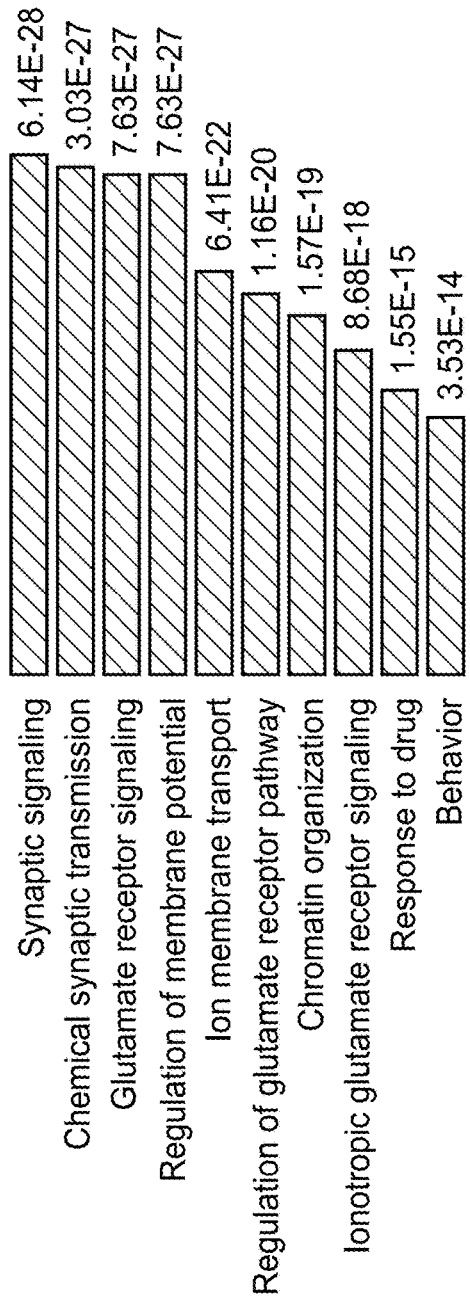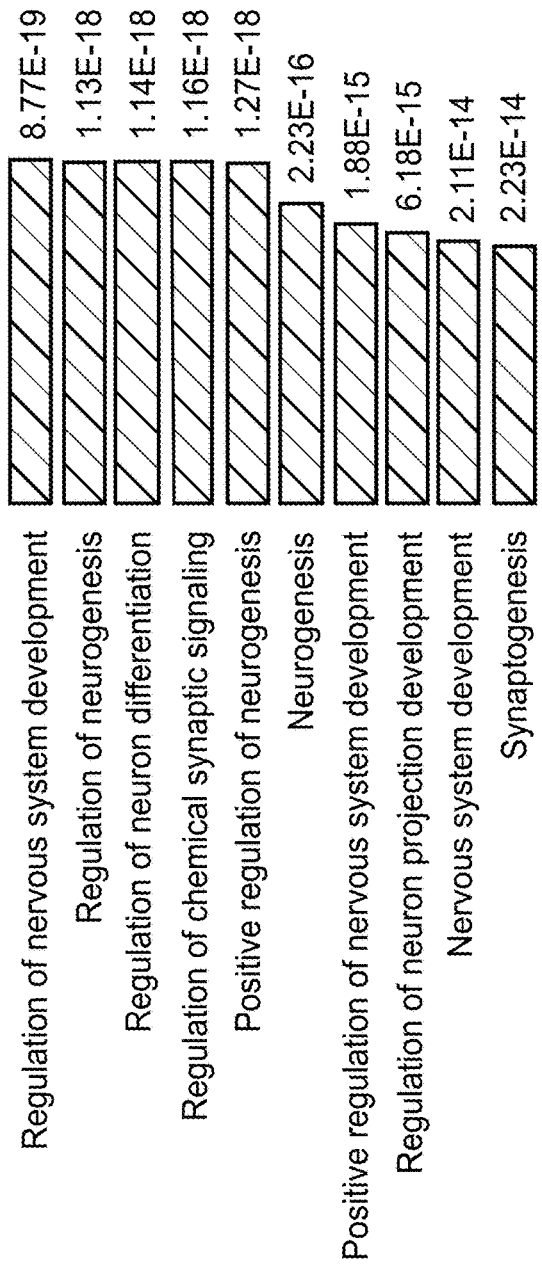
FIG. 13

| Symbol | Entrez Gene Name |
|---|---|
| ARC | activity regulated cytoskeleton associated protein |
| ASCL1 | achaete-scute family bHLH transcription factor 1 |
| BDNF | brain derived neurotrophic factor |
| BDNF-AS | BDNF antisense RNA |
| CAMK2A | calcium/calmodulin dependent protein kinase II alpha |
| CDKN1A | cyclin dependent kinase inhibitor 1A |
| CREM | cAMP responsive element modulator |
| CUX2 | cut like homeobox 2 |
| DCC | DCC netrin 1 receptor |
| DRD2 | dopamine receptor D2 |
| EEF2K | eukaryotic elongation factor 2 kinase |
| FMR1 | fragile X mental retardation 1 |
| GDAP1L1 | ganglioside induced differentiation associated protein 1 like 1 |
| GRM5 | glutamate metabotropic receptor 5 |
| HOMER1 | homer scaffold protein 1 |
| HTR1B | 5-hydroxytryptamine receptor 1B |
| HTR2A | 5-hydroxytryptamine receptor 2A |
| KLF6 | Kruppel like factor 6 |
| LIN7C | lin-7 homolog C, crumbs cell polarity complex component |
| LOC105379109 | |
| MEF2D | myocyte enhancer factor 2D |
| MYO6 | myosin VI |
| MYT1L | myelin transcription factor 1 like |
| NEUROD1 | neuronal differentiation 1 |
| NEUROD2 | neuronal differentiation 2 |
| NHLH2 | nescient helix-loop-helix 2 |
| NMB | neuromedin B |
| NSMF | NMDA receptor synaptonuclear signaling and neuronal migration factor |
| NTRK2 | neurotrophic receptor tyrosine kinase 2 |
| PTEN | phosphatase and tensin homolog |
| PTGS2 | prostaglandin-endoperoxide synthase 2 |
| RAC1 | Rac family small GTPase 1 |
| RASGRF2 | Ras protein specific guanine nucleotide releasing factor 2 |
| RHOA | ras homolog family member A |
| ROBO2 | roundabout guidance receptor 2 |
| RP11_360A181 | |
| SEMA3A | semaphorin 3A |
| SHANK1 | SH3 and multiple ankyrin repeat domains 1 |
| SHANK2 | SH3 and multiple ankyrin repeat domains 2 |
| SHANK3 | SH3 and multiple ankyrin repeat domains 3 |
| SLC22A15 | solute carrier family 22 member 15 |
| SLC6A2 | solute carrier family 6 member 2 |
| SLIT1 | slit guidance ligand 1 |
| SLIT2 | slit guidance ligand 2 |
| SNAP25 | synaptosome associated protein 25 |
| SYN1 | synapsin I |
| SYN2 | synapsin II |
| SYT3 | synaptotagmin 3 |
| TBR1 | T-box, brain 1 |
| TCF4 | transcription factor 4 |

FIG. 15

| Symbol | Entrez Gene Name |
|---|---|
| ACHE | acetylcholinesterase (Cartwright blood group) |
| ATF7IP | activating transcription factor 7 interacting protein |
| ATF7IP2 | activating transcription factor 7 interacting protein 2 |
| ATP1A1 | ATPase Na+/K+ transporting subunit alpha 1 |
| BORCS7 | BLOC-1 related complex subunit 7 |
| BRD4 | bromodomain containing 4 |
| CACNA1C | calcium voltage-gated channel subunit alpha1 C |
| CACNB1 | calcium voltage-gated channel auxiliary subunit beta 1 |
| CACNB2 | calcium voltage-gated channel auxiliary subunit beta 2 |
| CACNG2 | calcium voltage-gated channel auxiliary subunit gamma 2 |
| CHRM2 | cholinergic receptor muscarinic 2 |
| CHRNA3 | cholinergic receptor nicotinic alpha 3 subunit |
| CHRNA5 | cholinergic receptor nicotinic alpha 5 subunit |
| CHRNA7 | cholinergic receptor nicotinic alpha 7 subunit |
| CNR1 | cannabinoid receptor 1 |
| DLG3 | discs large MAGUK scaffold protein 3 |
| DLG4 | discs large MAGUK scaffold protein 4 |
| DNMT1 | DNA methyltransferase 1 |
| EHMT1 | euchromatic histone lysine methyltransferase 1 |
| GABRA2 | gamma-aminobutyric acid type A receptor alpha2 subunit |
| GABRA5 | gamma-aminobutyric acid type A receptor alpha5 subunit |
| GAD1 | glutamate decarboxylase 1 |
| GLRA1 | glycine receptor alpha 1 |
| GLRA2 | glycine receptor alpha 2 |
| GLRB | glycine receptor beta |
| GRIA1 | glutamate ionotropic receptor AMPA type subunit 1 |
| GRIA2 | glutamate ionotropic receptor AMPA type subunit 2 |
| GRIA4 | glutamate ionotropic receptor AMPA type subunit 4 |
| GRIN1 | glutamate ionotropic receptor NMDA type subunit 1 |
| GRIN2A | glutamate ionotropic receptor NMDA type subunit 2A |
| GRIN2B | glutamate ionotropic receptor NMDA type subunit 2B |
| GRIN2C | glutamate ionotropic receptor NMDA type subunit 2C |
| GRIN2D | glutamate ionotropic receptor NMDA type subunit 2D |
| GRIN3A | glutamate ionotropic receptor NMDA type subunit 3A |
| GRIN3B | glutamate ionotropic receptor NMDA type subunit 3B |
| HCN1 | hyperpolarization activated cyclic nucleotide gated potassium channel 1 |
| HDAC5 | histone deacetylase 5 |
| MBD1 | methyl-CpG binding domain protein 1 |
| MPHOSPH8 | M-phase phosphoprotein 8 |
| NCAM1 | neural cell adhesion molecule 1 |
| NOS1 | nitric oxide synthase 1 |
| NOS2 | nitric oxide synthase 2 |
| NOS3 | nitric oxide synthase 3 |
| NQO1 | NAD(P)H quinone dehydrogenase 1 |
| OPRK1 | opioid receptor kappa 1 |
| OPRM1 | opioid receptor mu 1 |
| ROBO2 | roundabout guidance receptor 2 |
| SETDB1 | SET domain bifurcated histone lysine methyltransferase 1 |
| SHANK2 | SH3 and multiple ankyrin repeat domains 2 |
| SIGMAR1 | sigma non-opioid intracellular receptor 1 |
| SLC6A9 | solute carrier family 6 member 9 |
| TASOR | transcription activation suppressor |
| TOGARAM2 | TOG array regulator of axonemal microtubules 2 |
| TRIM28 | tripartite motif containing 28 |
| ZNF274 | zinc finger protein 274 |

FIG. 16

| Symbol | Entrez Gene Name |
|---|---|
| ANAPC2 | anaphase promoting complex subunit 2 |
| CYP2A6 (includes others) | cytochrome P450 family 2 subfamily A member 6 |
| CYP2B6 | cytochrome P450 family 2 subfamily B member 6 |
| CYP3A4 | cytochrome P450 family 3 subfamily A member 4 |
| DLG4 | discs large MAGUK scaffold protein 4 |
| EEF2K | eukaryotic elongation factor 2 kinase |
| ESR1 | estrogen receptor 1 |
| GRIA1 | glutamate ionotropic receptor AMPA type subunit 1 |
| GRIA4 | glutamate ionotropic receptor AMPA type subunit 4 |
| GRIN1 | glutamate ionotropic receptor NMDA type subunit 1 |
| GRIN2B | glutamate ionotropic receptor NMDA type subunit 2B |
| MYO6 | myosin VI |
| ROBO2 | roundabout guidance receptor 2 |
| SHANK2 | SH3 and multiple ankyrin repeat domains 2 |
| TCERG1 | transcription elongation regulator 1 |

FIG. 17

| Inputs required for the algorithm | Independent predictors of Esketamine dose | $R^2$ after rank and entry in cohort model | $P$-value in cohort |
|---|---|---|---|
| CYP2B6 SNP rs3745274* | +100% | 1 | 25% | <0.0001 |
| Biological sex (Female, pre-menopausal) | -25% | 2 | 34% | <0.0001 |
| CYP2B6 SNP rs3786547* | -22% | 4 | 40% | <0.0001 |
| Clopidogrel (Plavix®) use | -22% | 5 | 45% | <0.0001 |
| CYP2B6 SNP rs11083595* | -19% | 6 | 50% | <0.0001 |
| Height, weight (Body Surface Area, BSA or BMI) | -11% per 0.25m² | 7 | 52% | 0.001 |
| Current smoker | -20% | 8 | 53% | 0.001 |
| Nicotine use other than tobacco | -11% | 9 | 53.4% | 0.001 |
| Suicide attempt(s) and/or family history of suicide (first degree relative) | -17% | 10 | 53.8% | 0.001 |
| Age | -7% per decade | 11 | 54% | 0.002 |
| Family history of alcohol use disorder (first degree relative) | -10% | 12 | 54.4% | 0.002 |
| Ethnicity | -10% (Non-Hispanic white) | 13 | 54.7% | 0.002 |
| Ticlopidine (Ticlid®) use | -20% | 14 | 54.9% | 0.002 |
| Previous psychiatric hospitalization | -15% | 15 | 55% | 0.002 |

FIG. 18A

| Accuracy metric | Pharmacogenomics | Clinical | $P$-value |
|---|---|---|---|
| $R^2$ (SD) | 54% (5%) | 17% (4%) | <0.001 |
| Median (mean) absolute prediction error, mg/day | 1.0 (1.4) | 1.6 (1.9) | <0.001 |

FIG. 18B

| % of TRD patients | Symptoms in rank order (HAMD-17) | Network connectivity predicted by from TMS and neuroimaging | Behavioral traits | Associated clinical values |
|---|---|---|---|---|
| 1 | 23.6% | Anxiety, Anergia, fatigue | • Reduced connectivity in frontoamygdala networks, which regulate fear-related behavior and reappraisal of negative emotional stimuli<br>• Reduced connectivity in anterior cingulate and orbitofrontal areas supporting motivation and incentive-salience evaluation | • Poor impulse control<br>• Desires never satisfied<br>• Highest scores on neuroticism of the different subtypes | 1. Co-diagnosis of generalized anxiety disorder (GAD) and recurrent depression;<br>2. Natural language processing (NLP) of psychiatric notes on "neuroticism";<br>3. HAMD-17 rating – "neuroticism". |
| 2 | 22.7% | Anergia, fatigue, Anhedonia | • Reduced connectivity in anterior cingulate and orbitofrontal areas supporting motivation and incentive-salience evaluation | • Score lower on HAMD and other depression rating scales than other biotypes<br>• Loneliness | 1. NLP of clinical notes or HAMD-17 rating – "loneliness";<br>2. ICD codes for chronic fatigue syndrome, fibromyalgia and neuropathic pain. |
| 3 | 20.0% | Anhedonia, PMR (Psychomotor retardation), PMA (Psychomotor agitation) | • Hyperconnectivity in thalamic and frontostriatal networks with exception of the nucleus accumbens;<br>• Hyperactive subgeniculate anterior cingulate cortex (sgACC);<br>• Hyperactive neurons of lateral orbitofrontal cortex, which supports non-reward / punishment system and substitutes for the Nucleus accumbens-based reward system in these patients | • High impulse control<br>• Introversion<br>• Highest educational attainment and "successful"<br>• Exaggerated focus and rumination on finances, job<br>• Self-deprivation – food, clothes, bathing ("punishing") | 1. Measures of educational attainment based on college degrees, post-graduate education;<br>2. In longitudinal EHR, loss in body weight;<br>3. HAMD-17 rating – "PMR, PMA";<br>4. Failure to respond to the drug mirtazapine in pharmacotherapy regimens. |
| 4 | 33.6% | Anxiety, Anhedonia, Guilt, PMR (Psychomotor retardation), Early insomnia, Middle insomnia, Hypochondria, Suicidal ideation, family history. | • Reduced connectivity in frontoamygdala networks which regulate fear-related behavior and reappraisal of negative emotional stimuli<br>• Hyperconnectivity in thalamic and frontostriatal networks, which support reward processing, adaptive motor control and action initiation | • Poor impulse control<br>• Extroversion<br>• Constant attempts to validate self-worth based on praise from others<br>• Tendency towards bipolar disorder and dysfunctional moods | 1. Co-diagnosis of generalized anxiety disorder (GAD) and recurrent depression;<br>2. Co-diagnosis of bipolar spectrum disorders and/or hypomania;<br>3. NLP or structured data showing "suicidal ideation";<br>4. Lithium-responsive. |

FIG. 19

| Subtype | Selection of ketamine as antidepressant? | Antidepressants, other psychotropic medications and options to which TRD patients should be switched if not ketamine |
|---|---|---|
| 1 | Yes | <ul><li>Fluoxetine</li><li>Lamotrigine</li><li>Lithium</li><li>Valproic acid</li></ul> |
| 2 | Yes | <ul><li>Amitriptyline, if not already proven ineffective in patient or cohort</li><li>Recommend transcranial magnetic stimulation (TMS) with proper anatomical positioning</li><li>Recommend cognitive behavioral therapy</li></ul> |
| 3 | No, based on innate hyperactivity of the subgenicuate cingulate, prefrontal and orbitofrontal cortices. | <ul><li>Amitriptyline, if not already proven ineffective in patient or cohort</li><li>Mirtazapine, if not already proven ineffective in patient or cohort</li><li>Recommend transcranial magnetic stimulation (TMS) with proper anatomical positioning</li></ul> |
| 4 | Yes | <ul><li>Clonazepam</li><li>Escitalopram, if not already proven ineffective in patient or cohort</li><li>Lamotrigine</li><li>Lithium</li><li>Quetiapine</li><li>Sertraline, if not already proven ineffective in patient or cohort</li><li>Valproic acid</li><li>Zolpidem extended release (if not on Quetiapine pharmacotherapy)</li><li>Recommend transcranial magnetic stimulation (TMS) with proper anatomical positioning</li><li>Recommend behavioral dialectical therapy</li></ul> |

FIG. 21

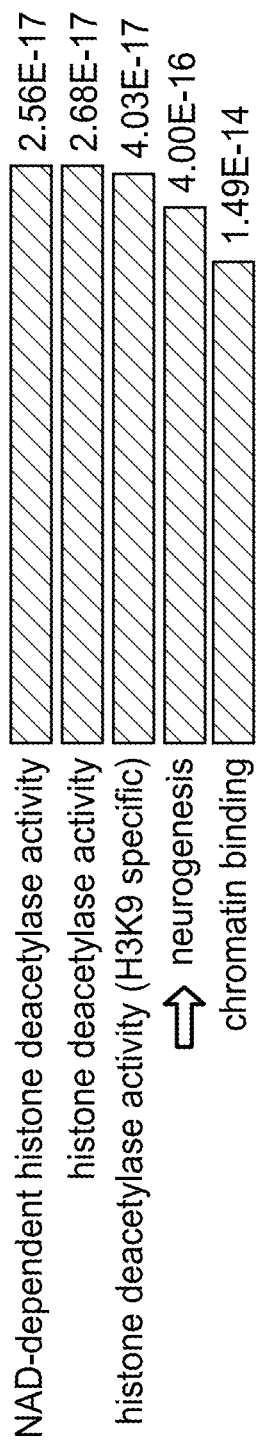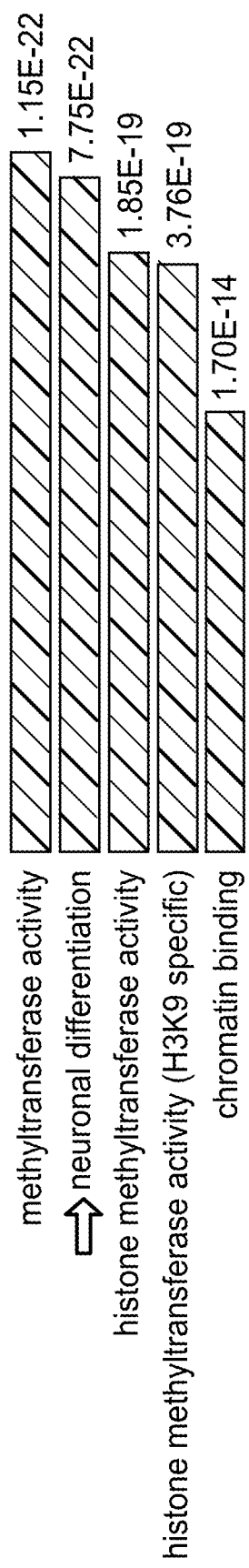
FIG. 23

PHARMACOGENOMIC DECISION SUPPORT FOR MODULATORS OF THE NMDA, GLYCINE, AND AMPA RECEPTORS

CROSS-REFERENCE TO RELATED APPLICATIONS

This application claims priority to and the benefit of the filing date of (1) provisional U.S. Application Serial No. 62/795,705, filed on Jan. 23, 2019, entitled "Methods and Systems to Reconstruct Drug Spatial Networks from Pharmacogenomic Regulatory Interactions and Uses Thereof," and (2) provisional U.S. Application Serial No. 62/795,710, filed on Jan. 23, 2019, entitled "Companion Diagnostic Assays for N-methyl-D-Aspartate Receptor Modulators," the entire disclosures of each of which is hereby expressly incorporated by reference herein.

FIELD OF THE INVENTION

The techniques described herein pertain to pharmacogenomic clinical decision support assays useful for the selection of N-methyl-D-aspartate (NMDA) receptor, glycine receptor, and α-amino-3-hydroxy-5-methyl-4-isoxazolepropionic acid (AMPA) receptor-based therapies for depression (especially treatment-resistant or refractory depression) and other clinical indications including anesthesia and analgesia/pain disorders, neuropsychiatric disorders, and neurological disorders using ketamine and its enantiomers as examples. More specifically, the techniques relate to specific biomarkers, including genetic markers, clinical values, and disease phenotypes derived from a patient to optimize selection of medications that impact these receptor networks and doses for an individual patient.

BACKGROUND

Existing antidepressant medications are not effective for many patients. A new class of antidepressant drugs are being developed that target glutamate receptors in human forebrain. Ketamine (RS-2-chlorophenyl-2-methylamino-cyclohexanone), a glutamate N-methyl-d-aspartate receptor (NMDAR) noncompetitive antagonist, approved by the U.S. Food & Drug Administration (FDA) as an anesthetic, has shown promise as an antidepressant in patients with treatment-resistant depression (TRD). Although the racemic formula may have potent and undesirable psychotomimetic and other side effects depending upon several variables, chemical analogs of ketamine exhibit diminished adverse events. Intravenous and oral formulations have demonstrated efficacy and tolerability in controlled trials and open-label studies across patient populations known to often achieve little to no response from traditional antidepressants that target the serotonin transporter (SLC6A4, also called 5HTT or SERT1), including serotonin-norepinephrine reuptake inhibitors (SNRIs). Evidence suggests that ketamine, its enantiomers, and ketamine analogs exert their mechanism of action primarily through modulation of the NMDA receptor (NMDAR) and downstream receptors in this network in the human brain.

The pharmacodynamic (PD) target for ketamine-like drugs is an NMDAR that consists of GRIN1 and GRIN2 subunits, which binds glutamate and N-methyl-D-aspartate, a binding site for glycine and D-serine encoded by GLRB, as well as sites that bind polyamines, histamine and cations. Antagonists, partial antagonists and receptor modulators such as ketamine and its and other NMDAR and glycine modulators, including phencyclidine, amantadine, dextromethorphan, tiletamine, riluzole, methoxetamine, methoxphenidine and memantine, block inward $Ca^{+2}$ influx, preventing postsynaptic depolarization. Neuroimaging studies have demonstrated that intravenous infusion of ketamine causes a transient surge in glutamate levels observed in prefrontal cortex in concert with a rapid antidepressant effect. It has been shown that following NMDAR blockade, glutamate preferentially binds to the GRIA1, GRIA2 and GRIA4 subunits of the α-amino-3-hydroxy-5-methyl-4-isoxazolepropionic acid (AMPA) receptor. Several NMDAR antagonists and partial antagonists, GLRB modulators and AMPAR agonists are in development for therapy of refractory depression, but exhibit dissociative effects in patients. In addition, NMDAR antagonists, GLRB antagonists and AMPAR modulators, partial antagonists and receptor modulators that act in the same network as this class of drugs that have failed in clinical trials based on safety concerns might be repurposed using the methods of this disclosure to improve their chances of success in clinical trials.

The three-dimensional (3D) architecture of the human regulatory epigenome plays a major role in determining human phenotype. It is now acknowledged that the majority of significant single nucleotide polymorphisms (SNPs) associated with disease risk, drug response, and other human traits found in genome-wide association studies (GWAS) are located within enhancers, promoters and other non-coding regulatory elements. Coupled with recent insights into the organization of the functional 4D Nucleome, an abundance of biomedical "big data" has become accessible in open source and proprietary resources, enabling the reconstruction of drug regulatory pathways in the human genome. New methods are being applied for the mining of regulatory variants from genome-wide association studies (GWAS), phenome-wide association studies (PheWAS), and results from mining electronic health record data and clinical trial data. It is now standard practice in the art that single nucleotide polymorphism (SNP) trait-associations from these data sources are re-evaluated in the context of pathway analysis, and have been found to be significant because they resolve to the same or related biological networks. Combining an abundance of biomedical data coupled with innovative methods for mining biological networks has provided a foundation for the detection of gene variants that may impact variability in drug response, including adverse drug events. This approach promises tremendous advances in specialties such as psychiatry, in which a lack of drug efficacy and an abundance of adverse drug events have proven especially problematic in patient care.

Over half of all Americans will exhibit the symptoms of a psychiatric disorder during their lifetime. The most prevalent lifetime psychiatric disorders are stress and anxiety disorders, mood disorders, including major depressive disorder and bipolar disorder, impulse-control disorders, substance use disorders and schizoaffective disorders. The lifetime prevalence of any psychiatric disorder in the U.S. is 53%, while 28% have two or more lifetime disorders and 18% have three or more, showing that comorbidity of psychiatric disorders is a significant medical challenge. Although some psychiatric disorders, such as bipolar 1 disorder are inherited in families at approximately an 80% penetration rate, others exhibit no obvious heritability. For major depressive disorder (MDD), genetic factors play important roles in the etiology of the disease, as indicated by family, twin, and adoption studies. Twin studies suggest a heritability of 50%, and family studies indicate a twofold to threefold increase in lifetime risk of developing MDD among first-degree relatives. Several socio-demographic variables are significantly related to lifetime risk of psychiatric disorders in studies that controlled for cohort. For example, females (biological sex) have a significantly higher risk than men of anxiety and major depressive disorder, and males (biological sex) have a significantly higher risk than females of impulse-control and substance abuse disorders. Non-Hispanic blacks and Hispanics have a significantly lower risk than non-Hispanic whites of anxiety, mood, and substance abuse disorders, and low education is associated with a high risk of substance abuse disorders. The data shows that many factors, ranging from environmental and sociological factors, biological sex, ethnicity and familial genetics, all contribute to the etiology of psychiatric disease. In addition, the complexity of phenotype within an individual patient or cohort of patients, including comorbidities with other psychiatric disorders and stress-related diseases, necessitates a range of distinct algorithmic classification solutions, including machine learning, as well as multiple statistical analyses, including linear regression, to accurately specify precision therapy beyond what is currently available.

Psychiatric illness has a greater impact on human health than any other disease. For example, major depressive disorder (MDD) causes a greater burden of disability worldwide than any other medical condition including cancer, heart disease, stroke, chronic obstructive pulmonary disease, and HIV/AIDS, yet it remains the most undiagnosed, misdiagnosed and untreated or poorly treated disease known to humankind. In 2013, the U.S. National Institutes of Health (NIH) provided 13 times more funding for research in oncology than for depression—~$5.3 billion versus $415 million. In the U.S. from 2009-2011, adverse events related to prescribed antidepressants amounted to over 25,000 visits to the emergency room on an annual basis, resulting in 30% of all prescription drug-related hospitalizations each year. Patients with major depressive disorder and comorbid medical conditions experience more severe symptoms of depression and lower rates of response and remission with antidepressant treatment compared with patients with no comorbid conditions. Treatment-resistant depression (TRD) constitutes 30-40% of all patients diagnosed with MDD and is defined as "failure to achieve remission after two well-established antidepressant courses known to have been of evidence-based acceptable dose and duration."

Contemporary antidepressant medications are not effective in many patients, and in patients that do respond or remit, weeks to months of pharmacotherapy are required before the alleviation of symptoms is achieved. Consequently, newer and more effective antidepressant medications are being developed. For example, both the racemic mixture of ketamine and the S-enantiomer of ketamine are examples of N-methyl-D-aspartate receptor (NMDAR) partial antagonists that have been approved by the U.S. Food and Drug Administration (FDA) for treatment of TRD. Ketamine elicits a rapid antidepressant response and concomitant elevated levels of glutamate in cortex for approximately 50% of TRD patients as measured by the Montgomery-Asberg Depression Rating Scale (MADRS) total score. Although R, S-ketamine has been used for clinical indications such as chronic pain, peri-operative analgesia and sedation since 1970, adverse drug events (AEs) are common following ketamine treatment, and diversion is limited by restricting use to inpatient and outpatient treatment settings. For example, in the phase III clinical trial of Esketamine for TRD prior to submission to the FDA, almost a quarter of the TRD patients experienced severe dissociative effects, 2 deaths were reported, and an additional 6.9% of TRD patients in the treatment arm experienced severe psychotomimetic effects including delirium, delusion and suicidal ideation, as well as suicide attempts.

One of the challenges in psychiatry is precise matching of pharmacotherapy to accurately address the complex symptomatology of the individual patient. Psychiatric patients exhibit extensive comorbid disorders, and there are few objective biomarkers that can be used as diagnostic criteria to accurately tailor antidepressant, antipsychotic and anti-manic therapy to the patient. Although diagnostic rating scales such as the Hamilton Scale for Depression (HAM-D) exhibit good inter-rater reliability, psychiatric disorders such as depression present as various distinct phenotypes. Non-pharmacological therapies may exhibit improved efficacy in patients with TRD or recurrent depression. For example, repetitive transcranial magnetic stimulation (rTMS) shows promise as a non-medication therapeutic alternative for patients suffering from TRD; however, the best outcomes in TRD occur when rTMS is used as an adjunct to traditional antidepressant pharmacotherapy, as is the case for the antidepressant class of medications that include an NMDAR antagonist or partial antagonist, GLRB modulator, or AMPAR agonist, which can only be provided in a clinical setting to a patient who is already taking another antidepressant medication.

rTMS therapy requires dozens of clinical visits, remission is highly variable among patients with TRD, and rTMS is effective in only about 20-40% of cases, in which remission from depression lasts for as long as 1-2 years. Recent results from rTMS combined with neuroimaging demonstrate specific clustering of depressed patients into 4 distinct phenotypes along axes of anhedonia and anxiety based on differential rTMS array placement. These results provide substantive evidence that it is possible to stratify psychiatric patients by phenotype based on activation of different brain connectivity pathways, networks which exhibit considerable inter-individual variability among patients, and greatly improves the opportunity for precise matching of optimal therapy to the individual patient.

Although rTMS offers promise for patients with TRD, its mechanism of action remained elusive until independent research studies demonstrated that TMS first acts in the subgenual anterior cingulate cortex and significantly increases glutamate levels along with biomarkers of N-methyl-d-aspartate receptor (NMDAR) modulation.

These are remarkable findings, as they demonstrate that the mechanism of rTMS brain activation is virtually indistinguishable from that of ketamine's pharmacotherapeutic mechanism of action. Thus, rTMS and ketamine exhibit similar mechanisms of action to relieve TRD, although about half of all TRD patients do not remit after treatment using either therapeutic option. In addition, both rTMS and ketamine exhibit transient but serious AEs, including dissociation (the presumptive basis of ketamine's analgesic efficacy), psychotomimesis, and neurocognitive impairment. This suggests that it is critically important to match individual patients to one of these therapies or to other antidepressant medications if we can choose which patient will benefit from these treatments and which patient will suffer unnecessarily from serious AEs without adequate antidepressant efficacy.

Recent research combining transcranial magnetic stimulation (TMS) to alleviate depression followed by neuroimaging demonstrated that TRD patients can be unambiguously stratified into 4 subtypes based on their response to placement of the TMS device, with 4 different intrinsic neuroanatomical pathways activated concomitant with distinctly different symptom clusters. These 4 subtypes can now be determined independently, as demonstrated by this disclosure, using a combination of clinical and molecular data, thereby providing an exemplar for other psychiatric disorders and stress-related disorders, in which improved pharmacophenomic decision support will deliver better therapeutic options to the patient. Similarly, NMDAR antagonist therapy may be used as an adjunct to age-related degenerative medical conditions.

SUMMARY

Different methods may be used to accurately determine the precise therapeutic requirements for an individual patient phenotype or cohort of phenotypes. This disclosure describes methods for the configuration of a pharmacophenomic assay for clinical decision support, or a companion diagnostic for a psychotropic medication, which optimizes the fit of a therapeutic intervention to an individual patient or cohort of patients diagnosed with a psychiatric or related disorder, such as treatment-resistant depression, chronic pain, migraine, fibromyalgia, inflammatory disorders and other conditions in which ketamine or one its analogs comprise an effective therapeutic. In the context of this disclosure, the patient's drug response and adverse event phenotype is comprised of multiple sets of variables as described herein, ranging from a patient's intrinsic configuration of a drug's pharmacogenomic network including its mutational profile configuration, to behavioral phenotypes that may be obtained from clinical data.

The methods used for patient stratification in this disclosure use disparate data sources, some of which may be incomplete, require data cleansing and/or curation, or may be non-existent. The different methods as described herein range from those that may accommodate different combinations of limited data to more extensive computational solutions, or which may bridge missing data elements using probabilistic methods.

This disclosure comprises a range of concatenated and distinct methods to provide accurate pharmacophenomic decision support for a patient diagnosed with a psychiatric disorder. Outputs provide quantitative scores for ranking therapeutic interventions including recommendations such as medication selection and dose, transcranial magnetic stimulation, electroconvulsive therapy and behavioral intervention. This disclosure comprises pharmacophenomic methods to classify patients diagnosed with a psychiatric disorder into subtypes for optimization of therapeutic intervention. These methods can be used to configure a diagnostic to recommend the best therapeutic match to an individual patient. In another embodiment, these methods may be used to enhance the selection of patients based on pharmacophenomic stratification prior to a clinical trial. In another embodiment, these methods may be used to configure a companion diagnostic for a psychotropic medication to ensure patient safety during the development, marketing and post-marketing of a pharmaceutical.

In another embodiment, clinical values are obtained from an EHR or similar source, and SNPs in PD and PK genes are obtained from the genotype of a patient, and these are entered as quantitative values in a regression equation (nomogram) for determination of medication dose for a drug such as ketamine for that individual patient. In this embodiment, the therapeutic dose optimum is developed in a step-wise regression model equation containing genetic and clinical values, and the regression model is re-tested and validated using a population of patients to ensure the accuracy of the regression equation's output, as might be judged by a receiver-operator (ROC) curve as area under the curve (AUC).

In another embodiment, clinical values are obtained from an EHR or similar source, and SNPs in PD and PK genes are combined with disease risk SNPs obtained from genome-wide association studies (GWAS) to differentially annotate adverse event and efficacy-specific sub-networks of a drug pharmacogenomic network, such as that of ketamine, to predict whether the patient would benefit from the drug or not, and if so, be determinative of a patient-appropriate dosage.

In another embodiment, clinical values are obtained from an EHR or similar source, and SNPs in PD and PK genes are combined with disease risk SNPs obtained from GWAS and PheWAS to differentially annotate adverse event and efficacy-specific sub-networks of a drug pharmacogenomic network, such as that of ketamine, to predict whether the patient would benefit from the drug or not, and if so, be determinative of a patient-appropriate dosage. In this embodiment, therapeutic drug monitoring through pharmacometabolomics is used to gather more accurate data on pre-existing prescribed and non-prescribed drugs and their metabolites used by the patient, through analysis of a biological sample (blood, cheek swab, urine or other bodily fluid) obtained from a patient or from a cohort of patients.

In yet another embodiment, clinical values are obtained from an EHR or similar source, and SNPs in PD and PK genes are combined with disease risk SNPs obtained from GWAS and PheWAS to differentially annotate adverse event and efficacy-specific sub-networks of a drug pharmacogenomic network, such as that of ketamine, and these data are matched with 1 of 4 phenotypes, which may or may not be derived from rTMS and neuroimaging data), determined using scoring from the Hamilton Depression Rating Scale (HAMD) in the context of an antidepressant drug such as ketamine.

In another embodiment, pharmacophenomic decision support is determined using inputs from a model that includes: (1) molecular profiling of drug-induced sub-networks in a patient or cohort of patients, (2) clinical variables as derived from an electronic health record or equivalent measurements made by a clinician, (3) patient subtyping based on clinical variables and neuroimaging studies, and (4) PD and PK SNPs that stratify patients by drug response. In addition, drug-drug and drug-gene interactions objectively measured using a pharmacometabolomic method can be used to minimize adverse drug events for the individual patient or a cohort of patients.

Another embodiment of this system is configuration of a companion diagnostic that can be used for patient selection for a clinical trial, and during the marketing and post-marketing phases of a drug, such as an antidepressant medication that acts as a NMDAR antagonist, partial antagonist, GLRB modulator and AMPAR agonist.

Another embodiment of this system is to determine and select a therapeutic medication addition to a NMDAR modulator to improve outcome. Another embodiment of the methods and system described herein could be used for the re-evaluation of drugs for clinical trials and for drug re-purposing.

BRIEF DESCRIPTION OF THE DRAWINGS

FIG. 3A illustrates how different laboratory methods may be used to obtain measures from the chromatin spatial interactome in three dimensions and analyze the data as 2 dimensional plots of enhancer-gene promoter interactions. FIG. 3B depicts how a SNP may disrupt a chromatin loop between an enhancer and one of two gene promoters that it regulates within a TAD. This disruption removes the spatial connection between the enhancer and gene promoter 1 resulting in dysregulation of gene 1, resulting in an adverse event in this patient and its cohort in response to administration of the particular drug of interest;

FIGS. 4-1 and 4-2 illustrate a flow diagram and scoring system representing an exemplary method for determining a the proper drug and dosage while avoiding adverse events (AEs) to administer to a patient suffering from depression or other neuropsychiatric illness based on comparing data from the patient's biological sample to a reference drug-specific pharmacogenomic network and the constituent sub-networks for the drug of interest;

FIG. 13 illustrates characteristics of the 2 different ketamine pharmacogenomic sub-networks as determined from a post hoc validation of the ketamine pharmacogenomic network in the human brain. FIG. 13A is gene enrichment for the ketamine pharmacogenomic sub-network in the human brain that mediates efficacy and neuroplasticity. FIG. 13B is gene enrichment for the ketamine pharmacogenomic sub-network in the human brain that mediates glutamate receptor signaling and adverse events in the human brain;

FIG. 15 lists the genes and regulatory RNAs located in the ketamine efficacy and neuroplasticity sub-network;

FIG. 16 lists the genes located in the ketamine glutamate receptor signaling and adverse event sub-network;

FIG. 17 lists the genes located in the ketamine pharmacokinetics and hormonal regulation sub-network;

FIGS. 18A-18B illustrate example values of a linear regression analysis for ketamine dose determination and the accuracy of the ketamine dosing in a validation cohort;

FIG. 19 illustrates definitions of four treatment-resistant depression (TRD) patient subtypes as determined by transcranial magnetic stimulation (TMS) coupled with neuroimaging of resting connectivity networks in human brain;

FIG. 21 illustrates example drug prescribe/do not prescribe recommendations and alternative medication options for each of the four different subtypes of TRD depressed patients;

FIG. 23 illustrates the complementary pharmacogenomic network of valproic acid, FIG. 23A, and the pharmacogenomic network of ketamine, FIG. 23B, showing neurogenesis and neuro-differentiation, respectively.

DETAILED DESCRIPTION

Figure 1A:
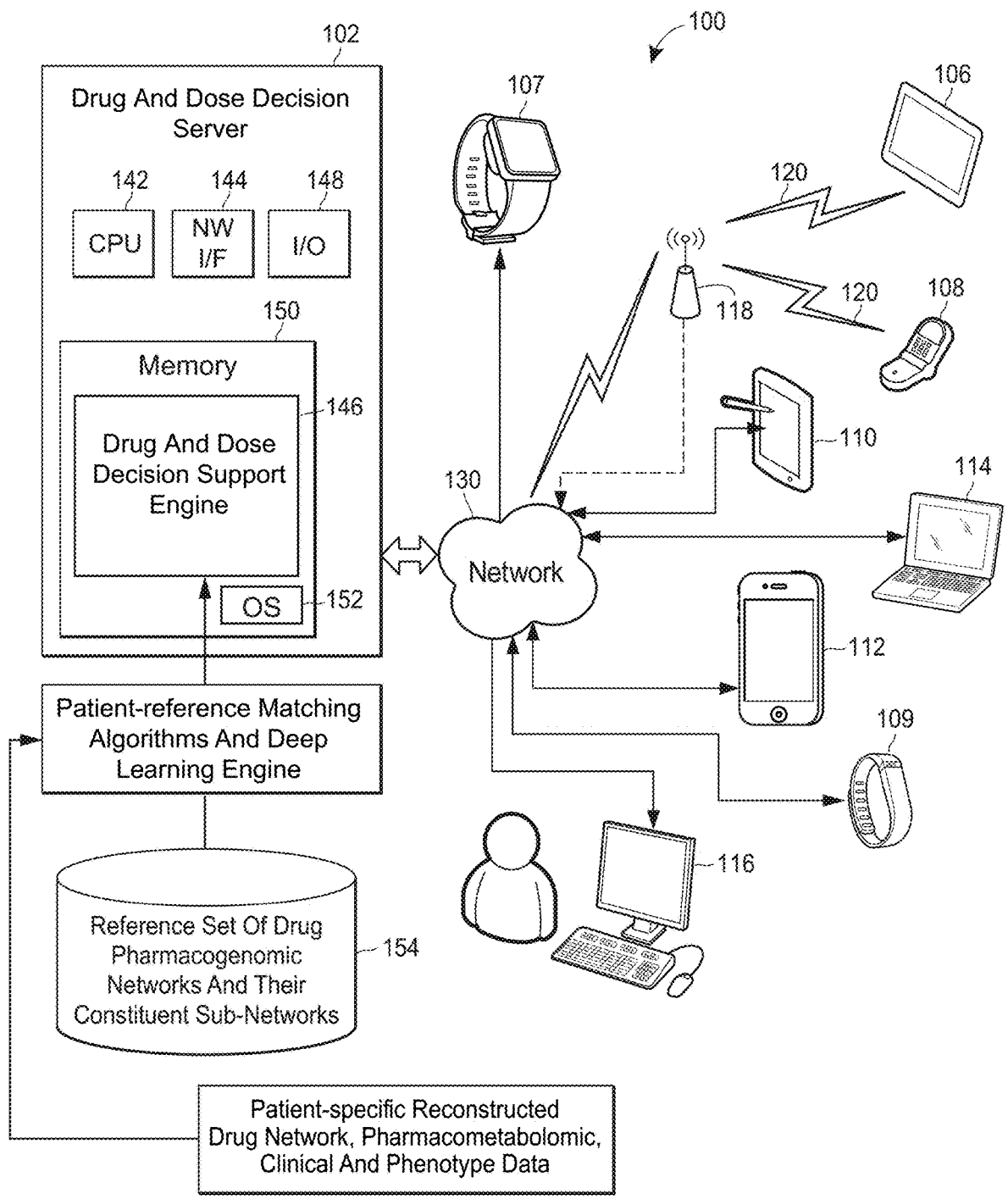
FIG. 1A illustrates a block diagram of a computer network and system on which an exemplary companion diagnostic system may operate in accordance with the presently described embodiments.

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term ' ' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

This disclosure comprises a system and methods for stratification of patients or cohort of patients diagnosed with a psychiatric disorder or requiring these drugs for other clinical indications for accurate medication selection and dose of a NMDAR antagonist. Ketamine is used as an exemplar, but these methods can be used for NMDAR antagonists or α-amino-3-hydroxy-5-methyl-4-isoxazolepropionic acid (AMPA) receptor modulators that are in clinical trials for a clinical indication of refractory depression. Ketamine and its enantiomers are novel antidepressants that exhibit greater efficacy and reduced side effects compared to other antidepressants for a patient or specific subset of patients diagnosed with TRD. The pharmacogenomic decision support system can determine which patients diagnosed with TRD should receive ketamine or one its enantiomers as an antidepressant medication, and if so, what the appropriate dosage should be for an individual patient or cohort of patients to maximize efficacy, minimize adverse drug events and drug-drug interactions, and reduce the harmful effects of drug-gene and drug-drug interactions. The adverse psychotropic side effects, including psychotomimetic and neurocognitive effects of glutamate receptor targeted medications for alleviation of depression, coupled with the heterogeneity of the patient population who may exhibit treatment-resistant depression (TRD) is based on multiple variables, including demographic and sociological variables, trauma history, genotype and clinical variables.

The system includes several methods that can be used for configuration of a clinical decision support diagnostic for selection and dosing of ketamine or one its enantiomers as an antidepressant in refractory depression and may be generalized to other psychotropic medications. One embodiment includes an integrated multi-scale measurement system that comprises the components shown in FIG. 1D, where patient biosamples can be extensively analyzed as shown in FIG. 2 and other relevant clinical data may also be obtained.

In some embodiments, the system is configured to analyze the minimal amount of results from the biosample required to match a stored cohort sub-network reference set. In this case, patient data is compared with a reference set of drug sub-networks that span the entire range of human drug response cohorts using a learning machine which has been pre-trained on the cohort response range for a particular drug, and the match to a reference set prompts a clinical decision recommendation. For example, the reference set of drug sub-networks may include a set of reference drug pharmacodynamic efficacy sub-networks, reference drug pharmacodynamic adverse event sub-networks, reference chromatin remodeling sub-networks, and reference pharmacokinetic enzymes and hormones sub-networks for the particular drug.

An electronic encryption broker is first used to protect health information through de-identification and to prevent patient identification. Biological sample(s) (e.g., blood, cheek swab, saliva, urine or other bodily fluid) are obtained from a patient or cohort of patients with accompanying clinical data from a medical record, such as an electronic health record (EHR) or other source. Initial pharmacometabolomic analysis on small blood samples, or plasma components thereof, collected from a patient or cohort of patients is performed for determination of potential drug-drug and drug-gene interactions that might alter subsequent pharmacogenomic decision support. These objective measurements augment self-reported, clinician-reported or other data contained in an EHR or another patient record.

Generally speaking, techniques for determining whether to administer a drug to a patient, such as a glutamate NMDAR antagonist or partial antagonist, GLRB modulator, or AMPAR agonist, and/or determining the appropriate dosage of the drug to administer to the patient may be implemented in one or several client devices, one or several network servers, or a system that includes a combination of these devices. However, for clarity, the examples below focus primarily on an embodiment in which a health care professional obtains a patient's biological sample and provides the biological sample to an assay laboratory for analysis.

The biological sample may include the subject's skin, blood, urine, sweat, lymph fluid, bone marrow, cheek cells, saliva, cell lines, tissues, etc. Cells are then extracted from the biological sample and reprogrammed into stem cells, such as induced pluripotent stem cells (iPSCs). Then the iPSCs are differentiated into various tissues, such as neurons, cardiomyocytes, etc., and assayed to obtain genomic data, chromosomal data, metabolomic data, etc. for the patient. In some embodiments, the iPSCs may be assayed for loci associated with or causatively associated a phenotypic response to the drug of interest. iPSCs comprise part of the reference set used to derive variables for assessing individual patients.

The drug and dose decision server relies on the drug and dose decision support engine. This engine receives a numerical score representing the overlap between an input patient sample as shown in FIG. 2 with the relevant drug-specific reference pharmacogenomic network stored in a database of such references 154. The system uses a learning machine trained on the entire range of human drug response cohorts, which consists of the pharmacogenomic network reference set for a particular drug, encompassing the range of human drug response variation to a particular drug that comprises the reference set to match to the input patient sample.

The drug and dose decision server analyzes the laboratory results to determine a sub-network representation for the patient for a drug gene set for an NMDAR antagonist or partial antagonist, GLRB modulator, or AMPAR agonist such as ketamine. Additionally, the drug and dose decision server retrieves a reference pharmacogenomic network and constituent reference sub-networks for the NMDAR antagonist or partial antagonist, GLRB modulator, or AMPAR agonist for example, from a reference drug pharmacogenomic network database. Then the drug and dose decision server compares the drug sub-network representation for the patient to the reference pharmacogenomic network and constituent reference sub-networks for the drug to determine whether to administer the drug to the patient. For example, the drug and dose decision server may compare an efficacy drug-specific (e.g., ketamine) sub-network for the patient to a reference efficacy drug-specific (e.g., ketamine) sub-network and may compare an adverse event drug-specific (e.g., ketamine) sub-network for the patient to a reference adverse event drug-specific (e.g., ketamine) sub-network. The drug and dose decision server may then determine that the patient should be administered the drug if the similarity between the efficacy drug-specific sub-network for the patient and the reference efficacy drug-specific sub-network is greater than a threshold (indicating the drug is likely to be effective on the patient). The drug and dose decision server may also determine that the patient should be administered the drug if the similarity between the adverse event drug-specific sub-network for the patient and reference adverse event drug-specific sub-network is below a threshold (indicating the patient is unlikely to experience adverse events), or based on some combination of the two.

Accordingly, the drug and dose decision server may provide a recommendation to a health care professional's client device indicating that the patient should receive the drug, thereby causing the health care professional to administer the drug to the patient. As a result, the health care professional may administer the drug to the patient. In some embodiments, the drug and dose decision server may determine a dosage of the drug to administer to the patient according to a dosing algorithm. The dosing algorithm may be determined using machine learning techniques such as linear regression and may be based on demographic data for the patient, clinical data for the patient, biological data for the patient, etc.

The drug and dose decision server may determine the dosage of the drug to administer to the patient and perform other methods described herein using various machine learning techniques, including, but not limited to regression algorithms (e.g., ordinary least squares regression, linear regression, logistic regression, stepwise regression, multivariate adaptive regression splines, locally estimated scatterplot smoothing, etc.), instance-based algorithms (e.g., k-nearest neighbors, learning vector quantization, self-organizing map, locally weighted learning, etc.), regularization algorithms (e.g., Ridge regression, least absolute shrinkage and selection operator, elastic net, least-angle regression, etc.), decision tree algorithms (e.g., classification and regression tree, iterative dichotomizer 3, C4.5, C5, chi-squared automatic interaction detection, decision stump, M5, conditional decision trees, etc.), clustering algorithms (e.g., k-means, k-medians, expectation maximization, hierarchical clustering, spectral clustering, mean-shift, density-based clustering of applications with noise, ordering points to identify the clustering structure, etc.), association rule learning algorithms (e.g., a priori algorithm, Eclat algorithm, etc.), Bayesian algorithms (e.g., naïve Bayes, Gaussian naïve Bayes, multinomial naïve Bayes, averaged one-dependence estimators, Bayesian belief network, Bayesian network, etc.), artificial neural networks (e.g., perceptron, Hopfield network, radial basis function network, etc.), deep learning algorithms (e.g., multilayer perceptron, deep Boltzmann machine, deep belief network, convolutional neural network, stacked autoencoder, generative adversarial network, etc.), dimensionality reduction algorithms (e.g., principal component analysis, principal component regression, partial least squares regression, Sammon mapping, multidimensional scaling, projection pursuit, linear discriminant analysis, mixture discriminant analysis, quadratic discriminant analysis, flexible discriminant analysis, factor analysis, independent component analysis, non-negative matrix factorization, t-distributed stochastic neighbor embedding, etc.), ensemble algorithms (e.g., boosting, bootstrapped aggregation, AdaBoost, stacked generalization, gradient boosting machines, gradient boosted regression trees, random decision forests, etc.), reinforcement learning (e.g., temporal difference learning, Q-learning, learning automata, State-Action-Reward-State-Action, etc.), support vector machines, mixture models, evolutionary algorithms, probabilistic graphical models, etc.

Referring to FIG. 1A, an example pharmacogenomic decision support system 100 determines whether to administer a psychotropic drug to a patient suffering from depression such as a patient with TRD, and the appropriate dosage for the psychotropic drug. The pharmacogenomic decision support system 100 includes a drug and dose decision server 102 and a plurality of client devices 106-116 which may be communicatively connected through a network 130, as described below. In an embodiment, the drug and dose decision server 102 and the client devices 106-116 may communicate via wireless signals 120 over a communication network 130, which can be any suitable local or wide area network(s) including a WiFi network, a Bluetooth network, a cellular network such as 3G, 4G, Long-Term Evolution (LTE), 5G, the Internet, etc. In some instances, the client devices 106-116 may communicate with the communication network 130 via an intervening wireless or wired device 118, which may be a wireless router, a wireless repeater, a base transceiver station of a mobile telephony provider, etc. The client devices 106-116 may include, by way of example, a tablet computer 106, a smart watch 107, a network-enabled cell phone 108, a wearable computing device such as Google Glass™ or a Fitbit® 109, a personal digital assistant (PDA) 110, a mobile device smart-phone 112 also referred to herein as a "mobile device," a laptop computer 114, a desktop computer 116, wearable biosensors, a portable media player (not shown), a phablet, any device configured for wired or wireless RF (Radio Frequency) communication, etc. Moreover, any other suitable client device that record clinical data for patients may also communicate with the drug and dose decision server 102.

Each of the client devices 106-116 may interact with the drug and dose decision server 102 to receive a recommendation on whether to administer the psychotropic drug to the patient and the dosage for the psychotropic drug. The client device 106-116 may present the recommendation via a user interface for display to a health care professional.

In an example implementation, the drug and dose decision server 102 may be a cloud based server, an application server, a web server, etc., and includes a memory 150, one or more processors (CPU) 142 such as a microprocessor coupled to the memory 150, a network interface unit 144, and an I/O module 148 which may be a keyboard or a touchscreen, for example.

The drug and dose decision server 102 may also be communicatively connected to a database 154 of reference drug pharmacogenomic networks and constituent sub-networks such as efficacy and adverse-event sub-networks for the drug.

The memory 150 may be tangible, non-transitory memory and may include any types of suitable memory modules, including random access memory (RAM), read only memory (ROM), flash memory, other types of persistent memory, etc. The memory 150 may store, for example instructions executable of the processors 142 for an operating system (OS) 152 which may be any type of suitable operating system such as modern smartphone operating systems, for example. The memory 150 may also store, for example instructions executable on the processors 142 for a drug and dose decision support engine 146. The drug and dose decision server 102 is described in more detail below with reference to FIG. 1B. In some embodiments, the drug and dose decision support engine 146 may be a part of one or more of the client devices 106-116, the drug and dose decision server 102, or a combination of the drug and dose decision server 102 and the client devices 106-116.

In any event, the drug and dose decision support engine 146 may obtain laboratory results from the patient biosample only as is necessary to match one of the sets of pharmacogenomic networks and their constituent sub-networks that define human drug response variation for the particular drug. These include molecular data that includes variation in the genome defined by SNPs in PD and PK genes, pharmacogenomic interactions between regulatory elements, genes in a patient's genome that can be defined using chromosome conformation data such as Hi-C, and/or direct topologically associating domain (TAD)-specific measures, including differential gene expression determined using RNA sequencing (RNA-Seq) or expression microarray profiling and patient-specific TAD contactome measures in relevant or surrogate cell types using chromosome conformation capture (e.g., 3C, 4C, 5C, Hi-C, ChIA-PET and GAM). The molecular data may be assayed for loci associated with or causatively associated a phenotypic response to the drug of interest. Additionally, the drug and dose decision support engine 146 may obtain a reference pharmacogenomic network and constituent reference sub-networks for the psychotropic drug of interest (e.g., ketamine) from a reference drug pharmacogenomic network database 154.

Then the drug and dose decision support engine 146 may analyze the laboratory results for the patient to determine a sub-network representation for the psychotropic drug of interest, such as an efficacy sub-network and an adverse event sub-network. The drug and dose decision support engine 146 may compare the efficacy sub-network and an adverse event sub-network for the patient to reference efficacy and adverse event sub-networks to determine whether to administer the psychotropic drug of interest to the patient. If the similarity between the efficacy drug-specific sub-network for the patient and the reference efficacy drug-specific sub-network is greater than a threshold and/or the similarity between the adverse event drug-specific sub-network for the patient and reference adverse event drug-specific sub-network is below a threshold, the drug and dose decision support engine 146 may determine that the patient should be administered the psychotropic drug of interest. The drug and dose decision support engine 146 may then provide a recommendation to a health care professional's client device 106-116 indicating that the patient should receive the psychotropic drug of interest. Otherwise, the drug and dose decision support engine 146 may provide a recommendation of another drug to administer to the patient to treat depression. Furthermore, the drug and dose decision support engine 146 may determine a dosage of the psychotropic drug of interest to administer to the patient according to a dosing algorithm. The drug and dose decision support engine 146 may also provide a recommended dosage for the psychotropic drug of interest to the health care professional's client device 106-116.

The drug and dose decision server 102 may communicate with the client devices 106-116 via the network 130. The digital network 130 may be a proprietary network, a secure public Internet, a virtual private network and/or some other type of network, such as dedicated access lines, plain ordinary telephone lines, satellite links, combinations of these, etc. Where the digital network 130 comprises the Internet, data communication may take place over the digital network 130 via an Internet communication protocol.

Figure 1B:
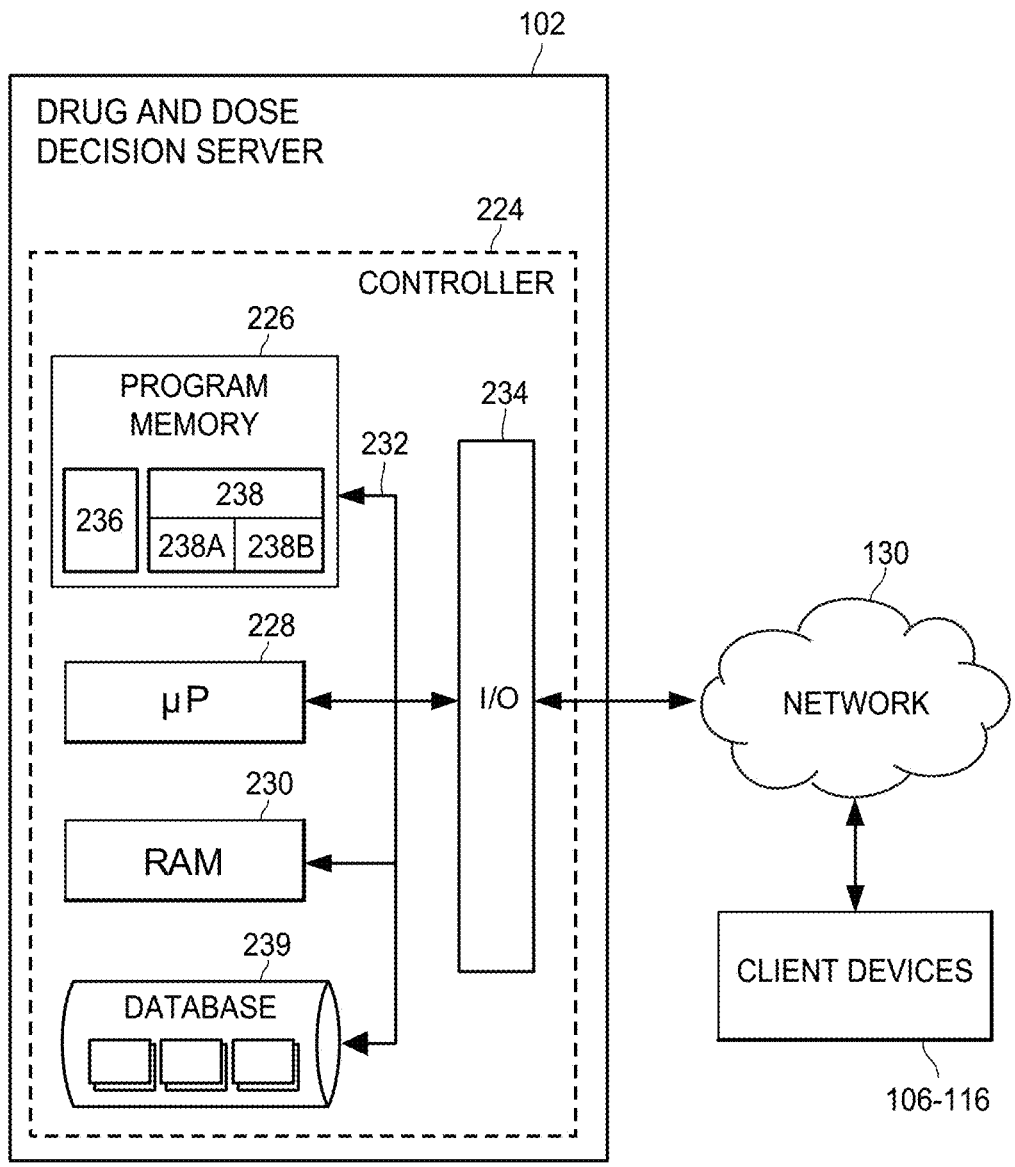
FIG. 1B is a block diagram of an exemplary drug and dose decision server that can operate in the system of FIG. 1A in accordance with the presently described embodiments.

Turning now to FIG. 1B, the drug and dose decision server 102 may include a controller 224. The controller 224 may include a program memory 226, a microcontroller or a microprocessor (MP) 228, a random-access memory (RAM) 230, and/or an input/output (I/O) circuit 234, all of which may be interconnected via an address/data bus 232. In some embodiments, the controller 224 may also include, or otherwise be communicatively connected to, a database 239 or other data storage mechanism (e.g., one or more hard disk drives, optical storage drives, solid state storage devices, etc.). The database 239 may include data such as drug pharmacogenomic network reference data, drug recommendation display templates, web page templates and/or web pages, and other data necessary to interact with users through the network 130. The database 239 may include similar data as the database 154 described above with reference to FIG. 1A.

It should be appreciated that although FIG. 1B depicts only one microprocessor 228, the controller 224 may include multiple microprocessors 228. Similarly, the memory of the controller 224 may include multiple RAMs 230 and/or multiple program memories 226. Although FIG. 1B depicts the I/O circuit 234 as a single block, the I/O circuit 234 may include a number of different types of I/O circuits. The controller 224 may implement, for example, the RAM(s) 230 and/or the program memories 226 as semiconductor memories, magnetically readable memories, and/or optically readable memories.

As shown in FIG. 1B, the program memory 226 and/or the RAM 230 may store various applications for execution by the microprocessor 228. For example, a user-interface application 236 may provide a user interface to the drug and dose decision server 102, which user interface may, for example, allow a system administrator to configure, troubleshoot, or test various aspects of the server's operation. A server application 238 may operate to receive molecular data for a patient, analyze the molecular data to determine sub-networks for the patient related to a particular drug of interest, compare the sub-networks for the patient to reference sub-networks for the particular drug of interest, determine to administer the particular drug of interest to the patient based on the comparison, and transmit a recommendation to administer the particular drug of interest to the patient to a client device 106-116. The server application 238 may be a single module 238 such as the drug and dose decision support engine 146 or a plurality of modules 238A, 238B.

While the server application 238 is depicted in FIG. 1B as including two modules, 238A and 238B, the server application 238 may include any number of modules accomplishing tasks related to implementation of the drug and dose decision server 102. Moreover, it will be appreciated that although only one drug and dose decision server 102 is depicted in FIG. 1B, multiple drug and dose decision servers 102 may be provided for the purpose of distributing server load, serving different web pages, etc. These multiple drug and dose decision servers 102 may include a web server, an entity-specific server (e.g. an Apple® server, etc.), a server that is disposed in a retail or proprietary network, etc.

Figure 1C:
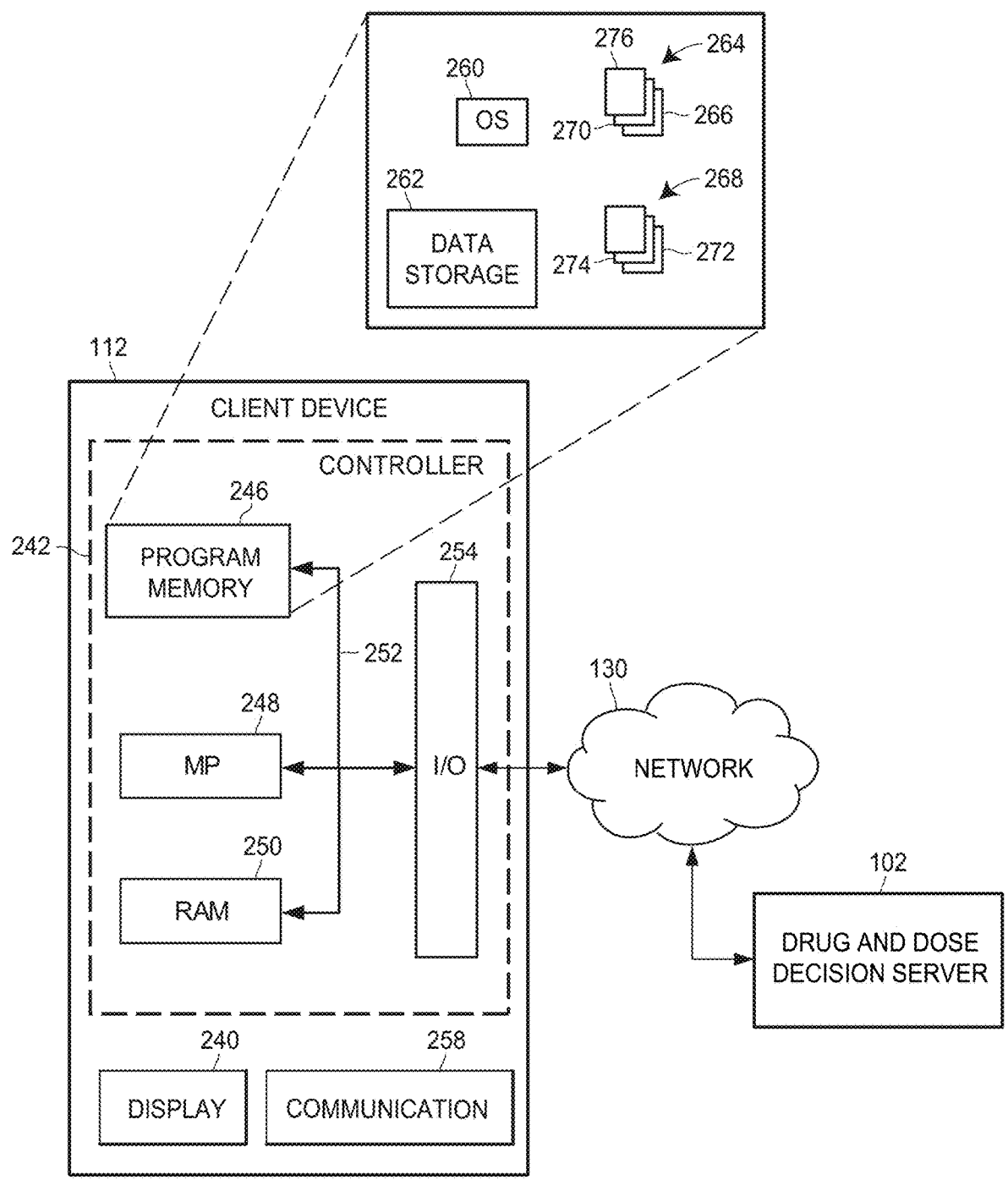
FIG. 1C is a block diagram of an exemplary client device that can operate in the system of FIG. 1A in accordance with the presently described embodiments.

Referring now to FIG. 1C, the laptop computer 114 (or any of the client devices 106-116) may include a display 240, a communication unit 258, a user-input device (not shown), and, like the drug and dose decision server 102, a controller 242. Similar to the controller 224, the controller 242 may include a program memory 246, a microcontroller or a microprocessor (MP) 248, a random-access memory (RAM) 250, and/or an input/output (I/O) circuit 254, all of which may be interconnected via an address/data bus 252. The program memory 246 may include an operating system 260, a data storage 262, a plurality of software applications 264, and/or a plurality of software routines 268. The operating system 260, for example, may include Microsoft Windows®, OS X®, Linux®, Unix®, etc. The data storage 262 may include data such as application data for the plurality of applications 264, routine data for the plurality of routines 268, and/or other data necessary to interact with the drug and dose decision server 102 through the digital network 130. In some embodiments, the controller 242 may also include, or otherwise be communicatively connected to, other data storage mechanisms (e.g., one or more hard disk drives, optical storage drives, solid state storage devices, etc.) that reside within the laptop computer 114.

The communication unit 258 may communicate with the drug and dose decision server 102 via any suitable wireless communication protocol network, such as a wireless telephony network (e.g., GSM, CDMA, LTE, etc.), a Wi-Fi network (802.11 standards), a WiMAX network, a Bluetooth network, etc. The user-input device (not shown) may include a "soft" keyboard that is displayed on the display 240 of the laptop computer 114, an external hardware keyboard communicating via a wired or a wireless connection (e.g., a Bluetooth keyboard), an external mouse, a microphone for receiving voice input or any other suitable user-input device.

As discussed with reference to the controller 224, it should be appreciated that although FIG. 1C depicts only one microprocessor 248, the controller 242 may include multiple microprocessors 248. Similarly, the memory of the controller 242 may include multiple RAMs 250 and/or multiple program memories 246. Although the FIG. 1C depicts the I/O circuit 254 as a single block, the I/O circuit 254 may include a number of different types of I/O circuits. The controller 242 may implement the RAM(s) 250 and/or the program memories 246 as semiconductor memories, magnetically readable memories, and/or optically readable memories, for example.

The one or more processors 248 may be adapted and configured to execute any one or more of the plurality of software applications 264 and/or any one or more of the plurality of software routines 268 residing in the program memory 246, in addition to other software applications. One of the plurality of applications 264 may be a client application 266 that may be implemented as a series of machine-readable instructions for performing the various tasks associated with receiving information at, displaying information on, and/or transmitting information from the laptop computer 114.

One of the plurality of applications 264 may be a native application and/or web browser 270, such as Apple's Safari®, Google Chrome™, Microsoft Internet Explorer®, and Mozilla Firefox® that may be implemented as a series of machine-readable instructions for receiving, interpreting, and/or displaying web page information from the drug and dose decision server 102 while also receiving inputs from a user such as a health care professional or researcher. Another application of the plurality of applications may include an embedded web browser 276 that may be implemented as a series of machine-readable instructions for receiving, interpreting, and/or displaying web page information from the drug and dose decision server 102.

One of the plurality of routines may include a drug recommendation display routine 272 which presents a recommendation of whether to administer a psychotropic drug of interest to a patient and/or a recommended dosage on the display 240.

Preferably, a user may launch the client application 266 from a client device, such as one of the client devices 106-116 to communicate with the drug and dose decision server 102 to implement the companion diagnostic system 100. Additionally, the user may also launch or instantiate any other suitable user interface application (e.g., the native application or web browser 270, or any other one of the plurality of software applications 264) to access the drug and dose decision server 102 to realize the companion diagnostic system 100.

Figure 1D:
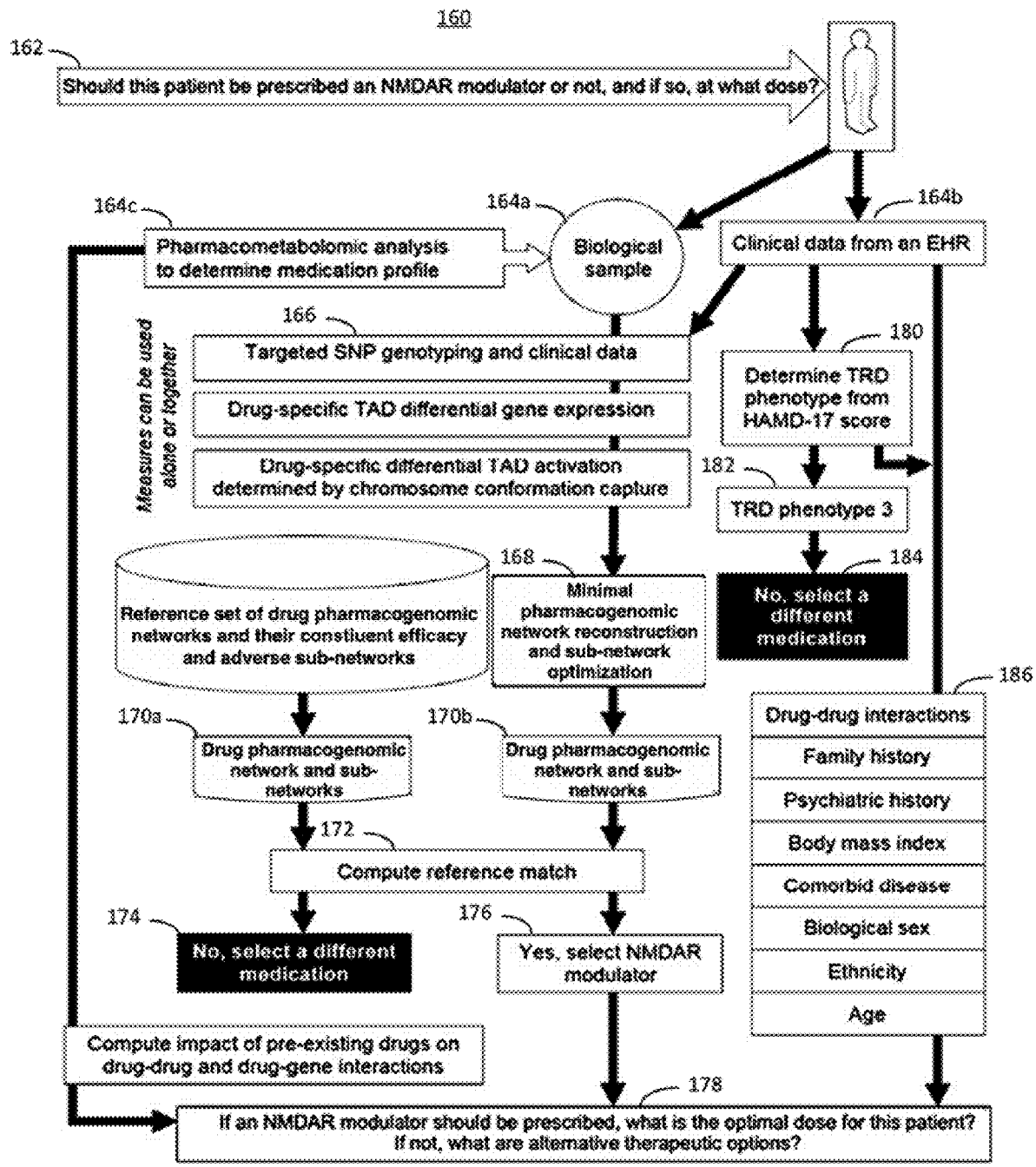
FIG. 1D illustrates a flow diagram representing an exemplary method for determining a drug and dosage to administer to a patient suffering from depression or other neuropsychiatric illness based on comparing data from the patient's biological sample to a reference drug-specific pharmacogenomic network and the constituent sub-networks for the drug of interest.
Figure 2:
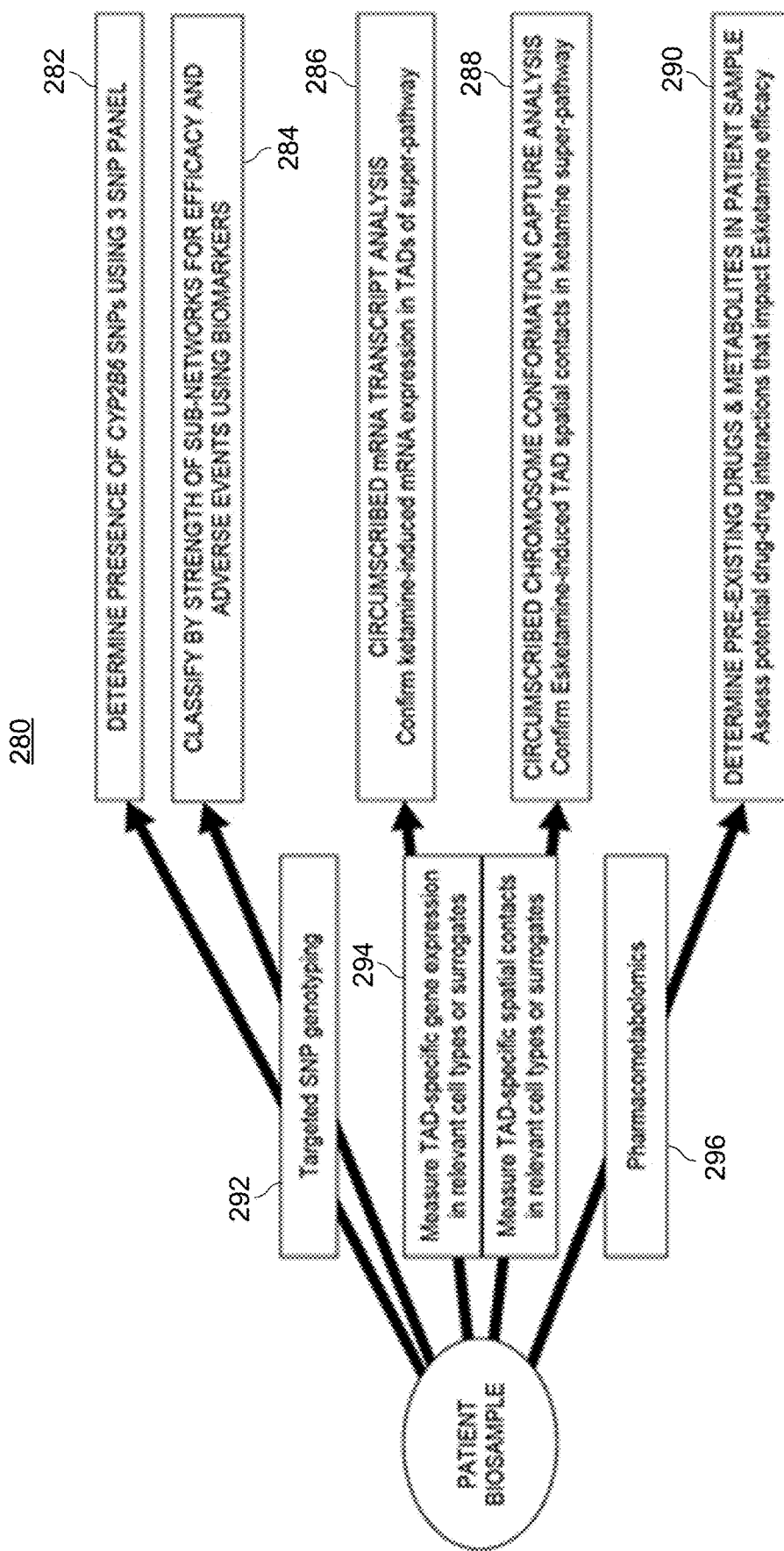
FIG. 2 illustrates example measurements collected from a patient's biological sample using chromosome conformation capture, bioinformatics analysis, and/or similar measures.

FIG. 1D illustrates a flow diagram representing an exemplary method 160 for determining a drug and dosage to administer to a patient suffering from depression based on comparing data from a patient's biological sample to a reference pharmacogenomic network and constituent sub-networks for the drug of interest. The method 160 may be executed by the drug and dose decision server 102.

In some embodiments, patient bio-samples are analyzed as shown in FIG. 1D for personalized therapy to quantify the relative activation of the different pathways that mediate ketamine's mechanisms of action in the human CNS determined using the methods described herein. Patient or patient cohort biosamples may be analyzed using pharmacometabolomic assays for determination of drug or metabolites in samples that may cause unwanted drug-drug-interactions, impacting the efficacy, adverse events and dosing of the medication. Biosample measurement includes: (1) genotyping of pharmacokinetic SNPs, in the exemplar of ketamine consisting of mutations in the CYP2B6 gene that have been shown to be determinative of metabolizer status (poor, subnormal, normal or ultra-rapid subtypes), (2) pharmacodynamic SNP targeting as inputs into pharmacogenomic network and sub-network profiling, which is deterministic of both efficacy and adverse events as analyzed using the pharmacogenomic genome classifier and pharmacodynamic sub-network profiling systems, (3) direct topologically associating domain (TAD)-specific measures including differential gene expression determined using RNA sequencing (RNA-Seq) or expression microarray profiling, and patient-specific TAD contactome measures in relevant or surrogate cell types using chromosome conformation capture (e.g., 3C, 4C, 5C, Hi-C, ChIA-PET and GAM), and (4) pharmacometabolomic analysis.

The data processing pipeline shown in FIG. 1D comprises parallel routes for analysis of the biosample using multiple methods, and analysis of available clinical data for the same patient as might be collected from an electronic health record (EHR). This example illustrates the analytics used to determine whether a specific patient should be administered an N-methyl-D-aspartate receptor (NMDAR) modulator. The adverse events associated with NMDAR modulators such as ketamine may be severe, including severe dissociation, hallucinations and nightmares. Thus, the first decision to be made from these parallelized analytics is to ensure that the patient does not receive NMDAR modulators such as ketamine if the system predicts that the individual will experience moderate to serious adverse events.

Figure 20:
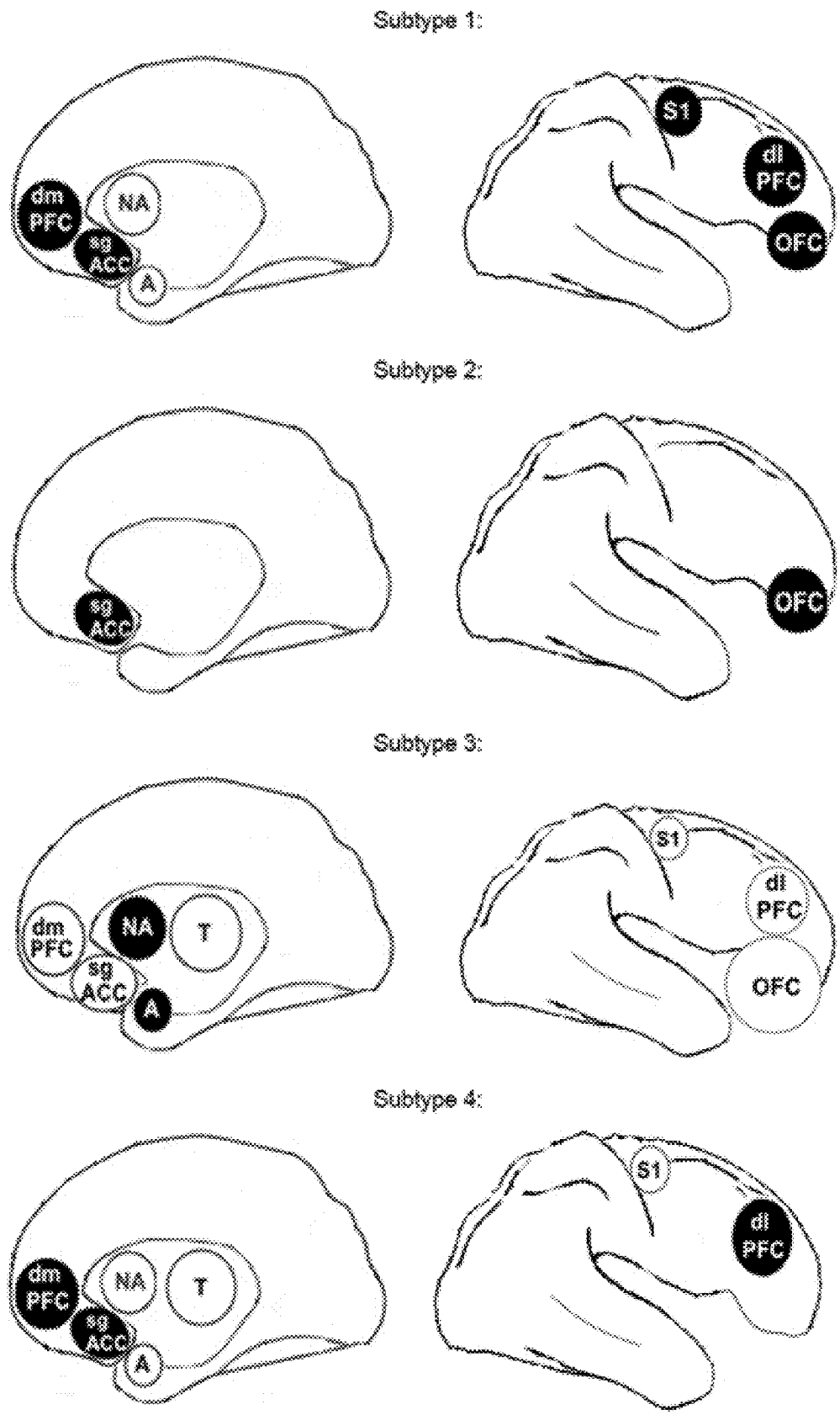
FIG. 20 illustrates example neuromaps for the four different subtypes of TRD depressed patients.
Figure 22:
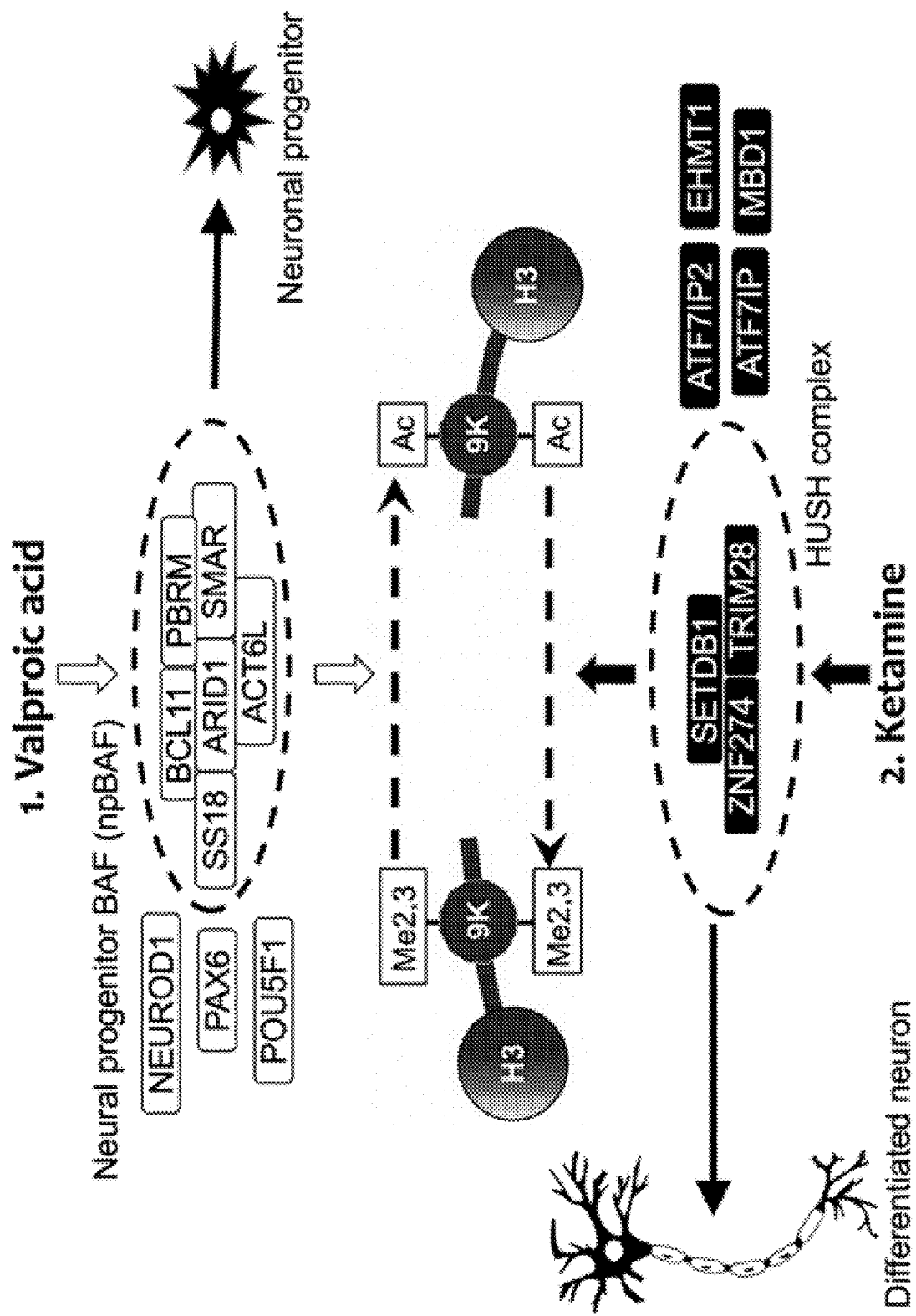
FIG. 22 illustrates an example of beneficial combinatorial mechanisms and therapeutics mediated by synergistic histone modifications discovered using the methods described herein using valproic acid and ketamine in H3K9 acetylation and deacetylation respectively, leading to neurogenesis and neuro-differentiation, in combination.

The data processing pipeline shown in FIG. 1D may determine a "no-go" decision on administration of NMDAR modulators such as ketamine based on the molecular network representation in the patient, certain disease risk SNPs that the patient may harbor as shown in FIG. 23, the treatment-resistant depression phenotype of the patient as shown in FIG. 20 and FIG. 22, as well as a dose adjustment based on the pharmacometabolic profile of the patient. If the system decides that the patient may receive an NMDAR modulator such as ketamine, a dose determination algorithm is then initiated.

The method 160 is utilized as a clinical decision support diagnostic to determine whether the patient should be prescribed an NMDAR modular as an antidepressant (block 162) and the optimal dosage for the patient. In some embodiments, patient bio-samples are analyzed (block 164a) for personalized therapy to quantify the relative activation of the different pathways that mediate ketamine's mechanisms of action in the human CNS determined using the methods described herein. Patient or patient cohort biosamples may be analyzed using pharmacometabolic assays for determination of drug or metabolites in samples that may cause unwanted drug-drug-interactions, impacting the efficacy, adverse events and dosing of the medication. At block 166, biosample measurements include: (1) genotyping of pharmacokinetic SNPs, in the exemplar of ketamine consisting of mutations in the CYP2B6 gene that have been shown to be determinative of metabolizer status (poor, subnormal, normal or ultra-rapid subtypes), (2) pharmacodynamic SNP targeting as inputs into pharmacogenomic network and sub-network profiling, which is deterministic of both efficacy and adverse events as analyzed using the pharmacogenomic genome classifier and pharmacodynamic sub-network profiling systems, (3) direct topologically associating domain (TAD)-specific measures including differential gene expression determined using RNA sequencing (RNA-Seq) or expression microarray profiling and patient-specific TAD contactome measures in relevant or surrogate cell types using chromosome conformation capture (e.g., 3C, 4C, 5C, Hi-C, ChIA-PET and GAM), and (4) pharmacometabolomic analysis (block 164c).

As described above, biosample measurements include pharmacodynamic SNP targeting as inputs into pharmacogenomic network and sub-network profiling (blocks 168, 170b), which is deterministic of both efficacy and adverse events as analyzed using the pharmacogenomic genome classifier and pharmacodynamic sub-network profiling systems. At block 170a, a reference pharmacogenomic network and sub-networks for the drug of interest are retrieved from a reference database. The patient's sub-networks for the particular drug of interest, which include efficacy and adverse event sub-networks, are then compared to the reference pharmacogenomic network and sub-networks for the drug of interest (block 172). For determination of similarity to the reference set, the two different pairs of reference-patient metrics include an accurate measurement of similarity and outputs similarity scores for each of the efficacy and adverse events sub-networks. At block 172, the similarity scores for the efficacy and adverse event sub-networks for the drug of interest may be used to determine whether to administer the drug of interest to the patient. For example, if the similarity score for the efficacy sub-network is above a threshold similarity score, the method 160 may determine that the drug of interest should be administered to the patient (block 176). Otherwise, the method 160 determines to select a different medication (block 174).

In addition to comparing the patient's sub-networks for the drug of interest to reference sub-networks for the drug of interest, at block 164b clinical data is collected and analyzed for the patient to determine whether to administer the drug to the patient and/or the dosage for the drug. More specifically, the patient's HAMD score and/or patient symptoms may be analyzed to categorize the patient into one of four TRD patient subtypes (block 180). The TRD patient subtypes are described in more detail below with reference to FIGS. 15-17. If the patient is categorized as TRD subtype 3 (block 182), the method 160 determines to select a different medication (block 184). Other clinical data may also be analyzed such as the patient's drug-drug interactions, age, weight, biological sex, body mass index, ethnicity, family history, patient history of substance abuse, diagnostic codes, hospitalization history, drug-gene interactions, mental illness history, whether the patient smokes or uses nicotine, etc. (block 186).

Then a dosage of the drug of interest is determined to administer to the patient (block 178). The dosage may be determined based on a dosing algorithm having predetermined constants to apply to each of several patient characteristics, such as biological characteristics, demographic characteristics, clinical characteristics, etc. In other embodiments, the dosing algorithm may be generated using machine learning techniques. The patient characteristics utilized in the dosing algorithm may include biological data, such as SNPs that have been reported to stratify response to ketamine in humans. The patient characteristics may also include demographic data for the patient, such as the patient's sex, height and weight, age, and ethnicity. Furthermore, the patient characteristics may include clinical data, such as family history, drug-drug interactions, mental illness history, whether the patient smokes or uses nicotine, and Hamilton Scale for Depression (HAM-D) score.

FIG. 2 shows various measures that may be undertaken from the patient's biosample. In one embodiment, blood and buccal swab samples are obtained and processed. For ketamine and other medications that undergo first pass metabolism by the protein encoded by the hyper-inducible and hyper-variable CYP2B6 gene, targeted SNP genotyping is performed using a 4-SNP panel, but most importantly, examination of the splicing variant SNP rs3745274 is prioritized, because it is relatively common (>10% frequency) among human populations, and carriers of this SNP comprise ultra-poor metabolizers of any drug which is primarily metabolized by this enzyme, and it is very likely to experience adverse drug events from an NMDAR modulator such as ketamine.

In the method illustrated in FIG. 1D and in the measurements collected FIG. 2, a pharmacometabolomic analysis of the patient's blood is recommended to rule out any possibility of negative drug-drug or drug-gene interactions.

FIG. 2 illustrates the analytics that may be performed on the patient's biosample to obtain the minimal information necessary to permit a machine or deep learning algorithm to match the drug-specific pattern of the reference set of comprehensive sub-networks that comprise activation of the topologically associating domains (TADs) contained in a database 154. These methods may include measurements of TAD-specific changes in gene expression using RNA-seq or expression microarrays, pharmacogenomic contacts between genes using chromosome conformation capture analysis such as Hi-C, and/or targeted genotyping following induction of geometric alterations in the pharmacogenomic genome by the drug, either after administration of the particular drug to the patient, or proactively, through analysis of a buccal swab obtained from the patient prior to deciding whether the drug should be administered or not.

The biosample measurements in FIG. 2 include genotyping of targeted pharmacokinetic and pharmacodynamic SNPs (block 292), direct TAD-specific measures including differential gene expression and pharmacogenomic contacts (block 294), and pharmacometabolomics (block 296). Genotyping of targeted pharmacokinetic and pharmacodynamic SNPs includes identifying mutations in the CYP2B6 gene that have been shown to be determinative of metabolizer status (block 282), and classifying the strength of efficacy and adverse events sub-networks according to pharmacogenomic network and sub-network profiling (block 284). The direct chromatin contact-specific measures include differential gene expression determined using circumscribed RNA sequencing (RNA-Seq) (block 286), and circumscribed chromosome conformation capture analysis to identify pharmacogenomic contacts (block 288). Moreover, the pharmacometabolomic analysis is used to identify pre-existing drugs and metabolites in the patient's biosample to assess potential drug-drug interactions, for example (block 290), and can be used to periodically monitor patient drug-drug interactions and drug adherence.

Figure 3A:
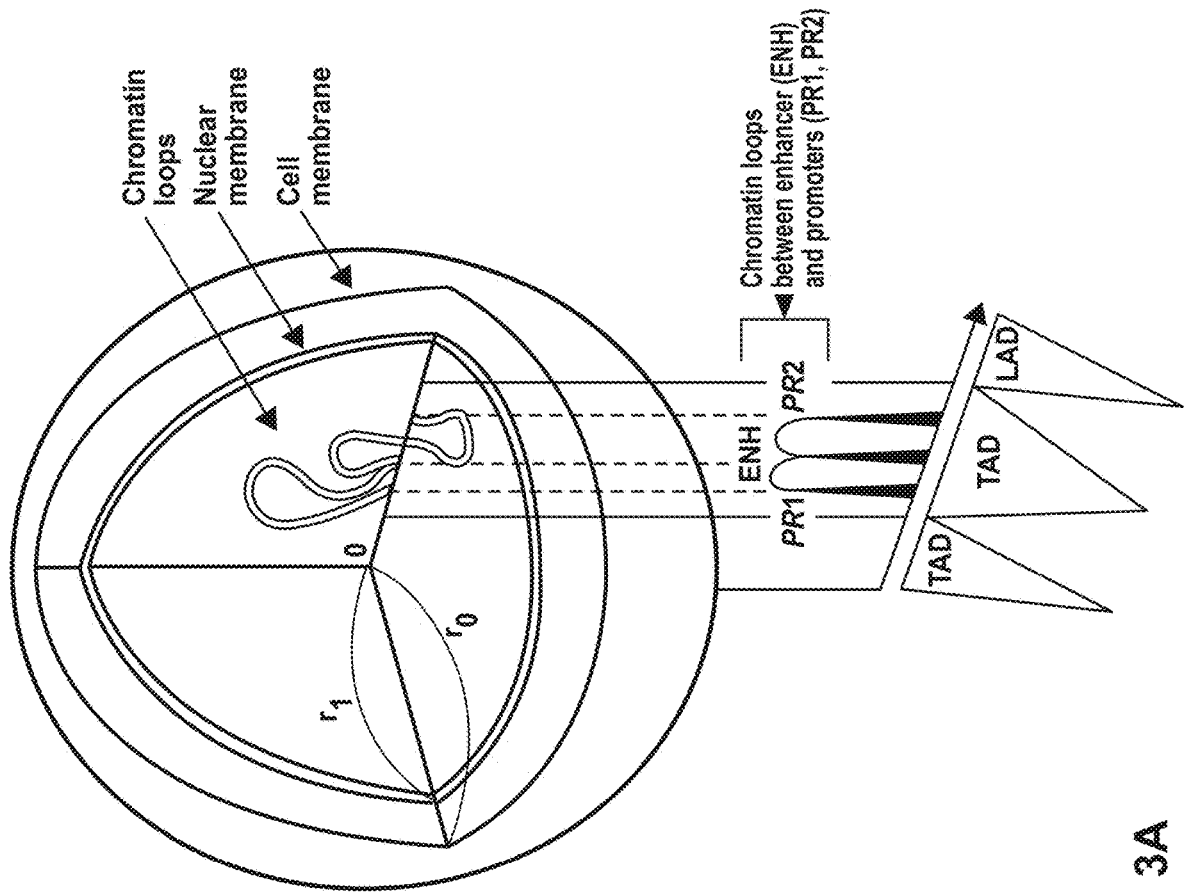
FIGS. 3A-3B show a simple example of how a SNP located within an enhancer in the network might disrupt the enhancer's contact with one of its target gene promoters in the TAD, leading to adverse drug events in a patient within a drug response cohort.
Figure 3B:
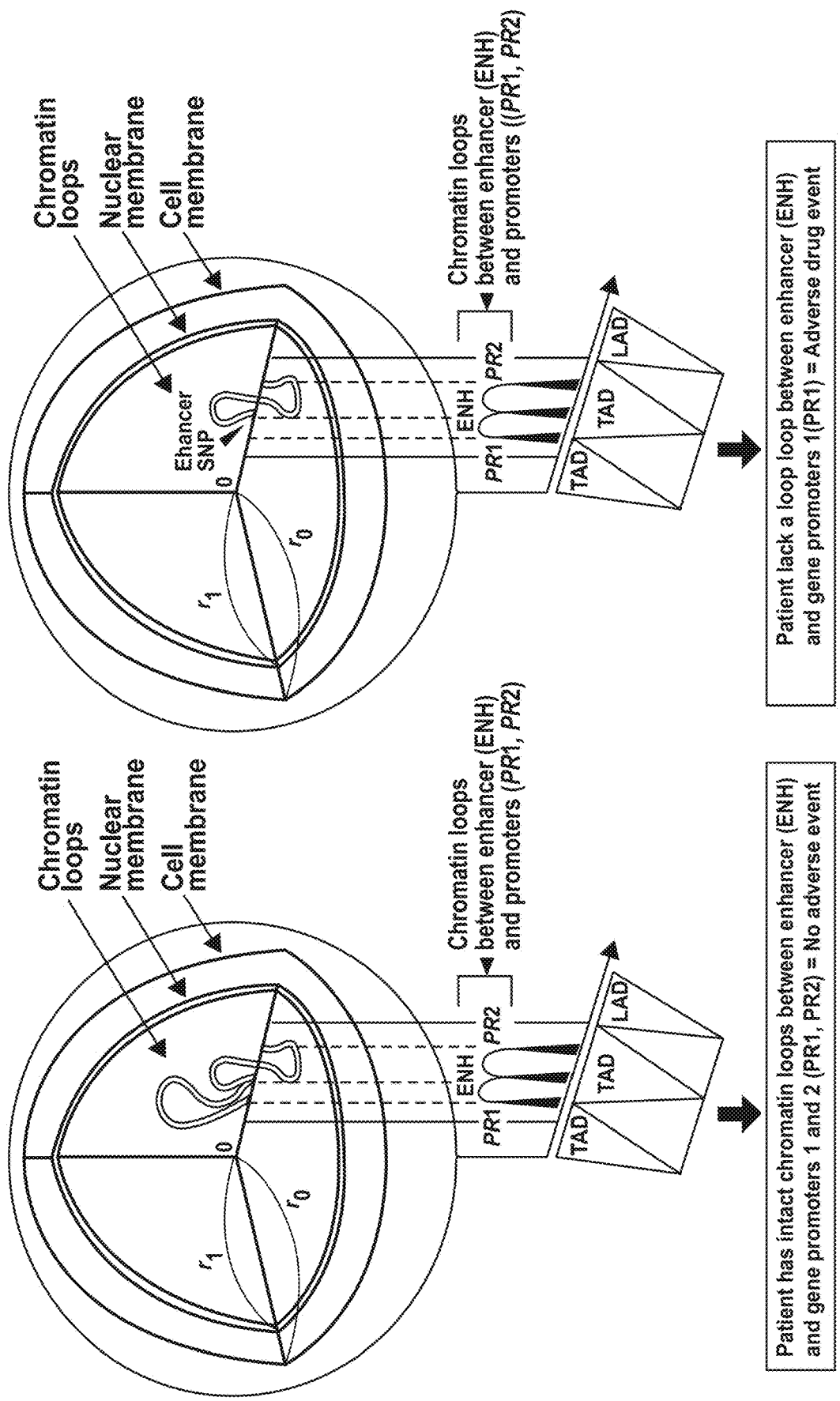

FIG. 3 shows a simple example of how a SNP located within an enhancer or super-enhancer in the network might disrupt the enhancer's contact with one of its target gene promoters in the TAD, leading to adverse drug events in a patient within a drug response cohort. FIG. 3A illustrates how different laboratory methods may be used to obtain measures from the chromatin pharmacogenomic interactome in three dimensions and analyze the data as 2 dimensional plots of enhancer-gene promoter interactions. FIG. 3B depicts how a SNP may disrupt a chromatin loop between an enhancer and one of two gene promoters that it regulates within a TAD. This disruption removes the pharmacogenomic connection between the enhancer and gene promoter 1 resulting in dysregulation of gene 1, resulting in an adverse event in this patient and its cohort in response to administration of the particular drug of interest.

Figures 2, 4:
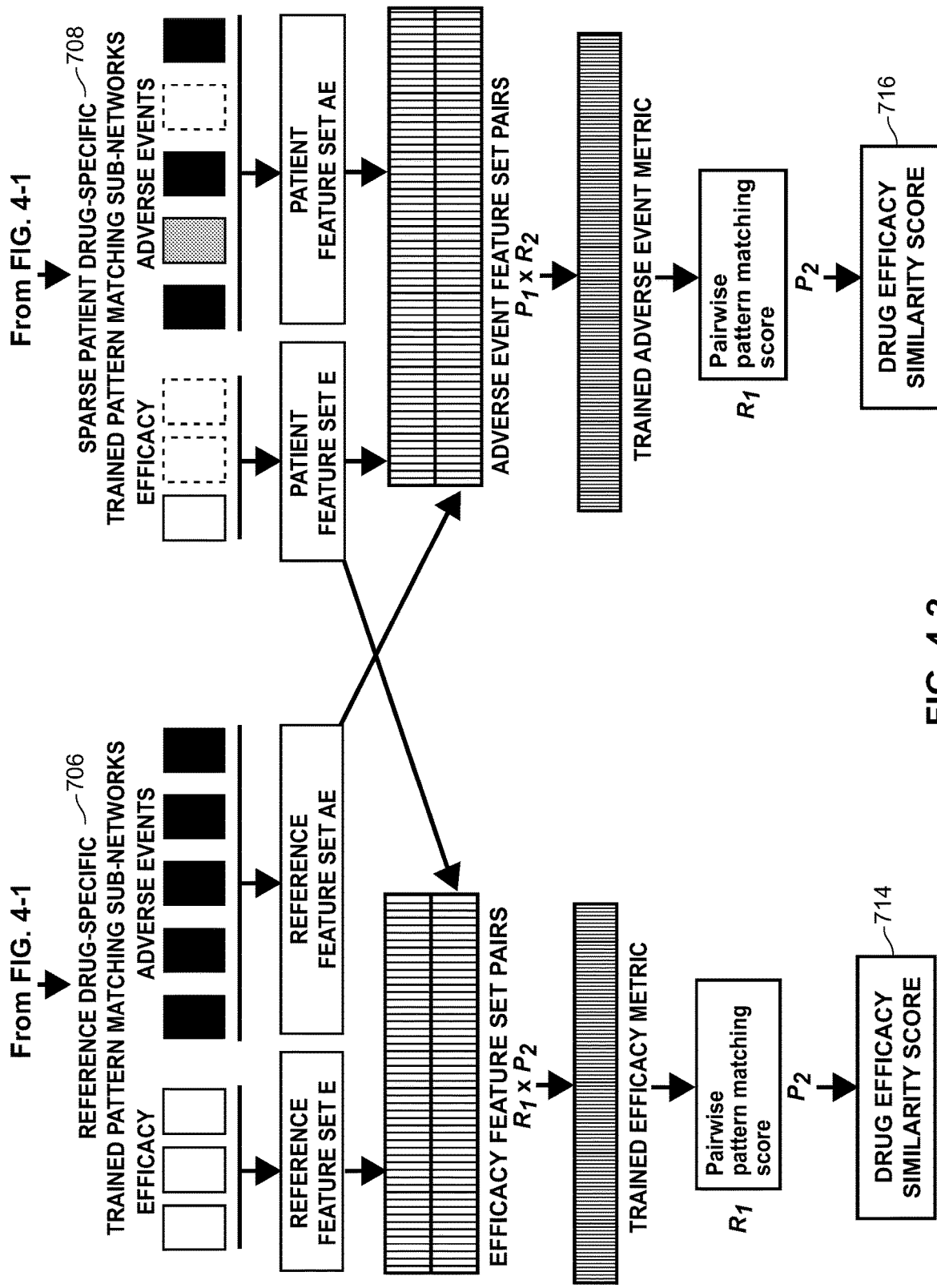

FIG. 4 illustrates the first of several embodiments for matching reference data to a patient input for clinical decision support. In this example, the pharmacogenomic drug sub-network reference set for a particular drug may be combined with a biosample input of sparse results from a patient and using a combinatorial co-training method be used to derive a drug efficacy score for decision-making.

Figure 5:
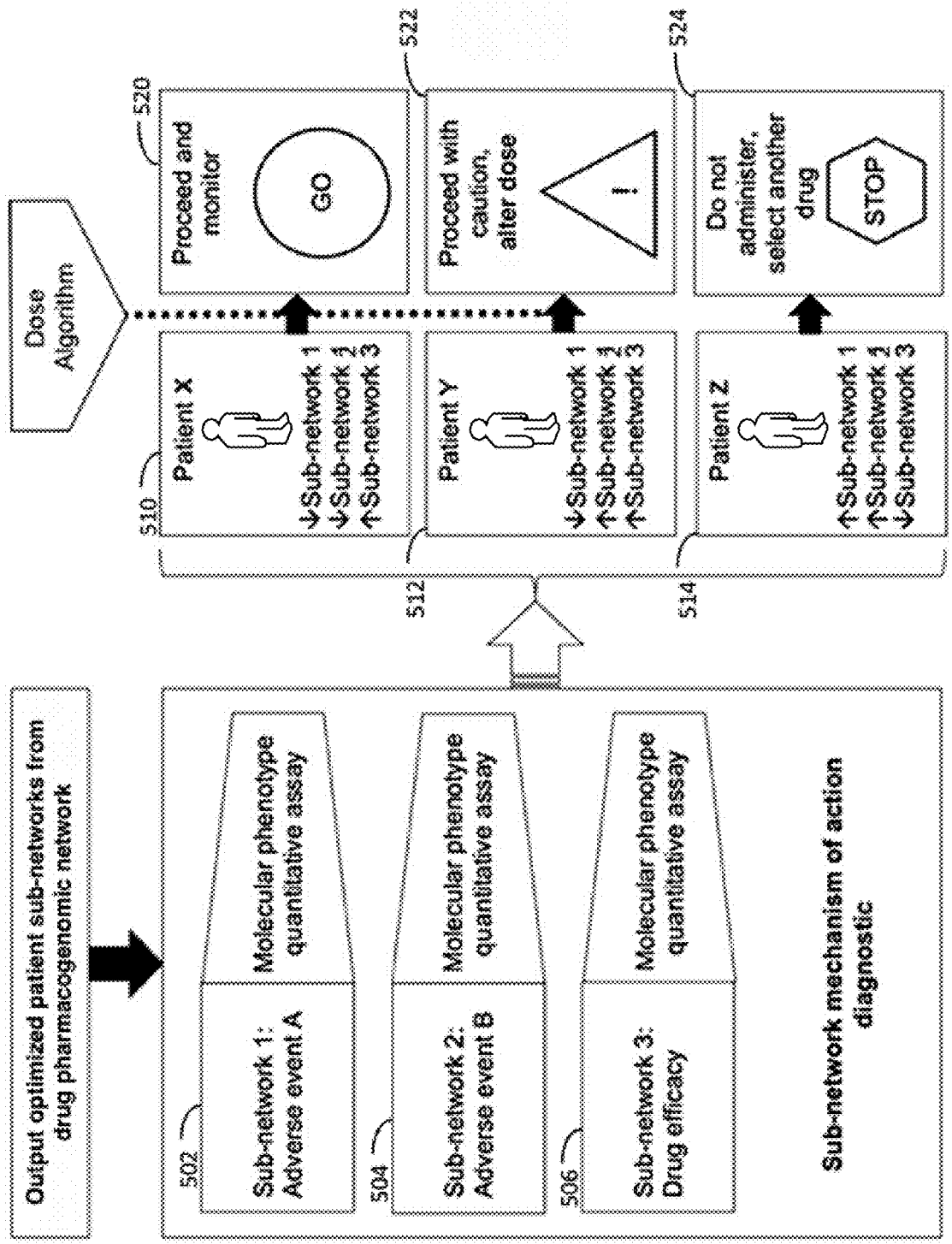
FIG. 5 illustrates a flow diagram representing an exemplary method for using efficacy and adverse event sub-networks derived from an individual patient's pharmacogenomic network to prescribe a given drug at a given dose safely, proceed with caution, or to stop recommendation to prescribe using molecular phenotype quantitative assays generated from the drug's sub-networks.

For example, as shown in FIG. 5, the drug and dose decision server 102 compares the patient's efficacy and adverse event sub-networks for a psychotropic drug of interest to reference efficacy and adverse event sub-networks for the psychotropic drug of interest. In this example, reference sub-network 1 (ref. no. 502) and reference sub-network 2 (ref. no. 504) are adverse event sub-networks, while reference sub-network 3 (ref. no. 506) is an efficacy sub-network. Patient X's sub-networks 510 are dissimilar from the adverse event sub-networks (reference sub-networks 1 and 2 (ref. nos. 502, 504)) and similar to the efficacy sub-network (reference sub-network 3 (ref. no. 506)). Accordingly, the drug and dose decision server 102 determines that the psychotropic drug of interest should be administered to the patient 520. Patient Y's sub-networks 512 are dissimilar from one of the adverse event sub-networks (reference sub-network 1 (ref. no. 502)) and similar to the other adverse event sub-network and the efficacy sub-network (reference sub-networks 2 and 3 (ref. nos. 504, 506)). Due to the adverse events in sub-network 2 (ref. no. 504), the drug and dose decision server 102 determines that the psychotropic drug of interest should be administered to the patient but with a reduced dosage 522. Patient Z's sub-networks 514 are similar to both adverse event sub-networks (reference sub-networks 1 and 2 (ref. nos. 502, 504)) and dissimilar from the efficacy sub-network (reference sub-network 3 (ref. no. 506)), and thus, the drug and dose decision server 102 determines not to administer the psychotropic drug of interest to the patient 524.

FIG. 5 provides examples of how bioinformatics analytics can be used in matching a drug's reference set of antidepressant efficacy versus adverse event signatures from the gene set optimizer with those of an input patient biosample. In FIG. 5, patient X can be administered ketamine based on the match of antidepressant efficacy from sub-network 2 of the reference pharmacogenomic network and reduced match to sub-network 3 of adverse events to antidepressant efficacy from the pharmacogenomic network that will be experienced by the individual. However, in patient Z, since this individual harbors some of the disease risk SNPs from GWAS found in sub-networks of the pharmacogenomic network, patient Z's ketamine dose should be adjusted.

Figure 6:
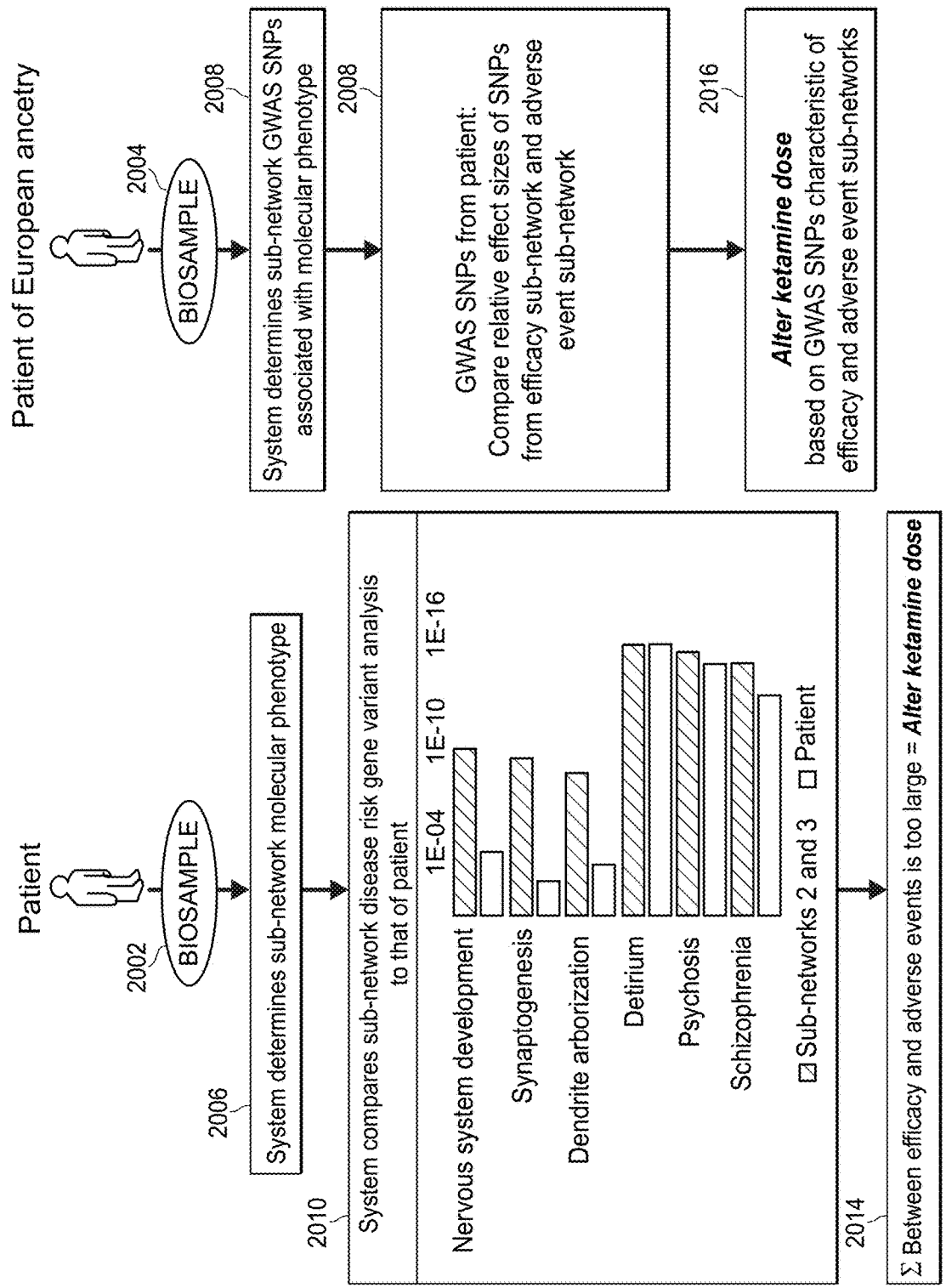
FIG. 6 illustrates 2 different methods based on the post hoc bioinformatics analysis and annotation of disease risk SNPs from GWAS to determine that the patient of a specific ancestry should receive ketamine based on disease gene risk variant analysis and the presence of disease risk SNPs associated with ketamine's adverse event sub-network 3 and efficacy sub-network 2.

FIG. 6 illustrates how two different methods may be derived from and based on the post hoc bioinformatics analysis or annotation of disease risk SNPs from GWAS to determine that the patient should not receive ketamine based on disease gene risk variant analysis and the presence of disease risk SNPs associated with ketamine's adverse event sub-network and efficacy sub-network of the pharmacogenomic drug network for ketamine. These simple and preliminary methods may be used to initially screen a patient as to potential negative consequences of ketamine administration.

Biosamples 2002, 2004 are collected from patient A and patient B. Patient A's biosample 2002 is analyzed to perform pharmacodynamic SNPs targeting as inputs into pharmacogenomic network and sub-network profiling to determine efficacy and adverse event sub-networks for Patient A (block 2006). Patient B's biosample 2004 is analyzed to identify pharmacokinetic SNPs associated with ketamine response (block 2008). Patient A's efficacy and adverse event sub-networks are then compared to a reference pharmacogenomic network and reference efficacy and adverse event sub-networks for ketamine (block 2010). Patient B's SNPs are compared to SNPs included in reference pharmacogenomic network and reference efficacy and adverse event sub-networks for ketamine (block 2012). In FIG. 6, patient A dose must be adjusted prior to administration of ketamine based on the matching of ketamine sub-network mediating adverse events to that of antidepressant efficacy from the pharmacogenomic network that will be experienced by the individual and the reduced match of antidepressant efficacy sub-network of the reference pharmacogenomic network (block 2014). Also, in patient B, since this individual harbors many of the disease risk SNPs from GWAS found in sub-networks of the pharmacogenomic network, the dose of ketamine administered to patient B should be adjusted (block 2016).

Figure 7:
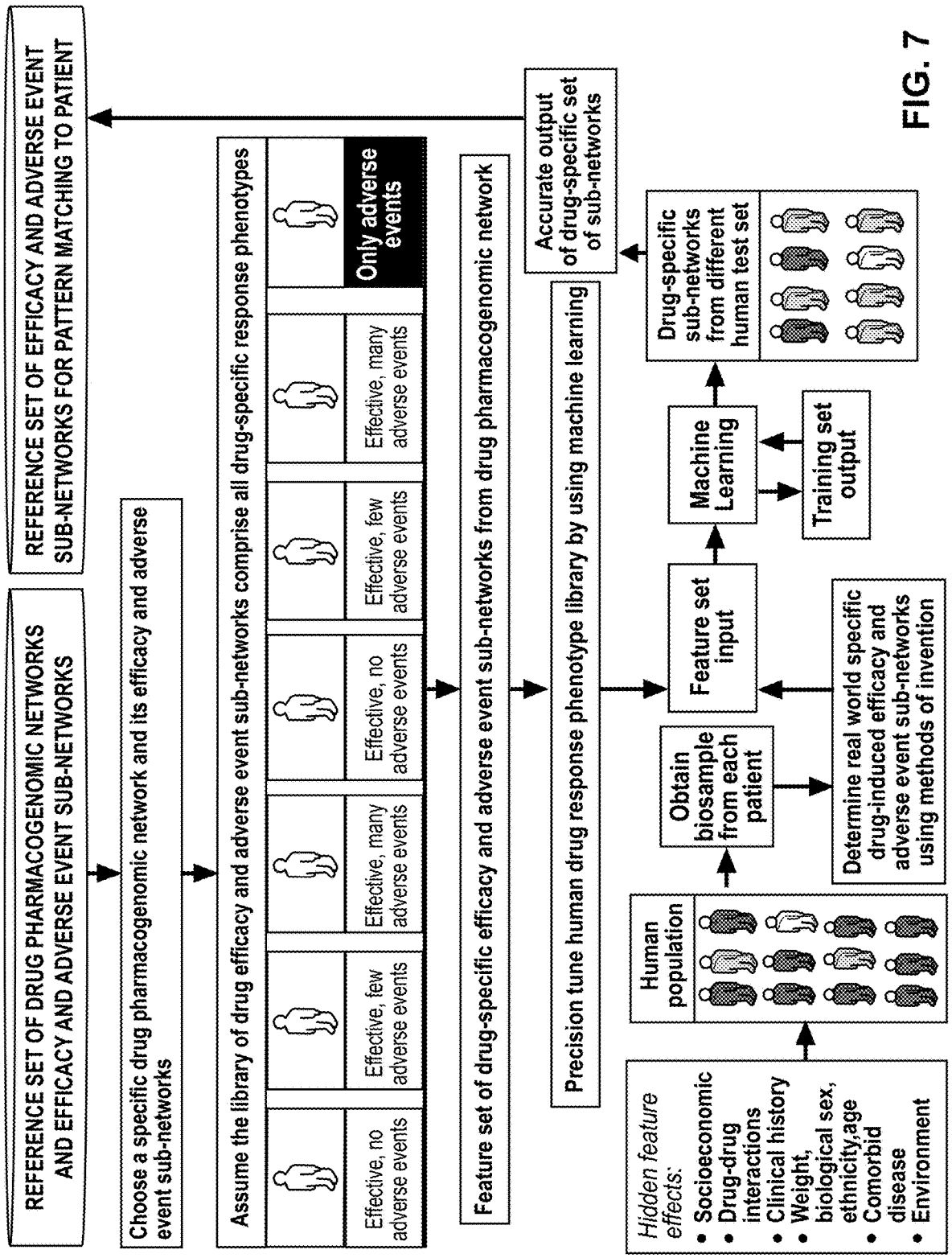
FIG. 7 illustrates how fine-tuning of a range of sub-network types spanning the range of human drug response phenotypes is accomplished using machine learning against a model created from a highly heterogenous set of hierarchal biomedical and biological data types and elements as a compared with that of the patient input sample data after a particular drug is chosen from a database of reference set of drug pharmacogenomic networks and their constituent sub-networks.

FIG. 7 illustrates a comprehensive strategy in which a library spanning human drug response cohort phenotypes stored in a reference database are used to make an initial "go or no-go" decision about whether ketamine should be administered or not for a specific patient, and how other clinical data from a particular patient may be fine-tuned to make an informed clinical decision.

Figure 8:
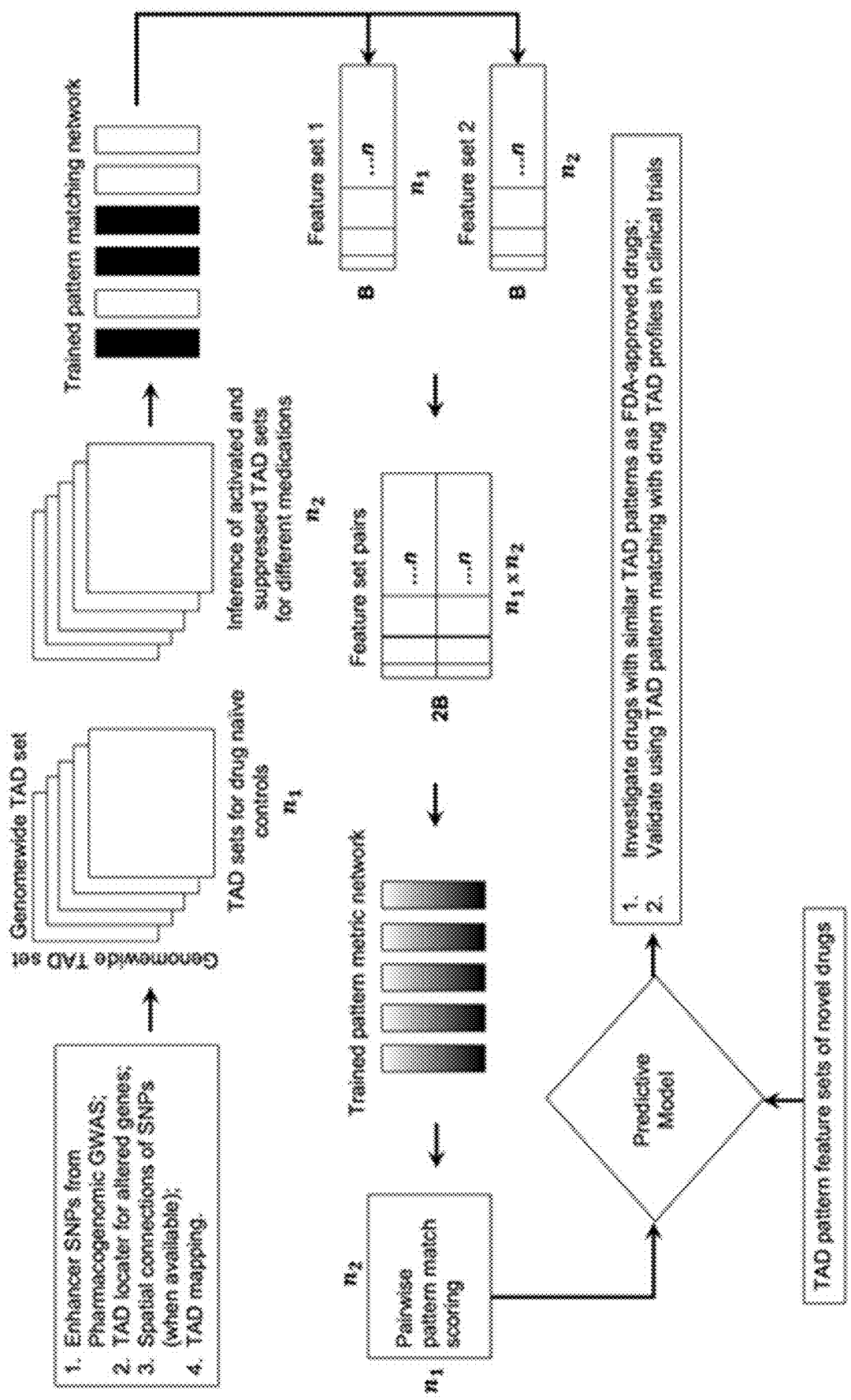
FIG. 8 illustrates a flow diagram of an exemplary method for using similarity scores to match a patient's drug pharmacodynamic efficacy and adverse events to that of a reference drug pharmacogenomic network for novel pharmacodynamic target discovery using TAD matrix mapping and deep learning based on computer vision algorithms to allow for TAD patterns to be used to investigate drug similarity and/or use TAD matching methods in clinical trial investigating drug TAD profiles.

FIG. 8 illustrates a flow diagram that uses well known pattern matching algorithms from deep learning in computer vision to use similarity scores to match a patient's drug efficacy and adverse events to that of a reference drug pharmacogenomic network. FIG. 8 also illustrates how this strategy may be used for the discovery of novel, similar drugs.

Figure 9A:
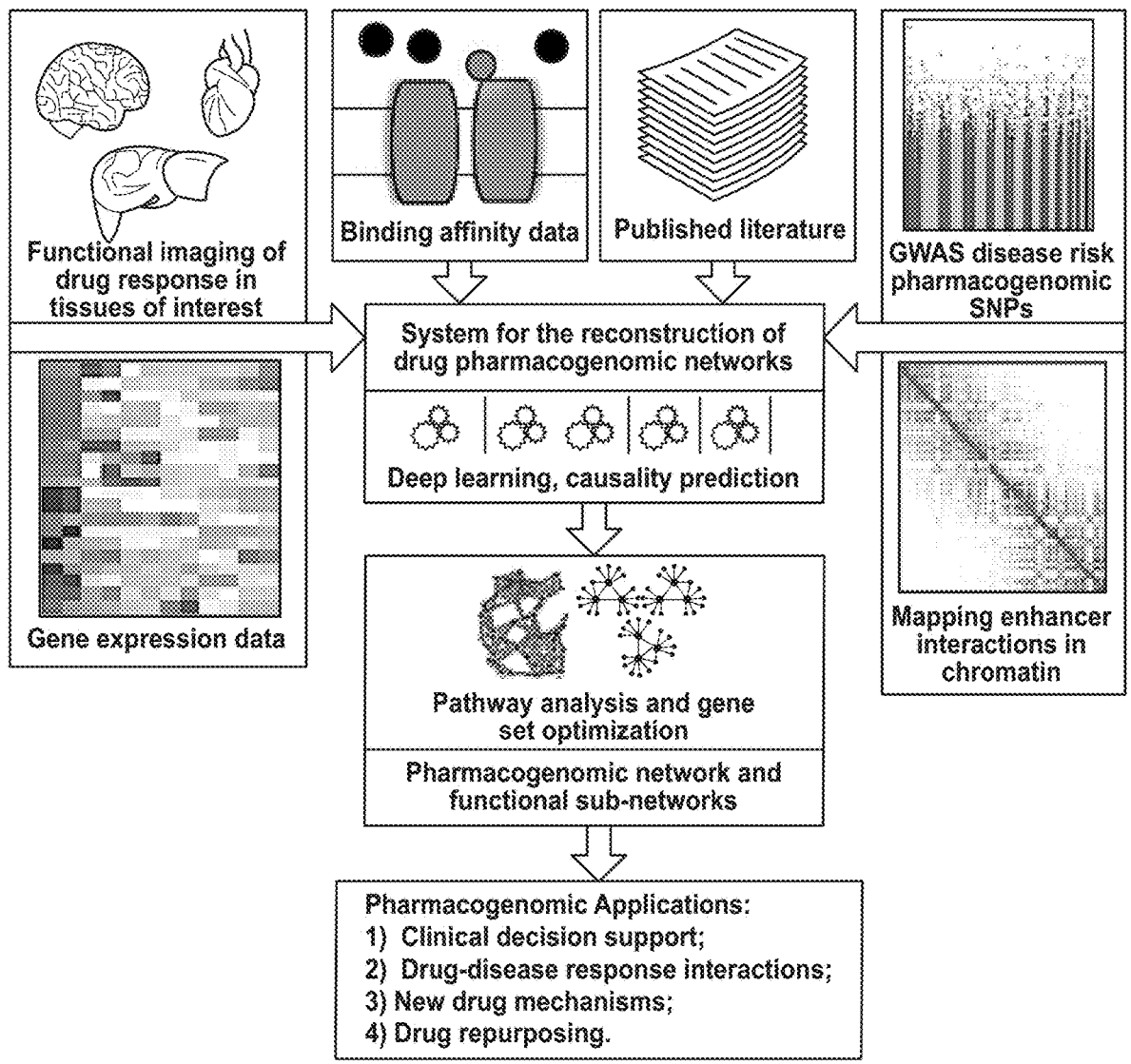
FIG. 9A illustrates an exemplary model for how the system integrates heterogeneous hierarchal biomedical and biological data and processes these multi-scale data using machine learning and deep learning for pharmacogenomic network topology and sub-network reconstruction. This strategy for mapping drug networks provides insight into the mechanistic on- and off-target effects. Using the discovered pharmacogenomic network topologies provides the basis for advanced pharmacogenomics decision support, laying a foundation for subsequent preclinical and clinical studies to refine this capability, which can also be used for drug mechanism discovery and drug repurposing prediction.
Figure 9B:
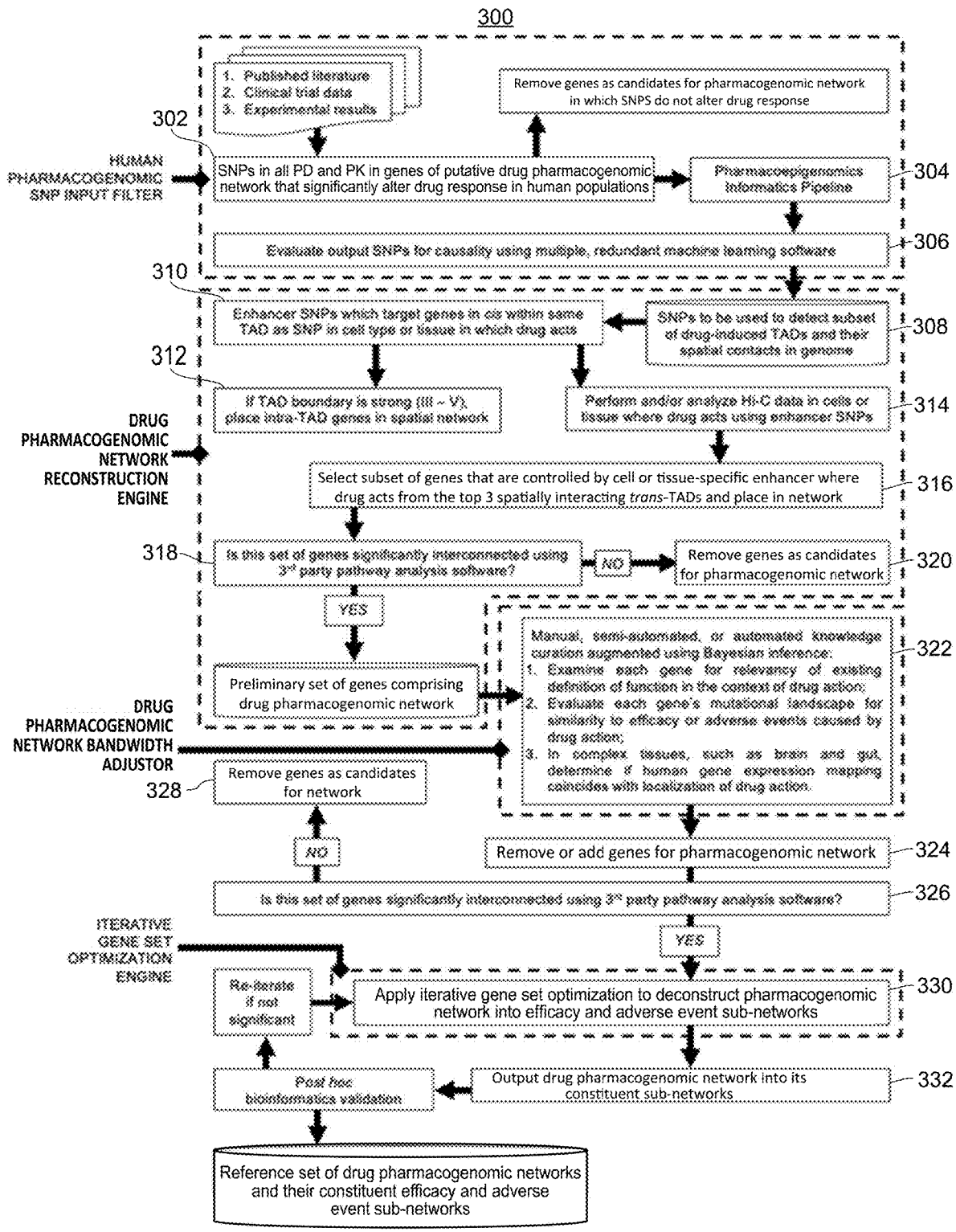
FIG. 9B illustrates a flow diagram representing a method for generating a reconstructed drug pharmacogenomic network and corresponding sub-networks for a drug of interest, including the human pharmacogenomic SNP input filter, the drug spatial network reconstruction engine, and the iterative gene set optimization engine. Reference sets of these drug pharmacogenomic networks, drug efficacy, and drug adverse event information can also be created.

FIG. 9A illustrates an overview of the integrative, multi-scale data analysis used in the system. FIG. 9B illustrates a flow diagram representing an exemplary method for generating a reconstructed drug pharmacogenomic network and corresponding sub-networks for a drug of interest, including the human pharmacogenomic SNP input filter, the drug pharmacogenomic network reconstruction engine, and the iterative gene set optimization engine.

As described above, biosample measurement includes pharmacodynamic SNP targeting as inputs into pharmacogenomic network and sub-network profiling, which is deterministic of both efficacy and adverse events as analyzed using the pharmacogenomic genome classifier and pharmacodynamic sub-network profiling systems. The patient's sub-networks for a particular drug of interest are then compared to a reference pharmacogenomic network and its constituent sub-networks for the drug of interest. FIG. 9B illustrates a method 300 for identifying a reference pharmacogenomic network and constituent sub-networks for a particular drug of interest, such as ketamine. In some embodiments, the drug and dose decision server 102 executes the method 300 to identify the pharmacogenomic network and constituent sub-networks for a particular drug of interest and stores the pharmacogenomic network and constituent sub-networks in the reference pharmacogenomic network database 154. In other embodiments, the method 300 is executed by another computing device and the output of the method is provided to the drug and dose decision server 102 and stored in the reference pharmacogenomic network database 154.

Selection of SNPs

In any event, at block 302, SNPs are obtained from human clinical studies that have demonstrated significant association with response and adverse events to the drug of interest. Since the location of a SNP associated with the trait under study has been, in most cases, inaccurately assigned to the nearest gene or nearby candidate gene in the published literature and GWAS per the linear sequence of the reference human genome assembly, accurate localization using imputation and annotation techniques are used to determine the actual location of the reported SNP.

New research has several important implications for drug pharmacogenomic network identification. First, new drug target mechanisms can be identified by collecting pharmacogenomic network outputs in a training set through the use of computer vision-based TAD matching using deep learning (machine learning) and validation using correspondence to known drug-induced genome-wide TAD matrices. Second, the clustering of new drug target mechanisms in previously defined but incompletely informed biological pathways will increase the probability of success. Third, insight gained using three-dimensional (3D) genome architecture to determine drug targets from pharmacogenomic GWAS will lead to a next generation of drug candidates and greatly enhance the accuracy of pharmacogenomic clinical decision support diagnostics.

At block 304, pharmacodynamics, pharmacokinetic, and other SNPs are evaluated using a pharmacogenomics informatics pipeline. The pharmacogenomics informatics pipeline uses lead SNPs reported from GWAS and candidate gene studies to find genetically linked permissive candidate SNPs using TAD boundary instead of measures of linkage disequilibrium. These SNPs are evaluated with two separate workflows: the enhancer regulatory workflow for regulatory SNPs and the coding SNP workflow. The enhancer regulatory SNP workflow evaluates the permissive candidate SNPs in disease-relevant tissues for DNA methylation, transcription factor binding, histone marks, DNase I hypersensitivity, chromatin state, quantitative trait loci (QTLs) and transcription factor binding site disruption using tissue-specific omics datasets. The coding SNP workflow finds common nonsynonymous coding SNPs within the pool of permissive candidate SNPs, which are then examined for histone modifications ruling out exon-containing enhancer SNPs. Both sets of SNPs are mapped back to their TADs and host genes and screened for expression in relevant tissues. The final output SNPs are then evaluated using open source machine learning algorithms to determine if the SNP is causal or not (block 306), and the causal variants are kept for further analysis in the workflow (block 308). Exon SNPs are also evaluated as splice donors or splice acceptors using the Altrans algorithm. If they are found to be involved in alternative splicing, they are stored as such.

Use of Casual Enhancer SNPs for Interrogation

At block 310, enhancer SNPs are used as probes to determine target genes within the same TAD as the enhancer is located, and to determine pharmacogenomic trans-interactions with other TADs using Hi-C chromosome conformation capture and ChIA-PET datasets (block 314) generated from cell types and tissues in which the drug of interest acts. Genes, which herein includes other functional elements such as long non-coding RNAs, are located within the same TADs that are targets of the enhancer that significantly alters drug response in human populations are selected for the drug pharmacogenomic network, if the TADs have strong boundaries as predicted by the amount of bound CTCF and significant association with super-enhancers (block 312). In the TADs that comprise the top 3 statistically significant pharmacogenomic contacts of the first set of pharmacogenomic TADs within the same cell and/or tissue type in which the drug of interest acts are then evaluated, and genes within these "trans-TADs" are chosen if they are controlled by the same cell and/or tissue-specific enhancers in which the drug of interest acts (block 316).

At block 318, the combined set of genes are evaluated for inter-connectivity, where the combined set of genes are selected from the first set of TADs that harbor the pharmacogenomic SNPs and the genes selected from the "trans-TADs", comprising the genes controlled in concert with the first set of TAD genes. For example, third-party software may be utilized, such as Ingenuity Pathway Analysis™, for examination of connectivity of the combined set of genes. Using Fisher's right-sided exact test, if there exists significant interconnectivity within the combined set of genes based on the published literature, then the genes are placed into the preliminary set of genes that comprise the pharmacogenomic network for the drug of interest. Any genes not forming a connected network are discarded as non-candidate genes for the pharmacogenomic network (block 320).

Knowledge-Based Revision of the Preliminary Pharmacogenomic Network of Drug-Specific Interconnected Genes Then at block 322, manual, semi-automated or automated curation, or a combination thereof, is performed on each gene in this gene set comprising the preliminary drug pharmacogenomic network to remove genes whose function are not related to the drug of interest in the cell and/or tissue types in which it acts, or to add other genes not part of this preliminary set of the drug pharmacogenomic network should be added to the set if they are judged to be specifically impacted by the drug of interest in the cell and/or tissue types in which they act. The interrogation steps include definition of an individual gene's function, the phenotypic consequences of mutational impairment of the gene, and the human cells and tissues in which the gene is expressed, to see if it can become a candidate for membership in the pharmacogenomic network of the specific drug of interest.

In one embodiment, these determinations can be made using a manual, semi-automated, or automated strategy, combining curation of each gene, its mutational profile, and its localization of expression within human tissues. These are enabled by a variety of web-based search tools, including gene definitions, genome browser annotations, the GWAS catalogue and other bioinformatics resources. For example, application programming interfaces (APIs) may have executables written in R, Python, PERL or other programing languages to facilitate data access, data cleansing and data analysis. This embodiment is an enhanced model of manual curation but can become time limiting if there are many genes within a gene set of the drug pharmacogenomic networks or the gene subsets of the sub-networks, and especially in cases where functional genomic elements may include regulatory RNAs or functional RNAs such as long noncoding RNAs, or if the function of the genes are poorly understood. Listing and analysis of the mutational landscape of a given gene (±10 Kb upstream and downstream) is the easiest of the 3 interrogation steps to be performed because these databases are the most comprehensive. Other resources exist for the analysis of the tissue distribution of a gene's expression pattern. In cases where these patterns are compared to sites where the specific drug of interest acts, the results from imaging modalities may be analyzed including from radiological studies, light microscopic analysis in pathology and even more sophisticated methods. In some embodiments, this analysis is performed using machine learning techniques, such as neural networks.

In another embodiment, a Bayesian probabilistic classifier may be used, either based on machine learning or using Bayesian probabilistic computing. The automated methods can be used to reduce the complexity of data analyzed from disparate data resources in which a gene's function knowledge profile, its mutational landscape and its tissue expression mapping are inputs to a learning machine that has been trained on a number of such instances and tested independently on another set of instances for determination of accuracy. Predictive features selected by the trained neural network can be implemented on a support vector machine classifier to construct a gene's function and mutational prediction model, where subsequent machine states determine the adequacy of statistical fit to the drug pharmacogenomic network.

In some scenarios, machine learning is subject to overfitting, outputting false positives or false negatives. In another embodiment, semi-automated and naïve Bayesian classification may be performed using machine learning in parallel to sharpen the accuracy of the final output.

Knowledge-based curation may be performed with the following steps. First, the gene definition is examined from multiple databases to understand if it is specifically, but not generically, impacted by the drug of interest. In addition, the published literature, including text word strings containing the gene name or precursor gene name or equivalent protein name plus any function related to the drug of interest is evaluated following thorough internet searches using for example, Google Scholar™ and/or PubMed. These may include binding affinity studies which have reproducibly found molecules which bind with an affinity that is within 10-fold that of the affinity of which the drug of interest binds to the same pharmacodynamic target. Second, the drug and dose decision server 102 examines each gene for all mutations, including SNPs, variable number of tandem repeats, duplications and all other known mutational alterations, extending in linear sequence±10 kb from the transcription start site(s) and stop codon(s) of the gene as examined in a genome browser such as the UCSC genome browser or the Ensembl genome browser. If any of these mutations are found in either the published literature or sources such as unpublished clinical trial data, and they are involved in the action of the drug of interest, including efficacy, adverse events or first pass metabolism, then they are added to the preliminary set of genes comprising the pharmacogenomic network (block 324). Third, especially for complex tissues such as the brain, skin and the cardiovascular system, the drug and dose decision server 102 performs concordance mapping qualitatively to compare the expression of all genes in this final set to where the drug of interest exerts its action, if known. Genes whose expression does not match the pharmacodynamic substrate of the drug of interest are discarded (block 324). Finally, third-party software such as Ingenuity Pathway Analysis™ is used for examination of connectivity of this gene set (block 326). Using Fisher's right-sided exact test, if the drug and dose decision server 102 determines that there exists significant interconnectivity based on the published literature, then they are placed into the preliminary set of genes that comprise the pharmacogenomic network for the drug of interest. Any genes not forming a connected network are discarded as non-candidate genes for the drug pharmacogenomic network (block 328).

Iterative Gene Set Optimization

Figure 10:
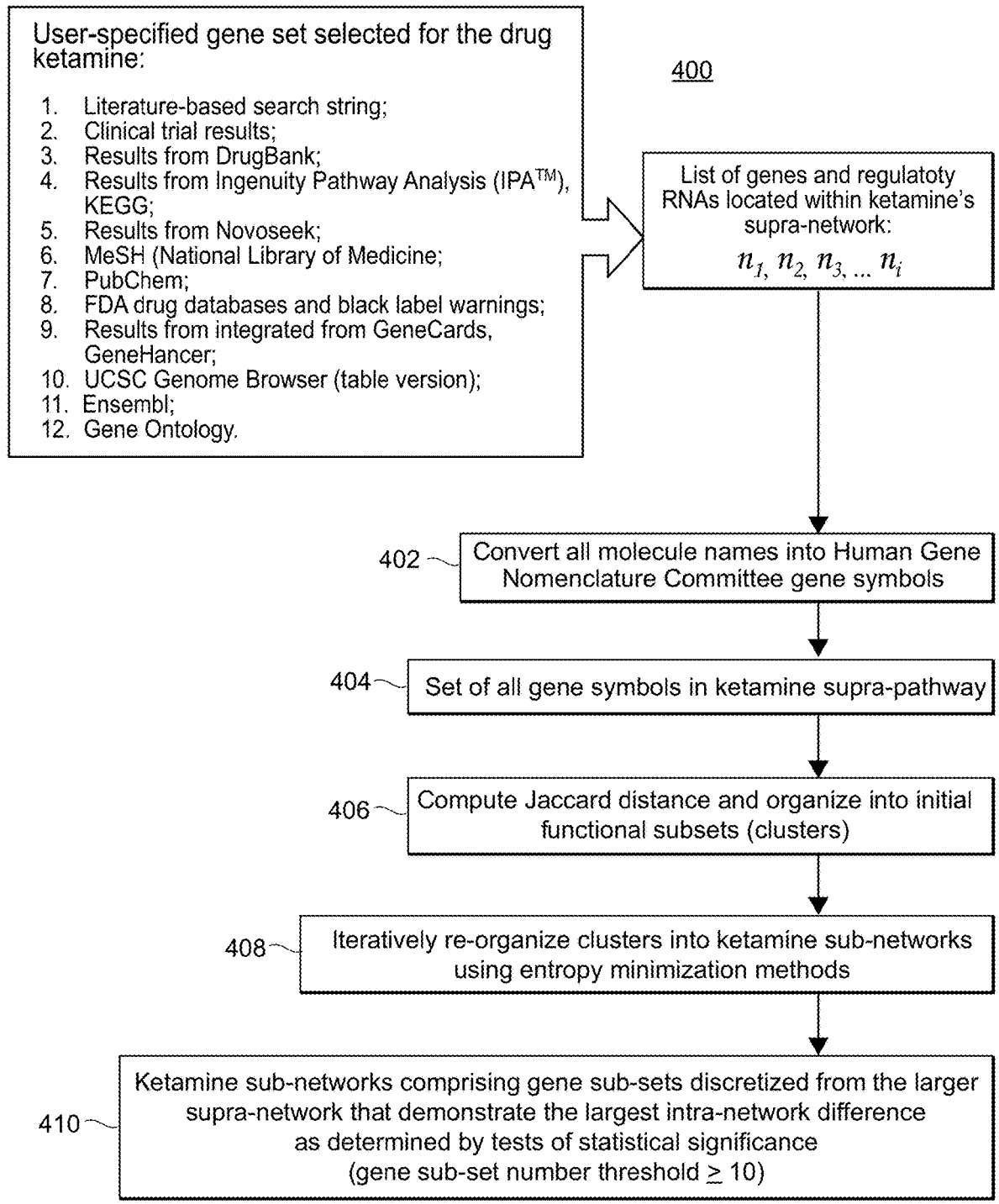
FIG. 10 illustrates a flow diagram representing an exemplary method for integrative drug-gene set optimization to construct a pharmacogenomic network and to determine into its sub-networks.

As shown at block 330, and in more detail in FIG. 10, iterative gene set optimization is performed on the identified set of candidate genes in the pharmacogenomic network for the particular drug of interest. An example method 400 for iterative gene set optimization to deconstruct a drug pharmacogenomic network into sub-networks is illustrated in the flow diagram of FIG. 10. Iterative gene set optimization may be performed to identify sub-networks of the drug pharmacogenomic network. More specifically, iterative gene set optimization includes converting all input molecule terms into gene or long non-coding RNA names from for example, the Human Gene Nomenclature Committee (HGNC) names (block 402) using their API. The iterative gene set optimization differs from gene set enrichment methods, by not only combining a variety of statistical methods, but also not acting in a hierarchal manner ranking genes as in threshold-dependent methods, and iterative gene set optimization does not rely on comparisons of experimental results, such as in whole-distribution tests. Instead, the iterative gene set optimization groups genes or long noncoding RNAs from the pharmacogenomics pharmacogenomic network (block 404) using the Jaccard distance to first measure the similarity between two genes or long noncoding RNAs based on the dissimilarity of user-selected terms, where the Jaccard distance is as the ratio of the size of the symmetric difference GeneAΔGeneB=A∩B−A∪B to the union (block 406). This is extensible into clusters of related dissimilar gene names. The drug and dose decision server 102 then automatically sorts these sets, or using user-defined numbers of clusters, into subsets of clustered subsets of functionally related genes using a minimal entropy sorting algorithm, such as the COOLCAT algorithm (block 408). Following gene subset optimization using entropy minimization, manual curation may be employed to assign efficacy, adverse event or functional mechanistic sub-networks based on known attributes of the drug's mechanism of actions under consideration (blocks 410, 412).

Post-Hoc Validation Using Third Party Bioinformatics Tools

For scientific validation of the deconstruction of the drug pharmacogenomic network into mechanistic sub-networks based on functional gene subset optimization, each drug pharmacogenomic network's sub-network is assessed post hoc for top Gene Ontology terms (molecular function and biological processes), top canonical pathways for example, as determined using other proprietary or open source pathway analysis software, disease risk gene variant analysis for example, as determined using other proprietary or open source pathway analysis software, and determination of upstream xenobiotic regulators using different bioinformatics resources (block 332). In addition, the GWAS catalogue of the European Bioinformatics Institute, the National Human Genome Research Institute, and the National Institutes of Health may be searched to find significant SNP-trait associations for each gene of the gene sets for each sub-network. By providing examples of SNPs from GWAS that are statistically significant, additional evidence may be provided that mutational impairment of the genes included in each sub-network provides insight into the normal, unimpaired function of the sub-network.

Figure 11:
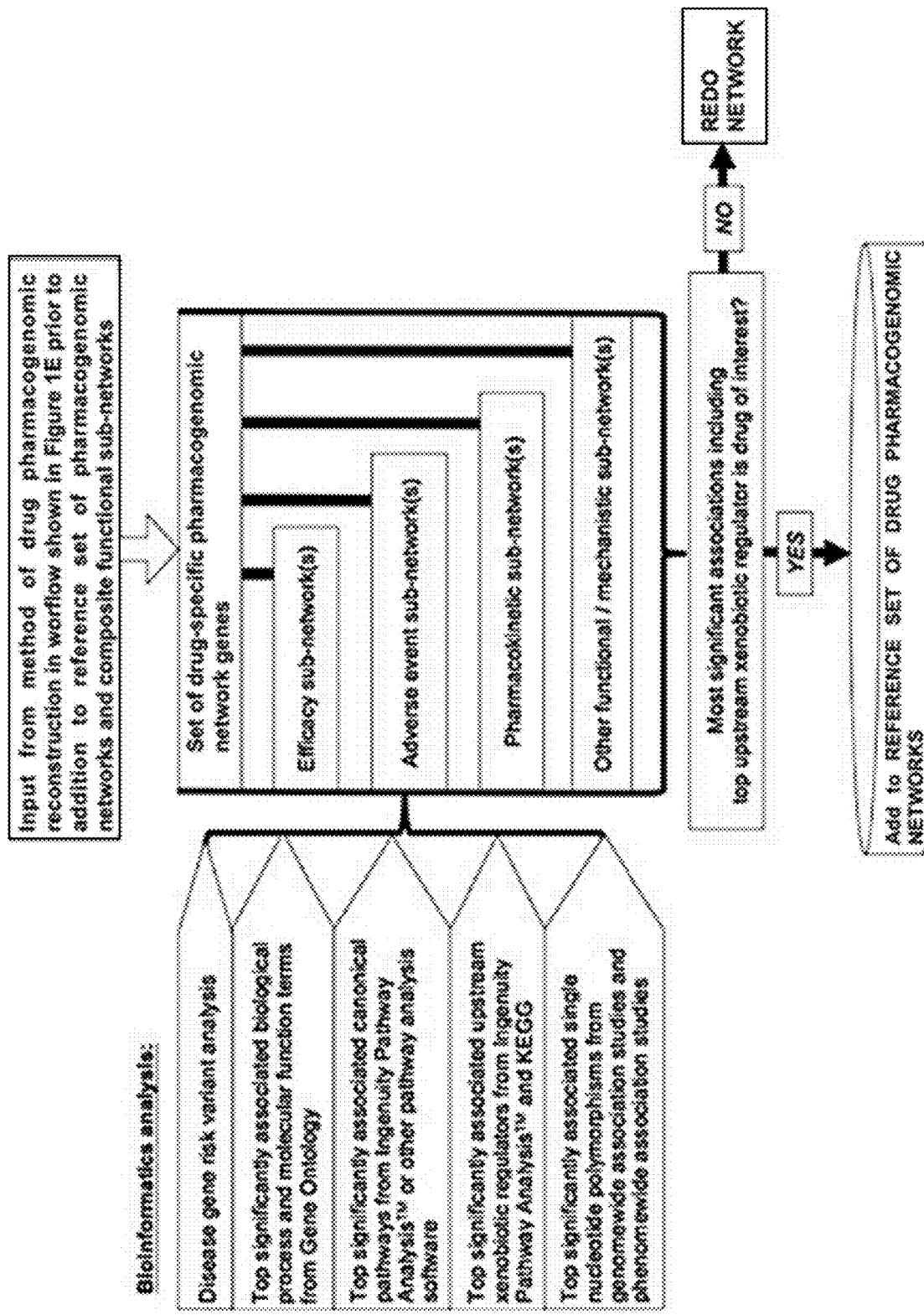
FIG. 11 illustrates a flow diagram for post hoc validation of a reconstructed drug pharmacogenomic network and sets of such networks using bioinformatics data/software and integrative pharmacoinformatics pipelines.

In some embodiments, after post hoc validation is performed, as shown in FIG. 11, the resulting pharmacogenomic network and constituent sub-networks for the particular drug of interest are stored for example, in the database 154 as shown in FIG. 1A.

For example, to map causal SNPs that discretize response to ketamine in human populations, their target genes within their TADs, and the pharmacogenomic contactome of these TADs, Hi-C chromosome conformation capture data may be used from publicly-available datasets that were mapped in an A735 astrocyte cell line, H1 neuronal cell line, SK-N-SH cell lines and in samples from a postmortem human brain.

Figure 12:
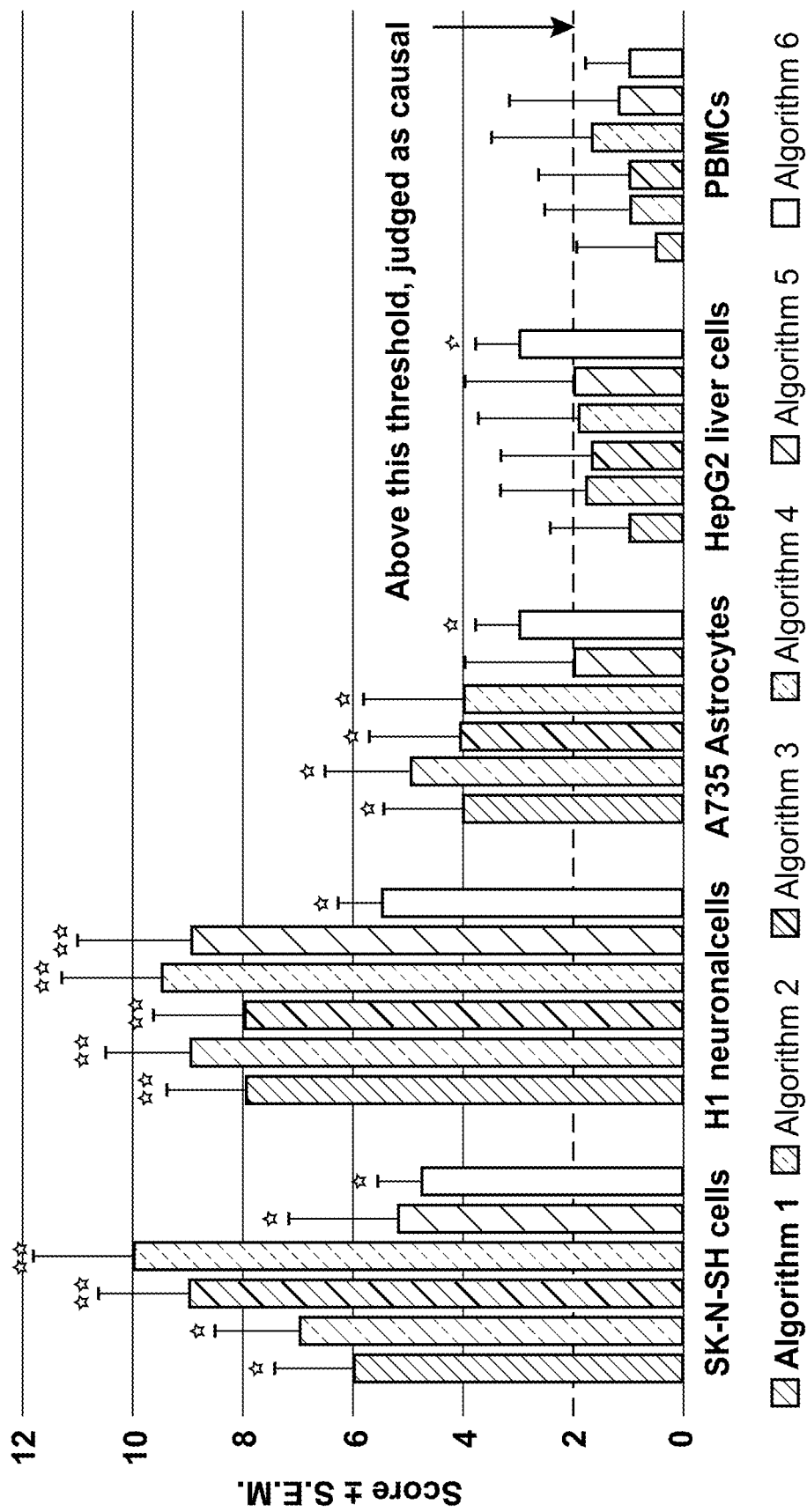
FIG. 12 illustrates an example of a comparison of the results of significance testing of the SNP rs12967143-G, an intragenic enhancer located in the TCF4 gene, versus other GWAS SNPs as described using the numerical output from six different machine learning algorithms used in the analysis and among various neural and non-neural cell types.

FIG. 12 shows an example of a comparison of the results of eight different algorithms testing the predicted causality of the GWAS SNP rs12967143-G, an intragenic enhancer located in the TCF4 gene, a member of the ketamine pharmacogenomic efficacy sub-network, versus other GWAS SNPs, as described using the numerical output from the machine learning algorithms used in the analysis ($*p \leq 0.05$; $**p \leq 0.01$; ANOVA).

Using H-GREEN, a user-adjustable binning software package, the trans-TADs are mapped that overlap between different data sources. The top 3 trans-TAD pharmacogenomic contacts genome-wide may be selected for each originating causal SNP TAD locus. Using prior knowledge of ketamine as an anesthetic and analgesic, and in more recent studies and clinical trials of ketamine and other glutamate receptor modulators as antidepressants, the methods described herein may be used to score the top trans-TAD contacts, and for each causal SNP, the top 3 may be selected for inclusion in the pharmacogenomic network. The recent availability of databases of validated enhancers and their targets may be used for both originating and targeted TADs in this workflow to reconstruct the ketamine pharmacogenomic network.

The intra-TAD and trans-TAD gene sets may serve as seeds to initiate pathway analysis. Filters and thresholds may be applied that eliminate genes expressed in the cell types, neurons and astrocytes, and in brain regions where ketamine exerts it mechanism(s) of action. These do not just include PD genes, but also PK genes, the latter which have recently been shown to be expressed at high levels in relevant human brain regions where ketamine acts, and in the case of the CYP2B6 gene, are induced by this psychotropic drug to much higher levels of expression than in the liver, gastrointestinal tract or kidney.

Following output of the automated pathway analysis, the drug pharmacogenomic network gene set is evaluated for plausibility, and genes may be added to the pathway that were not selected by the pathway analysis program. From earlier studies of binding affinities using methods in molecular pharmacology, genes are added back whose products exhibit within a 10-fold affinity of the racemic R, S-ketamine or the enantiomers to the NMDAR, as well as demonstrating molecular inter-connectivity. Other expression studies and research of the metabolism of ketamine may yield additional genes that are added back to the ketamine pharmacogenomic network.

The ketamine pharmacogenomic network is analyzed by gene set optimization into 3 sub-networks, of which 2 are significantly different sub-sets of genes and regulatory RNAs using iterative analysis. The 3 sub-networks include: (1) antidepressant efficacy and neuroplasticity, (2) glutamate receptor signaling, chromatin remodeling, and adverse events, and (3) pharmacokinetics and hormonal regulation associated with the drug. The second sub-network (2) glutamate receptor signaling, chromatin remodeling, and adverse events may include two separate sub-networks: a chromatin remodeling sub-network and a drug pharmacodynamics adverse events sub-network. To understand and validate the pharmacogenomic network and its mechanistic sub-networks, four types of additional analyses are performed. First, genes in the pharmacogenomic network and in each sub-network are interrogated for the presence of enhancer SNPs that are associated with pertinent traits in GWAS. Second, pathway enrichment including biological processes and molecular function are performed using the Gene Ontology standard to determine the most significant top pathways for these gene sets. Third, disease gene risk variant analysis is performed, which analyzes each gene super-set and subset for significance of the entire mutational contribution of these sets in humans for appropriate assignment to both the parent pathway and its constituent sub-networks and assigns the top diseases for super-set and sub-network set (most significant, Fisher's exact test). Fourth, the top (most significant, Fisher's exact test) xenobiotic drug that regulates the super-set of genes comprising the pharmacogenomic network is determined. In the last case, the pharmacogenomic network set of genes should be regulated by the drug that mediates the mechanism of the pharmacogenomic network, but for some of the sub-networks, depending on the mechanistic attributes of that network, drugs more relevant to that specific sub-network of the pharmacogenomic network mechanisms may be most significantly associated.

FIG. 13 shows the top Gene Ontology terms of the 2 significantly different ketamine pharmacogenomic sub-networks in the human brain. More specifically; FIG. 13A shows the sub-network that mediates efficacy and neuroplasticity. FIG. 13B shows the ketamine sub-network that mediates glutamate receptor signaling and adverse events in the human CNS.

Figure 14A:
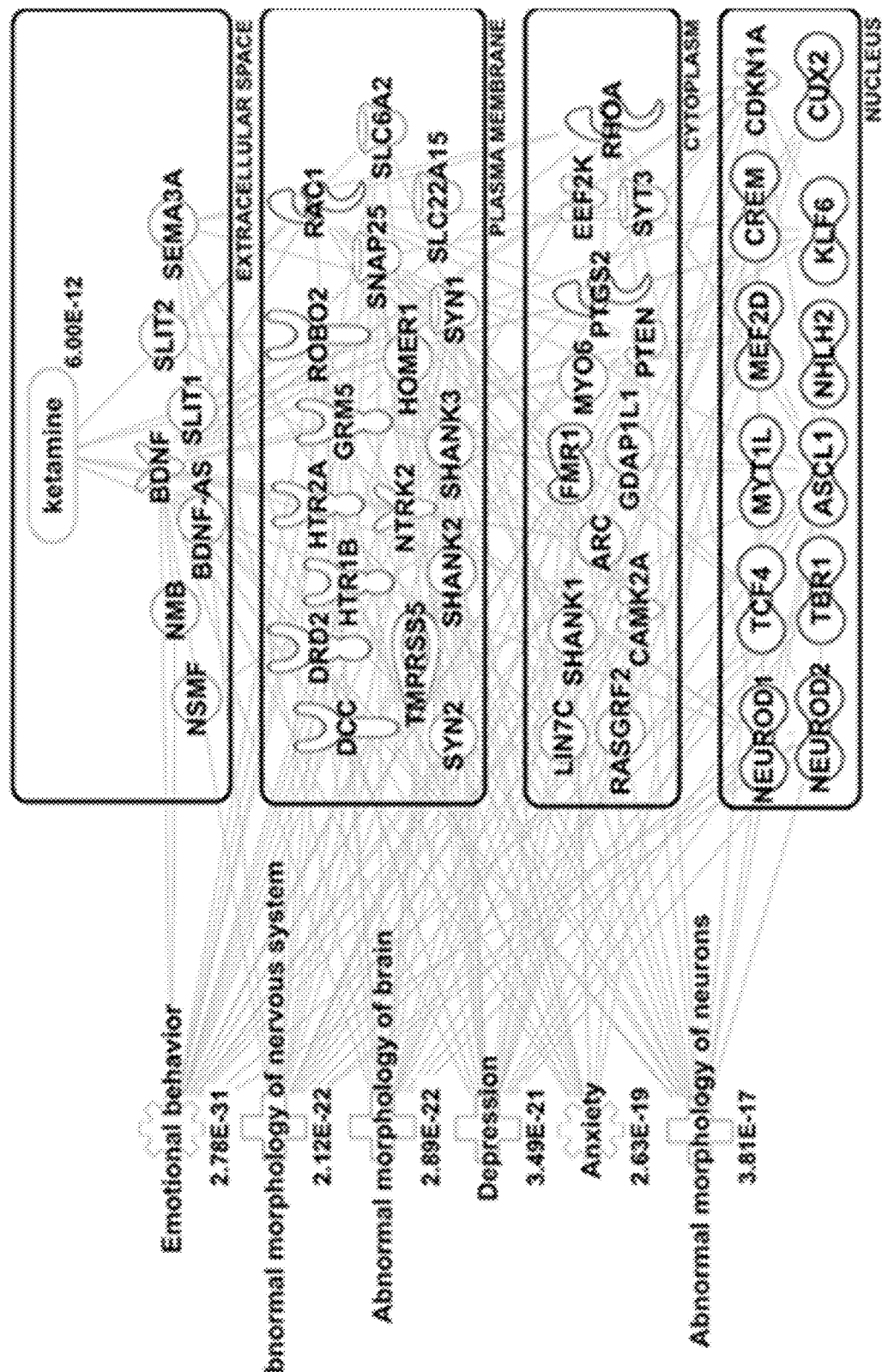
FIG. 14A illustrates graphical depictions of the ketamine pharmacogenomic sub-network in the human brain that mediates efficacy and neuroplasticity, and the diseases and conditions that are associated with efficacy and neuroplasticity.
Figure 14B:
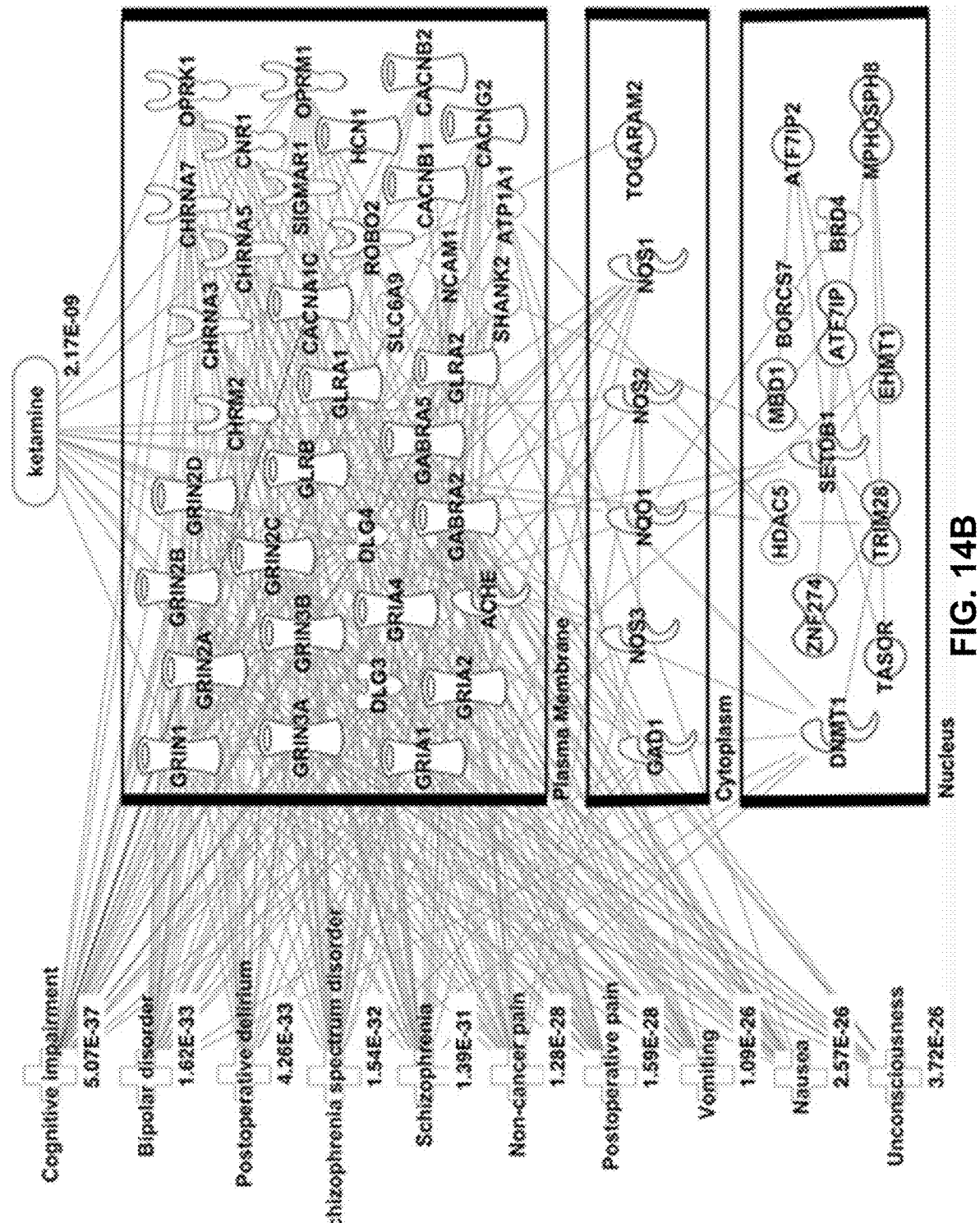
FIG. 14B illustrates graphical depictions of the ketamine pharmacogenomic sub-network in the human brain that mediates glutamate receptor signaling and adverse events in the human brain, and the diseases and conditions that are associated with this signaling and these adverse events.

FIG. 14A illustrates graphical depictions of the ketamine pharmacogenomic sub-network in the human brain that mediates efficacy and neuroplasticity. FIG. 14B illustrates graphical depictions of the ketamine pharmacogenomic sub-network in the human brain that mediates glutamate receptor signaling and adverse events in the human brain. More specifically, as shown in FIGS. 14A and 15, the genes and regulatory RNAs located in the ketamine efficacy and neuroplasticity sub-network include one or more of: Activity regulated cytoskeleton associated protein (ARC) gene, Achaete-Scute family bHLH transcription factor 1 (ASCL1) gene, Brain derived neurotrophic factor (BDNF) gene, BDNF antisense RNA (BDNF-AS) gene, Calcium/calmodulin dependent protein kinase II alpha (CAMK2A) gene, Cyclin dependent kinase inhibitor 1A (CDKN1A) gene, cAMP responsive element modulator (CREM) gene, Cut like homeobox 2 (CUX2) gene, DCC netrin 1 receptor (DCC) gene, Dopamine receptor D2 (DRD2) gene, Eukaryotic translation elongation factor 2 kinase (EEF2K) gene, Fragile X mental retardation 1 (FMR1) gene, Ganglioside induced differentiation associated protein 1 like 1 (GDAP1L1) gene, Glutamate metabotropic receptor 5 (GRM5) gene, Homer scaffold protein 1 (HOMER1) gene, 5-hydroxytryptamine receptor 1B (HTR1B) gene, 5-hydroxytryptamine receptor 2A (HTR2A) gene, Kruppel like factor 6 (KLF6) gene, Lin-7 homolog C, crumbs cell polarity complex component (LIN7C) long noncoding RNA, LOC105379109 long noncoding RNA, Myocyte enhancer factor 2D (MEF2D) gene, Myosin VI (MYO6) gene, Myelin transcription factor 1 like (MYT1L) gene, Neuronal differentiation 1 (NEUROD1) gene, Neuronal differentiation 2 (NEUROD2) gene, Nescient helix-loop-helix 2 (NHLH2) gene, Neuromedin B (NM8) gene, NMDA receptor synaptonuclear signaling and neuronal migration factor (NSMF) gene, Neurotrophic receptor tyrosine kinase 2 (NTRK2) gene, phosphatase and tensin homolog (PTEN) gene, Prostaglandin-endoperoxide synthase 2 (PTGS2) gene, Rac family small GTPase 1 (RAC1) gene, Ras protein specific guanine nucleotide releasing factor 2 (RASGRF2) gene, Ras homolog family member A (RHOA) gene, Roundabout guidance receptor 2 (R0802) gene, RP11_360A181 long noncoding RNA, Semaphorin 3A (SEMA3A) gene, SH3 and multiple ankyrin repeat domains 1 (SHANK1) gene, SH3 and multiple ankyrin repeat domains 2 (SHANK2) gene, SH3 and multiple ankyrin repeat domains 3 (SHANKS) gene, Solute carrier family 22 member 15 (SLC22A15) gene, Solute carrier family 6 member 2 (SLC6A2) gene, Slit guidance ligand 1 (SLIT1) gene, Slit guidance ligand 2 (SLIT2) gene, Synaptosome associated protein 25 (SNAP25) gene, Synapsin I (SYN1) gene, Synapsin II (SYN2) gene, Synapsin III (SYN3) gene, T-box, brain 1 (TBR1) gene, or Transcription factor 4 (TCF4) gene.

Also, as shown in FIGS. 14B and 16, the genes and regulatory RNAs located in the ketamine glutamate receptor signaling and adverse event sub-network include one or more of: Acetylcholinesterase (ACHE) gene, Activating transcription factor 7 interacting protein (ATF7IP) gene, Activating transcription factor 7 interacting protein 2 (ATF7IP2) gene, ATPase Na+/K+ Transporting Subunit Alpha 1 (ATP1A1) gene, BLOC-1 related complex unit 7 (BORCS7) gene, Bromodomain containing 4 (BRD4) gene, Calcium voltage-gated channel subunit alpha1 C (CACNA1C) gene, Calcium voltage-gated channel auxiliary subunit beta 1 (CACNB1) gene, Calcium voltage-gated channel auxiliary subunit beta 2 (CACNB2) gene, Calcium voltage-gated channel auxiliary subunit gamma 2 (CACNG2) gene, Cholinergic Receptor Muscarinic 2 (CHRM2) gene, Cholinergic Receptor Nicotinic Alpha 3 Subunit (CHRNA3) gene, Cholinergic Receptor Nicotinic Alpha 5 Subunit (CHRNA5) gene, Cholinergic Receptor Nicotinic Alpha 7 Subunit (CHRNA7) gene, Cannabinoid receptor 1 (CNR1) gene, Disks large homolog 3 (DLG3) gene, Disks large homolog 4 (DLG4) gene, DNA Methyltransferase 1 (DNMT1) gene, Euchromatic histone lysine methyltransferase 1 (EHMT1) gene, Gamma-aminobutyric acid type A receptor alpha2 subunit (GABRA2) gene, Gamma-aminobutyric acid type A receptor alpha5 subunit (GABRA5) gene, Glutamate decarboxylase 1 (GAD1) gene, Glycine receptor alpha 1 (GLRA1) gene, Glycine receptor alpha 2 (GLRA2) gene, Glycine receptor beta (GLRB) gene, Glutamate ionotropic receptor AMPA type subunit 1 (GRIA1) gene, Glutamate ionotropic receptor AMPA type subunit 2 (GRIA2) gene, Glutamate ionotropic receptor AMPA type subunit 4 (GRIA4) gene, Glutamate ionotropic receptor NMDA type subunit 1 (GRIN1) gene, Glutamate ionotropic receptor NMDA type subunit 2A (GRIN2A) gene, Glutamate ionotropic receptor NMDA type subunit 2B (GRIN2B) gene, Glutamate ionotropic receptor NMDA type subunit 2C (GRIN2C) gene, Glutamate ionotropic receptor NMDA type subunit 2D (GRIN2D) gene, Glutamate ionotropic receptor NMDA type subunit 3A (GRIN3A) gene, Glutamate ionotropic receptor NMDA type subunit 3B (GRIN3B) gene, Hyperpolarization Activated Cyclic Nucleotide Gated Potassium Channel 1 (HCN1) gene, Histone deacetylase 5 (HDAC5) gene, Methyl-CpG binding domain protein 1 (MBD1) gene, M-Phase Phosphoprotein 8 (MPHOSPH8) gene, Neural cell adhesion molecule 1 (NCAM1) gene, Nitric acid synthase 1 (NOS1) gene, Nitric acid synthase 2 (NOS2) gene, Nitric acid synthase 3 (NOS3) gene, NAD(P)H quinone dehydrogenase 1 (NQO1) gene, Opioid receptor kappa 1 (OPRK1) gene, Opioid receptor mu 1 (OPRM1) gene, Roundabout guidance receptor 2 (ROBO2) gene, SET domain bifurcated 1 (SETD81) gene, SH3 and Multiple Ankyrin Repeat Domains 2 (SHANK2) gene, Sigma Non-Opioid Intracellular Receptor 1 (SIGMAR1) gene, Solute carrier family 6 member 9 (SLC6A9) gene, Transcription Activation Suppressor (TASOR) gene, TOG array regulator of axonemal microtubules 2 (TOGORAM2) gene, Tripartite Motif Containing 28 (TRIM28) gene, or Zinc Finger Protein 274 (ZNF274) gene.

As shown in FIG. 17, the genes and regulatory RNAs located in the pharmacokinetic enzymes and hormones sub-network include one or more of: Anaphase promoting complex subunit 2 (ANAPC2) gene, Cytochrome P450 family 2 subfamily A member 6 (CYP2A6) gene, Cytochrome P450 family 2 subfamily B member 6 (CYP2B6) gene, Cytochrome P450 family 3 subfamily A member 4 (CYP3A4) gene, Disks large homolog 4 (DLG4), Eukaryotic Elongation Factor 2 Kinase (EEF2K) gene, Estrogen Receptor 1 (ESR1) gene, Glutamate ionotropic receptor AMPA type subunit 1 (GRIA1) gene, Glutamate ionotropic receptor AMPA type subunit 4 (GRIA4) gene, Glutamate ionotropic receptor NMDA type subunit 1 (GRIN1) gene, Glutamate ionotropic receptor NMDA type subunit 2B (GRIN2B) gene, Myosin VI (MYO6) gene, Roundabout Guidance Receptor 2 (ROBO2) gene, SH3 and Multiple Ankyrin Repeat Domains 2 (SHANK2) gene, and Transcription Elongation Regulator 1 (TCERG1) gene.

Automated iterative gene set optimization of the psychotropic pharmacogenomic network into sub-networks may be user-limited to investigate other features of the pharmacogenomic network. As described above with reference to FIG. 10, the ketamine pharmacogenomic network is iteratively deconstructed until certain specific genes do not significantly associate with any sub-network or were associated with several sub-networks deconstructed from the drug pharmacogenomic network. The gene ESR1 encodes the nuclear hormone receptor for estrogen and it regulates the expression of several genes in the ketamine pharmacogenomic network. It is well known that estrogen greatly induces the CYP2B6 gene both in the human brain and elsewhere.

The learning architecture for training the pattern matching sub-networks includes pre-training the reference set (ref. no. 710). More specifically, at block 704, the drug and dose decision server 102 develops the patient's pattern matching sub-networks derived from the patient input biosample, and co-develops separate trained pattern metrics (block 712), which contain the features of the efficacy and adverse event sub-networks, to a joint feature representation metric. For determination of similarity to the reference set (blocks 706, 708), the two different pairs of reference-patient metrics include an accurate measurement of similarity and outputs similarity scores for each of the efficacy and adverse events (blocks 714, 716). At block 702, the biosample obtained from a patient, which may be a cheek swab, saliva, blood or urine sample, undergoes targeted enhancer SNP genotyping, as well as combined chromosome conformation capture and RNA-seq. Then at block 704, the drug and dose decision server 102 performs analysis necessary to build the input patient-specific map of efficacy and adverse event sub-networks for a specific drug of interest. These patient-specific, drug-induced sub-network patterns could be further processed using Bayesian probabilistic computing to fill in sparse or missing data. As a new patient enters as an input, the pretrained reference set of drug-specific efficacy and adverse event sub-networks for pattern matching is once again optimized for subsequent patients, producing a more accurate measure of pharmacogenomic variability among humans with enhanced clinical utility. This matching task assumes that patches go through the same feature encoding before computing and outputting a similarity score, greatly increasing efficiency while reducing computational requirements.

Each set of inputs (reference set (ref. no. 710) and patient set (ref. no. 720)) are thus constructed differently with feature set extraction and inference of sparse data using probabilistic computing based on Bayesian distribution to increase the accuracy of reference and patient maps. The trained feature network is based on a "Siamese" network approach, with the constraint that the two sets must share the same parameters. When completed, the patient's drug-induced trained pattern networks are coupled with those obtained from the reference database, pairing efficacy feature set pairs and adverse event feature set pairs. These provide the basis for the development of a trained efficacy metric and a trained adverse event metric that attempt to match all of the features from the patient and the reference set for the drug of interest. These pairwise matching scores yield separate efficacy and adverse event similarity scores between reference and patient.

In a further embodiment, a reference pattern matching set may be developed for each patient that could be used to create a patient-specific database of such reference maps, and updated in a periodic manner as additional biosamples are obtained from the patient in a longitudinal manner, obtained in a clinical setting or outpatient pharmacy over time.

In any event, the drug and dose decision server 102 may then use the similarity scores for the efficacy and adverse event sub-networks for the psychotropic drug of interest, generated via the method 700, to determine whether to administer the psychotropic drug of interest to the patient. For example, the similarity score for the efficacy sub-network may be compared to a threshold similarity score. If the similarity score for the efficacy sub-network is above the threshold similarity score, the drug and dose decision server 102 may determine that the psychotropic drug of interest should be administered to the patient. The similarity score for the adverse event sub-network may also be compared to a threshold similarity score. If the similarity score for the adverse event sub-network is below the threshold similarity score, the drug and dose decision server 102 may determine that the psychotropic drug of interest should be administered to the patient. In another embodiment, the similarity scores for the efficacy sub-network and the adverse event sub-network may be combined or aggregated in any suitable manner. For example, the similarity score for the adverse event sub-network may be subtracted from the similarity score for the efficacy sub-network. If the combined score is greater than a threshold similarity score, the drug and dose decision server 102 may determine that the psychotropic drug of interest should be administered to the patient.

Otherwise, the drug and dose decision server 102 may determine not to administer the psychotropic drug of interest, and may provide a recommendation to the health care professional's client device 106-116 to administer another drug to treat the patient's depression.

In some embodiments, the drug and dose decision server 102 may determine whether to administer the psychotropic drug of interest to the patient by generating a machine learning model based on training data from drug responses from patients previously prescribed the psychotropic drug of interest. The machine learning model may be generated based on several characteristics of the previous patients including drug-induced sub-networks for the previous patients, PD and PK SNPs that stratify patients by drug response, neuroimaging data, direct TAD-specific measures including differential gene expression, and clinical variables for the previous patients such as age, weight, biological sex, body mass index, ethnicity, family history, patient history of substance abuse, diagnostic codes, hospitalization history, drug-drug interactions, mental illness history, whether the patient smokes or uses nicotine, and Hamilton Scale for Depression (HAM-D) score. The drug and dose decision server 102 may obtain the same characteristics for a current patient including molecular and clinical data and apply the current patient's characteristics to the generated machine learning model to determine whether to administer the psychotropic drug of interest to the patient.

In addition to determining whether to administer the psychotropic drug of interest to the patient, the drug and dose decision server 102 determines the dosage to administer to the patient. FIGS. 18A and 18B illustrate an analysis performed on an independent cohort dataset for the development of a regression model for the dose estimation of ketamine. The published literature and other sources have provided both pharmacokinetic SNP data and clinical values that help determine dose based on CYP2B6 SNPs and clinical data. As can be seen from the differential analysis, the biggest contribution to ketamine dose is the presence or absence of the poor metabolizer phenotype, rs3745274, a variant that causes exon skipping and loss of the hyper-inducible CYP2B6 first pass metabolism of ketamine. The range of quantitative intra-nasal ketamine doses in this model derivation cohort was 0.4 to 0.8 mg/kg. The drug and dose decision server 102 may generate the model based on published ketamine clinical trial results obtained from clinicaltrials.org. A generic example of summed values based on regression variables that could be included in the ketamine-dosing algorithm is illustrated in the equation below:

$$Dose=\exp[2.00 \times rs3745274+0.25 \times female\ (biological\ sex)+0.22 \times rs3786547+0.22 \times clopidogrel+0.19 \times rs11083595+0.11 \times BSA+0.20 \times smokes+0.17 \times suicide\ attempt\ history+0.07 \times age\ per\ decade+0.09 \times Non\text{-}Hispanic\ white\ ethnicity+020 \times ticlopidine+0.15 \times previous\ psychiatric\ hospitalization]$$

More specifically, the drug and dose decision server 102 may generate the dosing algorithm based on published literature and may have predetermined constants to apply to each of several patient characteristics, such as biological characteristics, demographic characteristics, clinical characteristics, etc., as in the equation above. In other embodiments, the drug and dose decision server 102 may generate the dosing algorithm using machine learning techniques. For example, the drug and dose decision server 102 may collect dosing information on patients previously prescribed ketamine as training data. The dosing information may include the dosage each patient was prescribed along with indications of whether the patient's dosage was adjusted during treatment and/or whether the patient experienced adverse events. The drug and dose decision server 102 may then analyze the training data to generate a machine learning model (e.g., a neural network, a decision tree, a hyperplane, a regression model, etc.) to determine the dosage for a new patient based on the new patient's biological characteristics, demographic characteristics, and clinical characteristics. The patient characteristics utilized in the dosing algorithm may include biological data, such as SNPs that have been reported to stratify response to ketamine in humans. The patient characteristics may also include demographic data for the patient, such as the patient's sex, height and weight, age, and ethnicity. Furthermore, the patient characteristics may include clinical data, such as family history, drug-drug interactions, mental illness history, whether the patient smokes or uses nicotine, and Hamilton Scale for Depression (HAM-D) score.

In any event, the drug and dose decision server 102 applies the patient's characteristics to the dosing algorithm to determine a dosage of ketamine to administer to the patient. Then the drug and dose decision server 102 provides the recommended dosage to a health care professional's client device 106-116.

Although regression analysis for patient-specific dose optimization cannot account for almost half of the pharmacogenomic and clinical variables required for accuracy, a few published studies have reported variables to include for algorithmic determination of antidepressant selection and dose estimation. Clinical values obtained from a medical record are also critical for determining decreases in the dosing of ketamine, as shown in FIG. 13. These include a body mass index (BMI) over 30, a family history of alcohol use disorder (first degree), a history of suicide attempt(s), previous psychiatric hospitalization, a female biological sex (pre-menopausal), non-Hispanic white ethnicity, and individuals who smoke tobacco. As indicated, these values contribute to ketamine dosing that can be substantive, but do not rule out use of this medication.

In addition to comparing the patient's sub-networks for the psychotropic drug of interest to reference sub-networks for the psychotropic drug of interest, the drug and dose decision server 102 analyzes clinical data and neuroimaging data for the patient to determine whether to administer the drug to the patient. For example, the drug and dose decision server 102 may analyze the patient's HAMD score and/or patient symptoms to categorize the patient into one of four TRD patient subtypes.

FIG. 19 shows the four TRD patient subtypes as determined by transcranial magnetic stimulation (TMS) coupled with neuroimaging of resting connectivity network in human brain. In patients with TRD, subtypes have been identified and replicated using transcranial magnetic stimulation (TMS) and neuroimaging studies, which have discretized the subtypes by differential activation and repression of the resting state connectivity network in human brain. TMS has four different anatomical placements on the outside of the human head that activate different neuroanatomical structures that are part of limbic-cortical circuits, and include parts of the resting state connectivity network, the default mode network, the defense response that involves the amygdala, reward circuits located in the basal forebrain including the nucleus accumbens (NA) or orbitofrontal cortex (OFC) in depression subtype 3, gating of sensory stimuli to the cortex through the thalamus, cortical region 51 and the insula, prefrontal cortical restraint of impulsivity involving the dorsolateral and dorsomedial prefrontal cortex inhibition of the amygdala activation of limbic cortex, including the entire anterior cingulate cortex and memory consolidation in the hippocampal formation.

FIG. 19 also illustrates that TRD subtypes can be identified using clinical data obtained from an EHR or other clinical records, either using structured values or from notes using natural language processing.

FIG. 20 shows regions of the brain that are consistently activated during the ketamine antidepressant response and how they are differentially mapped to the four TRD depression subtypes. Although brain regions are involved, these are consistent with both the different depression subtypes as defined by TMS and clinical values, as well as results from the neuroimaging studies, which have examined ketamine-induced activation and suppression.

FIG. 21 provides recommendations for medication switching from ketamine for the 4 different TRD subtypes based on defining HAMD-17 rating (Hamilton Scale of Depression), the neuroimaging meta-analysis, associated clinical values as shown in FIG. 19, and available information concerning the efficacy, indications and recommendations for currently available antidepressants and professional guidelines from the American Psychiatric Association.

FIG. 21 illustrates example drug recommendations and alternative medication options for each of the four different subtypes of TRD depressed patients.

To identify which depression subtypes should or should not be provided with ketamine and ketamine analogs, 24 publicly available neuroimaging datasets are analyzed to determine the neuroanatomical regions that are activated by ketamine and its analogs, depressed and TRD patients and healthy controls. Since TRD subtype 3 patients consistently exhibit hyperactive sub-geniculate anterior cingulate cortex (sgACC), dorsolateral and dorsomedial prefrontal (executive) cortices (dlPFC, dmPFC) and hyperactive orbitofrontal cortex (OFC), it is recommended that these patients do not receive ketamine pharmacotherapy because this patient cohort will not respond or remit, but may instead experience exaggerated psychotropic adverse drug events. Independent analysis of the neuroanatomical localization of all of the genes found in the ketamine pharmacogenomic network shows that they are all expressed at high levels in the anterior cingulate gyrus, prefrontal cortex, supplementary motor cortex, orbitofrontal cortex, temporal cortex, amygdala, hippocampal formation, anterior caudate and nucleus accumbens, but not in other cortical brain regions, hypothalamus or brainstem. This is identical to the pattern of 24 functional neuroimaging studies that were examined showing where ketamine first acts in human brain to exert its antidepressant action (Table 1).

TABLE 1

Functional neuroimaging studies demonstrate the human CNS substrate where ketamine and other NMDAR modulators act, and in which all of the genes in the ketamine pharmacogenomic network are expressed at their highest levels.

| TITLE | PARTICIPANTS | KETAMINE'S SITE(S) OF ACTION | MOD. | PMID |
|---|---|---|---|---|
| Effects of sub-anesthetic doses of ketamine on regional cerebral blood flow, oxygen consumption, and blood volume in humans | 9 healthy controls | Anterior cingulate cortex (ACC) and prefrontal cortex (PFC). Not recognized - anterior caudate (AC) and nucleus accumbens (NA). | PET | 12960545 |
| Effects of ketamine on anterior cingulate glutamate metabolism in healthy humans: a 4-T proton MRS study | 10 healthy controls | Anterior cingulate cortex (ACC). | 1H-MRS | 15677610 |
| Increased anterior cingulate cortical activity in response to fearful faces: A neurophysiological biomarker that predicts rapid antidepressant response to ketamine | 11 healthy controls and 11 drug-free patients diagnosed with MDD | Patients with MDD exhibited increased activity in the anterior cingulate cortex (ACC) after pretreatment with fearful faces versus controls. Also, changes observed in right amygdala (AMY). | MEG | 18822408 |
| Anterior cingulate desynchronization and functional connectivity with the amygdala during a working memory task predict rapid antidepressant response to ketamine | 15 drug-free patients diagnosed with MDD | Subgenual anterior cingulate cortex (ACC), supplementary motor area (SMA) and amygdala (AMY). | MEG | 20393460 |
| Ketamine decreases resting state functional network connectivity in healthy subjects: Implications for antidepressant drug action | 17 healthy controls | Subgenual anterior cingulate cortex (sgACC), dorsomedial prefrontal cortex (PFC), | fMRI BOLD | 23049758 |
| Relationship of resting brain hyperconnectivity and schizophrenia-like symptoms produced by the NMDA receptor antagonist ketamine in humans | 22 healthy controls; Replication in another 12 healthy controls | Ketamine administration increased global brain connectivity. Psychotomimetic (negative) effects following ketamine administration were localized to the nucleus accumbens (NA) and anterior caudate (AC). Positive symptoms were associated with changes in prefrontal cortex (PFC), supplementary motor area (SM), insula and posterior cortex. | rs-fcMRI | 23337947 |
| Neural correlates of rapid antidepressant response to ketamine in treatment-resistant unipolar depression: A preliminary PET study | 20 drug-free patients diagnosed with TRD | Anterior cingulate cortex (ACC), prefrontal cortex (PFC), amygdala (AMY) and habenula. | PET | 23540908 |
| Neural correlates of rapid antidepressant response to ketamine in bipolar disorder | 21 patients with bipolar depression | Sub-geniculate anterior cingulate cortex (ACC), supplementary motor area (SMA), prefrontal cortex (PFC). Also, unrecognized, but included amygdala (AMY), hippocampal formation (HF), anterior caudate (AC) and nucleus accumbens (NA). | PET | 24103187 |
| Anti-anhedonic effect of ketamine and its neural correlates in treatment-resistant bipolar depression | 36 patients who are treatment-refractory diagnosed with | Ketamine significantly activated the dorsal anterior cingulate cortex (dACC) and the subcortex. | PET | 25313512 |

TABLE 1-continued

Functional neuroimaging studies demonstrate the human CNS substrate where ketamine and other NMDAR modulators act, and in which all of the genes in the ketamine pharmacogenomic network are expressed at their highest levels.

| TITLE | PARTICIPANTS | KETAMINE'S SITE(S) OF ACTION | MOD. | PMID |
|---|---|---|---|---|
| Neural correlates of change in major depressive disorder anhedonia following open-label ketamine. | bipolar disorder I or II 52 patients diagnosed with TRD | Supplementary motor area (SMA), hippocampal formation (HF), frontal gyrus and orbitofrontal cortex correlated with measures of decreased anhedonia in patients diagnosed with MDD. Borderline significance. | PET | 25691504 |
| A pilot in vivo proton magnetic resonance spectroscopy study of amino acid neurotransmitter response to ketamine treatment of major depressive disorder | 11 patients diagnosed with MDD | Prefrontal cortex (PFC). | 1H-MRS | 26283639 |
| The effects of low-dose ketamine on the prefrontal cortex and amygdala in treatment-resistant depression: A randomized controlled study | 48 patients diagnosed with TRD | Prefrontal cortex (PFC), amygdala (AMY) and supplementary motor area (SMA). | PET | 26821769 |
| Ketamine modulates subgenual cingulate connectivity with the memory-related neural circuit-a mechanism of relevance to resistant depression? | 13 healthy controls | Following ketamine infusion, largest changes observed in the connectivity of the subgenual anterior cingulate cortex (sgACC). | fMRI | 26925332 |
| Comparing the actions of Lanicemine and ketamine in depression: key role of the anterior cingulate | 60 un-medicated patients diagnosed with MDD | Intravenous infusion of both ketamine and Lanicemine gradually increased activity in the subgenual anterior cingulate cortex (sgACC). | phMRI | 27133029 |
| Ketamine modulates hippocampal neurochemistry and functional connectivity - A combined magnetic resonance spectroscopy and resting state fMRI study in healthy volunteers | 15 healthy controls | Dorsomedial prefrontal cortex (PFC) and anterior cingulate cortex (ACC). Psychosis severity produced by ketamine was associated with increased connectivity of the hippocampal formation (HF) with the middle cingulate cortex, insula, precuneus and superior frontal gyrus. | rs-fcMRI; 1H-MRS | 27480949 |
| Ketamine treatment and global brain connectivity in major depression | 25 healthy controls and 18 drug-free patients diagnosed with MDD | Subgenual anterior cingulate cortex (sgACC), dorsolateral prefrontal cortex and dorsomedial prefrontal cortex (PFC), anterior caudate (AC), nucleus accumbens (NA). | rs-fcMRI | 27604566 |
| The nucleus accumbens and ketamine treatment in major depressive disorder | The first cohort was 34 patients diagnosed with MDD and 26 healthy controls. The second cohort was 16 patients diagnosed with MDD. | The volume of the nucleus accumbens (NA) was altered in MDD patients, while hippocampal formation (HF) volume was increased following ketamine in MDD patients who exhibited remission. | 1H-MRS | 28272497 |
| Persistent antidepressant effect of low dose ketamine and activation in the supplementary motor area and anterior cingulate cortex in treatment-resistant depression: A randomized control study | 24 patients diagnosed with TRD | TRD patients receiving the 0.5 mg/kg ketamine infusion exhibited activation in supplementary motor area (SMA) and anterior cingulate cortex (ACC) than did those receiving the 0.2 mg/kg ketamine infusion. The increase in the SUV in the ACC was negatively correlated with depressive symptoms after ketamine infusion. | PET | 28922734 |
| Glutamate levels and resting cerebral blood flow in anterior cingulate cortex are associated at rest and immediately following infusion of S-ketamine in healthy volunteers | 25 healthy controls | Dorsomedial prefrontal cortex (PFC) and anterior cingulate cortex (ACC). | 1H-MRS | 29467681 |

TABLE 1-continued

Functional neuroimaging studies demonstrate the human CNS substrate where ketamine and other NMDAR modulators act, and in which all of the genes in the ketamine pharmacogenomic network are expressed at their highest levels.

| TITLE | PARTICIPANTS | KETAMINE'S SITE(S) OF ACTION | MOD. | PMID |
|---|---|---|---|---|
| Default mode connectivity in major depressive disorder measured up to 10 days after ketamine administration | 33 patients diagnosed with MDD and 25 healthy controls in a cross-over study | MDD patients exhibited normalization of connectivity between the insular cortex (IC), posterior anterior cingulate cortex (pACC) and subgenual anterior cingulate cortex (sgACC). | fMRI | 29580569 |
| 7T 1H-MRS in major depressive disorder: A Ketamine Treatment Study | 17 healthy controls and 20 patients diagnosed with MDD | Different MDD phenotypes exhibited different brain region alterations following ketamine infusions, ranging from sub-geniculate anterior cingulate cortex (ACC) to anterior caudate (AC). | 1H-MRS | 29748628 |
| Pharmacological fMRI: Effects of sub-anesthetic ketamine on resting-state functional connectivity in the default mode network, salience network, dorsal attention network and executive control network | 17 healthy male subjects | Anterior cingulate cortex (ACC), superior frontal gyrus including supplementary motor area (SMA), amygdala (AMY), hippocampal formation (HF), anterior caudate (AC), nucleus accumbens (NA), prefrontal cortex (PFC). | rs-fcMRI | 30003027 |
| Ketamine, but Not the NMDAR antagonist Lanicemine, Increases prefrontal global connectivity in depressed patients | 56 un-medicated patients diagnosed with MDD | Ketamine increased global connectivity of the prefrontal cortex (PFC) in depressed patients. | fMRI | 30263977 |
| Functional connectivity between prefrontal cortex and Subgenual cingulate predicts antidepressant effects of ketamine | 24 patients diagnosed with MDD | A single sub-anesthetic dose of ketamine increased functional connectivity between prefrontal Cortex (PFC) and the subgenual anterior cingulate cortex (sgACC). | rs-fcMRI | 30819549 |
| The antidepressant effect of ketamine is not associated with changes in occipital amino acid neurotransmitter content as measured by [$^1$H]-MRS | 10 patients diagnosed with MDD | Rapid (1 hour) and sustained (7 days) antidepressant effects produced by ketamine were not associated with changes in amino acid neurotransmitter content in occipital cortex (OC). | 1H-MRS | 21232924 |

Neuroimaging Modalities (MOD.):
  1H-MRS: 4-T 1H proton magnetic resonance spectroscopy
  fMRI: Functional magnetic resonance imaging.
  MEG: Magnetoencephalography;
  PET: FDG positron emission tomography;
  phMRI; Pharmacological magnetic resonance imaging.
  rs-fcMRI: resting-state functional connectivity magnetic resonance imaging.

In another embodiment, disease risk and pharmacogenomic SNPs that discriminate the 2 significantly different ketamine sub-networks in human brain may be used to determine a patient's response and adverse events when treated with ketamine. Table 2A lists the enhancer and super-enhancer SNPs that have been found in the ketamine efficacy sub-network that may be used to determine the representation of mutations significantly associated with efficacious response to ketamine. In contrast, Table 2B lists the enhancer and super-enhancer SNPs that have been found in the ketamine adverse event sub-network that may be used to determine the representation of mutations significantly associated with adverse CNS events in response to ketamine.

TABLE 2A

Part 1. Enhancer and superenhancer SNPs that have been found in the ketamine efficacy sub-network.

| GWAS SNP Reported/ Population(s) | Reported gene(s) | Variant type | Reported trait | P-value | Odds ratio or beta | Confidence Interval (95%) | PubMed ID | EBI-NHGRI Accession Number |
|---|---|---|---|---|---|---|---|---|
| rs7623659-T/EUR | RHOA | Intronic | Cognitive performance | 4.00E−57 | 0.0395 | 0.035-0.044 unit increase | 30038396 | GCST006570 |
| rs12229654-G/ASN | LINC01405-CUX2 | Intergenic | Alcohol consumption (drinkers versus non-drinkers) | 2.00E−48 | 2.31 | | 21270382 | GCST004404 |

TABLE 2A-continued

Part 1. Enhancer and superenhancer SNPs that have been found in the ketamine efficacy sub-network.

| GWAS SNP Reported/ Population(s) | Reported gene(s) | Variant type | Reported trait | P-value | Odds ratio or beta | Confidence Interval (95%) | PubMed ID | EBI-NHGRI Accession Number |
|---|---|---|---|---|---|---|---|---|
| rs30266-A/ EUR | ENSG00000251574 | Intergenic | Recurrent depression (F33) | 2.00E−45 | 1.033 | 1.028-1.037 | 30718901 | GCST007342 |
| rs61902811-G/EUR | TMPRSS5, DRD2 | Intergenic | Recurrent depression (F33) | 4.00E−39 | 1.0288066 | 1.02-1.03 | 30718901 | GCST007342 |
| rs12229654-G/ASN | LINC01405-CUX2 | Intergenic | Alcohol consumption | 4.00E−35 | 0.79 | [0.67-0.91] unit decrease | 21270382 | GCST000954 |
| rs6265-T/ EUR | BDNF, BDNF-AS | Intragenic; non-synonomous | Smoking status | 9.00E−29 | 0.029275492 | 0.023-0.036 unit decrease | 30643251 | GCST007468 |
| rs7227069-A/EUR | DCC | 3' UTR | Recurrent depression (F33) | 2.00E−28 | 1.024 | 1.02-1.029 | 30718901 | GCST007342 |
| rs12967143-G/EUR | TCF4 | Intragenic | Recurrent depression (F33) | 2.00E−27 | 1.025641 | 1.02-1.03 | 30718901 | GCST007342 |
| rs4938021-T/EUR | TMPRSS5, DRD2 | Intergenic | Wellbeing, life satisfaction | 3.00E−26 | 0.010079761 unit increase | [0.0082-0.0119] | 30643256 | GCST007341 |
| rs6589377-A/EUR | TMPRSS5, DRD2 | Intergenic | Neuroticism, loneliness | 4.00E−26 | 0.016052796 unit increase | 0.016052796 unit increase | 30718901 | GCST007340 |
| rs6589377-A/EUR | TMPSS5, DRD2 | Intergenic | Depressive symptom measurement | 5.00E−26 | 0.016052796 | 0.013-0.019 unit increase | 30643256 | GCST007339 |
| rs7932640-T/EUR | GRM5 | Intragenic | Recurrent depression (F33) | 3.00E−25 | 0.4417 | 1.023 | 30718901 | GCST007342 |
| rs7111031-A/EUR | TMPRSS5, DRD2 | Intergenic | Well being, positive affect | 3.00E−24 | 0.012320721 unit increase | [0.0099-0.0147] | 30643256 | GCST007338 |
| rs11662271-T/EUR | DCC | Intragenic | Cognitive function | 3.00E−24 | 0.0233 unit increase | [0.019-0.028] | 30038396 | GCST006570 |
| rs1373178-G/EUR | DCC | Intragenic | Smoking status | 2.00E−22 | 0.0107536 | 0.0086-0.0129 unit decrease | 30643251 | GCST007468 |
| rs1925950-G/EUR | MEF2D | Intragenic; non-synonomous | Migraine | 9.00E−22 | 1.07 | 1.06-1.09 | 27322543 | GCST003720 |
| rs8084280-T/EUR | DCC | Intragenic | Depressive symptom measurement | 3.00E−19 | 0.008229027 | 0.0064-0.01 unit increase | 30643256 | GCST007340 |
| rs7111031-A/EUR | DRD2 | Intergenic | Neuroticism | 2.00E−18 | 0.012320721 | 0.0099-0.0147 unit increase | 29255261 | GCST005232 |
| rs1925950-G/EUR | MEF2D | Intragenic; non-synonomous | Migraine | 2.00E−18 | 1.29 | 1.20-1.34 | 27182965 | GCST003720 |
| rs12520354-A/EUR | RASGFR2-AS | Intragenic | Risk-taking behavior | 3.00E−17 | 0.0114 | 0.0087-0.0141 unit increase | 30643258 | GCST007325 |
| rs599550-A/ EUR | TCF4 | Intragenic | Depressed affect, mood disorders | 4.00E−17 | 6.53 | z-score increase | 29942085 | GCST006475 |
| rs613872-C/ EUR | TCF4 | Intragenic | Loneliness | 4.00E−17 | 0.022766946 | 0.017-0.028 unit decrease | 29970889 | GCST006924 |
| rs8084280-T/EUR | DCC | Intragenic | Wellbeing, life satisfaction | 3.00E−16 | 0.010693542 unit increase | [0.0081-0.0133] | 30643256 | GCST007337 |
| rs11662271-T/EUR | DCC | Intragenic | Increased cognition | 4.00E−16 | 0.0233 unit increase | [0.019-0.028] | 30018396 | GCST006572 |
| rs12967143-C/EUR | TCF4 | Intragenic | Well being | 9.00E−16 | 0.008096604 unit decrease | [0.0061-0.0101] | 30643256 | GCST007341 |

TABLE 2A-continued

Part 1. Enhancer and superenhancer SNPs that have been found in the ketamine efficacy sub-network.

| GWAS SNP Reported/ Population(s) | Reported gene(s) | Variant type | Reported trait | P-value | Odds ratio or beta | Confidence Interval (95%) | PubMed ID | EBI-NHGRI Accession Number |
|---|---|---|---|---|---|---|---|---|
| rs8181326-A/EUR | ARHGAP19, SLIT1 | Intergenic | Risk-taking behavior | 1.00E−15 | 0.016249152 unit decrease | [0.012-0.02] | 30643258 | GCST007324 |
| rs72930774-A/EUR | TCF4-AS2, TCF4 | Intergenic | Risky sexual behavior measurement | 2.00E−15 | 0.04191511 unit increase | [0.032-0.052] | 30643258 | GCST007326 |
| rs2958162/EUR | TCF4 | Intragenic | Depressive symptoms | 3.00E−15 | 1.51 | 1.45-1.57 | 30643256 | GCST007339 |
| rs7949802-T/EUR | TMPRSS5, DRD2 | Intergenic | Wellbeing, life satisfaction | 6.00E−15 | 0.011424591 unit decrease | [0.0086-0.0143] | 30643256 | GCST007337 |
| rs1660237-T/EUR | TCF4 | Intragenic | Well being, positive affect | 7.00E−15 | 0.00893267 unit increase | [0.0067-0.0112] | 30643256 | GCST007338 |
| rs674437-A/EUR | GRM5 | Intragenic | Depressive symptoms | 9.00E−15 | 0.008528544 | [0.0064-0.0107] unit decrease | 30643256 | GCST007340 |
| rs624244/EUR | TCF4 | Intragenic | Risk-taking behavior | 2.00E−14 | 0.0095 unit decrease | [0.0071-0.0119] | 30643258 | GCST007325 |
| rs8099160/EUR | DCC | Intragenic | Recurrent depression (F33) | 2.00E−14 | 7.638 z score increase | | 29942085 | GCST006477 |
| rs674437-A/EUR | GRM5 | Intragenic | Positive affect | 2.00E−14 | 0.010211199 unit decrease | [0.0076-0.0128] | 30643256 | GCST007388 |
| rs599550-A/EUR | TCF4 | Intragenic | Feeling "fed-up" measurement | 3.00E−14 | 7.6 z score increase | | 29500382 | GCST006947 |
| rs7117514-G/EUR | SHANK2 | Intragenic | Recurrent depression (F33) | 4.00E−14 | 1.0162601 | [1.01-1.02] | 30718901 | GCST007342 |
| rs2163971-T/EUR | CADM2 | Intragenic | Risky sexual behavior measurement | 5.00E−14 | 0.017939975 unit increase | [0.013-0.023] | 30643258 | GCST007326 |
| rs4936277-A/EUR | DRD2, TMPSS5 | Intergenic | Alcohol use disorder, alcohol dependence | 1.00E−13 | 7.44 z score increase | | 29942085 | GCST008259 |
| rs13357015/EUR | RASGFR2 | Intragenic | Smoking status | 1.00E−13 | | | 30643251 | GCST007468 |
| rs17601612-C/EUR | DRD2, TMPSS5 | Intergenic | Alcohol consumption | 2.00E−13 | | | 30643258 | GCST007328 |
| rs8084351/EUR | DCC | Intragenic | Depressive symptom measurement | 2.00E−13 | | | 29292387 | GCST005323 |
| rs61687445-A/EUR | DRD2, TMPSS5 | Intergenic | Well being | 2.00E−13 | 0.006787939 unit decrease | [0.005-0.0086] | 30643256 | GCST007341 |
| rs35738585/EUR | DRD2, TMPSS5 | Intergenic | Depressed affect | 2.00E−13 | 0.01722 unit decrease | [0.013-0.022] | 29942085 | GCST006475 |
| rs9636107-G/EUR | TCF4 | Intragenic | Schizophrenia | 1.00E−12 | | | 26198764 | GCST003048 |
| rs12968428-A/EUR | DCC | Intragenic | Recurrent depression (F33) | 2.00E−12 | 7.065 z score increase | | 29942085 | GCST06477 |
| rs8138473/EUR | SHANK3 | Intragenic | Cognitive performance | 3.00E−12 | 0.0194 unit decrease | [0.014-0.025] | 30038396 | GCST006570 |
| rs619466-G/EUR | TCF4 | Intragenic | Depressive symptoms | 3.00E−12 | 0.010945462 unit increase | [0.0079-0.014] | 30643256 | GCST007340 |
| rs1431181-A/EUR | DCC | Intranegic | Recurrent depression (F33) | 3.00E−12 | 6.958 z score increase | | 29942085 | GCST06477 |
| rs1261070-?/EUR | TCF4 | Intragenic | Unipolar depression, mood disorders | 6.00E−12 | 0.02838 unit decrease | [0.02-0.036] | 29942085 | GCST006475 |
| rs611439-?/EUR | TCF4 | Intragenic | Unipolar depression, mood disorders | 6.00E−12 | 0.02861 unit decrease | [0.02-0.037] | 29942085 | GCST006475 |
| rs7231748-A/EUR | TCF4 | Intragenic | Irritable mood | 7.00E−12 | 6.87 z score decrease | | 29500382 | GCST006941 |
| rs4277413-A/EUR | DCC | Intragenic | Recurrent depression (F33) | 1.00E−11 | 6.77 z score decrease | | 29942085 | GCST06477 |

TABLE 2A-continued

Part 1. Enhancer and superenhancer SNPs that have been found in the ketamine efficacy sub-network.

| GWAS SNP Reported/ Population(s) | Reported gene(s) | Variant type | Reported trait | P-value | Odds ratio or beta | Confidence Interval (95%) | PubMed ID | EBI-NHGRI Accension Number |
|---|---|---|---|---|---|---|---|---|
| rs1050316/ EUR | MEF2D | Intra genic | Headache | 2.00E−11 | 0.0098 unit decrease | [0.0069-0.0127] | 29397368 | GCST005337 |
| rs139438618/ AFR | SEMA3A | Intra genic | Major depression and alcoholism | 2.00E−11 | 0.869 unit increase | | 29071344 | GCST005022 |
| rs8089865-A/EUR | DCC | Intra genic | Depressed affect, mood disorders | 3.00E−11 | 6.624 z score increase | | 29942085 | GCST06477 |
| rs12958048-A/EUR | TCF4 | Intra genic | Recurrent depression (F33) | 4.00E−11 | 1.03 | [1.02-1.04] | 29700475 | GCST005839 |
| rs9636107/ EUR | TCF4 | Intra genic | Autism spectrum disorder or schizophrenia | 5.00E−11 | 1.0638298 | [1.04-1.09] | 28540026 | GCST004521 |
| rs17598729-C/ASN | TCF4 | Intra genic | Schizophrenia | 9.00E−11 | 1.0893246 | [1.06-1.12] | 30285260 | GCST007201 |
| rs4801157/ EUR | TCF4 | Intra genic | Depressed affect, mood disorders | 2.00E−10 | 0.01921 unit increase | [0.013-0.025] | 29942085 | GCST006475 |
| rs4384683-G/EUR | DCC | Intra genic | Chronic back pain | 2.00E−10 | 1.0309278 | [1.02-1.04] | 30261039 | GCST007152 |
| rs674437-A/ EUR | GRM5, TYR | Inter genic | Neuroticism, vulnerability | 3.00E−10 | 6.31 z score decrease | | 29500382 | GCST006476 |
| rs4938021-T/EUR | DRD2-TMPRSS5 | Inter genic | Neuroticism, loneliness | 4.00E−10 | 0.02327652 | [0.016-0.031] unit increase | 27089181 | GCST003770 |
| rs624244-A/ EUR | TCF4 | Intra genic | Risk taking dependency | 7.00E−10 | 0.01678442 unit decrease | [0.011-0.022] | 30643258 | GCST007323 |
| rs674437-A/ EUR | GRM5, TYR | Intra genic | Neuroticism | 8.00E−10 | 6.146 z score decrease | | 29942085 | GCST006940 |
| rs7228159-A/EUR | TCF4 | Intra genic | Feeling worry | 1.00E−09 | 6.046 unit increase | | 29500382 | GCST006950 |
| rs61905363-T/EUR | DRD2 | Intra genic | Depressive symptom measurement | 1.00E−09 | 0.014688093 unit decrease | [0.0099-0.0194] | 30643256 | GCST007340 |
| rs4936277-G/EUR | DRD2, TMPSS5 | Intra genic | Depressive symptom measurement | 2.00E−09 | 0.006741934 unit decrease | [0.0045-0.0089] | 30643256 | GCST007340 |
| rs17041417-A/EUR | ASCL1 | Intra genic | Neuroticism | 2.00E−09 | 0.011447053 unit increase | [0.0077-0.0152] | 30643258 | GCST007339 |
| rs17041417-A/EUR | ASCL1 | Intra genic | Depressive symptom measurement | 2.00E−09 | 0.00732364 unit increase | [0.0049-0.0097] | 30643258 | GCST007340 |
| rs17041417-A/EUR | ASCL1 | Intra genic | Positive affect | 3.00E−09 | 0.008780573 unit increase | [0.0059-0.0117] | 30643256 | GCST007338 |
| rs9811546-A/EUR | CADM2 | Intra genic | Feeling tense | 6.00E−09 | 5.83 z score decrease | | 29500382 | GCST006952 |
| rs17041417-A/EUR | ASCL1 | Intra genic | Wellbeing, life satisfaction | 6.00E−09 | 0.009325971 unit increase | [0.0062-0.0125] | 30643256 | GCST007337 |
| rs12575685/ EUR | SHANK2 | Intra genic | Bipolar disorder | 8.00E−09 | 1.07272 | [1.05-1.1] | 31043756 | GCST008103 |
| rs2274316-C/EUR | MEF2D | Intra genic | Migraine | 1E−08 | 1.07 | [1.05-1.10] | 23793025 | GCST002081 |
| rs775766-A/ EUR | ROBO2 | Intra genic | Recurrent depression (F33) | 2.00E−08 | 5.659 z score increase | | 29942085 | GCST006477 |
| rs310763-C/ EUR | SYN2 | Intra genic | Depressive symptom measurement | 3.00E−08 | 0.006332982 unit decrease | [0.0041-0.0086] | 30643256 | GCST007340 |
| rs310763-C/ EUR | SYN2 | Intra genic | Well being, positive affect | 3.00E−08 | 0.007597797 unit decrease | [0.0049-0.0103] | 30643256 | GCST007338 |
| rs310763-C/ EUR | SYN2 | Intra genic | Wellbeing, life satisfaction | 3.00E−08 | 0.0062105684 unit decrease | [0.004-0.0084] | 30643256 | GCST007341 |
| rs1016306-T/EUR | CADM2 | Intra genic | Well being | 5.00E−08 | 0.005018757 unit decrease | [0.0032-0.0068] | 30643256 | GCST007341 |

TABLE 2A-continued

Part 1. Enhancer and superenhancer SNPs that have been found in the ketamine efficacy sub-network.

| GWAS SNP Reported/ Population(s) | Reported gene(s) | Variant type | Reported trait | P-value | Odds ratio or beta | Confidence Interval (95%) | PubMed ID | EBI-NHGRI Accession Number |
|---|---|---|---|---|---|---|---|---|
| rs935526-T/ EUR | ROBO2 | Intra genic | Recurrent depression (F33) | 5.00E−08 | 5.452 z score decrease | | 29942085 | GCST006477 |
| rs161645-A/ EUR | ENSG00000251574 | Inter genic | Depression (quantitative trait) | 8.00E−08 | | | 23290196 | GCST001802 |
| rs17211233-T/EUR | RASFGRF2 | Intra genic | Response to ketamine in bipolar disorder or major depression (decrease in dissociation effects) | 2.00E−07* | 26.9757 unit decrease | [17.75-36.2] | 30552316 | GCST007317 |
| rs11214606/ EUR | DRD2 | Intra genic | Response to antipsychotic treatment in schizophrenia (working memory) | 5.00E−07* | | | 21107309 | GCST000883 |
| rs1400237/ EUR | ROBO2 | Intra genic | Response to ketamine in bipolar disorder or major depression (increase in dissociation effects) | 2.00E−06* | 21.4345 unit increase | 13.27-29.6 | 30552316 | GCST007317 |
| rs1846786-T/EUR | ENSG00000225960 | Inter genic | Response to ketamine in bipolar disorder or major depression (decrease in dissociation effects) | 3.00E−06* | 13.9838 unit decrease | [8.54-19.43] | 30552316 | GCST007317 |
| rs4855976/ EUR | ROBO2 | Intra genic | Response to ketamine in bipolar disorder or major depression (increase in dissociation effects) | 8.00E−06* | 23.7477 unit increase | [14.02-33.48] | 30552316 | GCST007317 |
| rs79749176-A/EUR | SLC22A15 | Intra genic | Response to ketamine in bipolar disorder or major depression (increase in antidepressant effects) | 9.00E−06* | 39.0894 unit increase | [22.49-55.69] | 30552317 | GCST007316 |

TABLE 2A

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| rs7623659-T/EUR | RHOA_1 (chr3: | Enhancer, astrocytes, bipolar | | | |

TABLE 2A-continued

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| | | 49411963-49412022) neuron, brain; GH03J049377: chr3: 49414635-49417768 (ENCODE (Z-Lab), Ensembl, dbSUPER; GeneHancer DoubleElite) | | | |
| rs12229654-G/ASN | CUX2_1 (chr12: 111033920-111033979) | Enhancer, Bipolar neuron, H9 neuronal cells, neural progenitor cells; chr12: 111473237-111473713 (chr12: 111035433-111035909, eRNA Score: 49 (ENCODE, FANTOM, Ensembl) | | | 1E0E-11; Brain Frontal Cortex |
| rs30266-A/EUR | | Enhancer, Bipolar neuron, H9 neuronal cells, prefrontal cortex, cingulate cortex; ENSR00000764485: chr5: 105386601-105387599 (Vista, GeneHancer Elite; Ensembl) | | | 7.5E-09, Testis |
| rs61902811-G/EUR | TMPRSS5_1 (chr11: 113706292-113706351) | Enhancer, neural progenitor cell; GH11J11370: chr11: 113705465-113707068) | | | 1.80E-11; Brain Hippocampus |
| rs12229654-G/ASN | CUX2_1 (chr12: 111033920-111033979) | Enhancer, Bipolar neuron, H9 neuronal cells, neural progenitor cells; chr12: 111473237-111473713 (chr12: 111035433-111035909, eRNA Score: 49 (ENCODE, FANTOM, Ensembl) | | | 1E0E-11; Brain Frontal Cortex |
| rs6265-T/EUR | | Enhancer, Brain Hippocampus Middle, Brain Anterior Caudate, Brain Cingulate Gyrus (ENCODE) | DE_00099: chr11: 27739147-27742290; Depression | | 5.08E-06; Nerve tibial |
| rs7227069-A/EUR | DCC_2 (chr18: 52340148-52340207) | Enhancer, prefrontal cortex, cingulate cortex; FANTOM: chr18: | | SE_08791 (Brain - Mid frontal lobe) | 1.0E-21; Brain Cingiulate Gyrus |

TABLE 2A-continued

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| rs12967143-G/EUR | TCF4_1 (chr18: 55401678-55401737) TCF4_9 (chr18: 55401970-55402029) TCF4_4 (chr18: 55403630-55403689) | 52341963-52342477, eRNA Score: 32, Cells: neural progenitor cells Enhancer, prefrontal cortex, cingulate cortex (Vista, GeneHancer Elite) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate) | 1E-11; Brain Frontal Cortex |
| rs4938021-T/EUR | TMPRSS5_1 (chr11: 113706292-113706351) | Enhancer, neural progenitor ceil; GH11J11370: chr11: 113705465-113707068) | | | 1.80E-23; Brain Amygdala |
| rs6589377-A/EUR | TMPRSS5_1 (chr11: 113706292-113706351) | Enhancer, neural progenitor cell; GH11J11370: chr11: 113705465-113707068) | | | 1.80E-11; Brain Hippocampus |
| rs6589377-A/EUR | TMPRSS5_1 (chr11: 113706292-113706351) | Enhancer, neural progenitor cell; GH11J11370: chr11: 113705465-113707068) | | | 1.0E-21; Brain Cingiulate Gyrus |
| rs7932640-T/EUR | | Enhancer, H1 progenitor neurons; ENSR00000438504 (chr11: 89119401-89120000 | | | 1.0E-03; Brain Cingulate Gyrus |
| rs7111031-A/EUR | TTC12_1 (chr11: 113314539-113314598) | Enhancer, Bipolar neuron, Brain; ENSR00000045120 (chr11: 113313800-113315601) (ENCODE, FANTOM, Ensmbl) | | | 1E-37; Brain Anterior Caudate |
| rs11662271-T/EUR | DCC_2 (chr18: 52340148-52340207) | Enhancer, prefrontal cortex, cingulate cortex; FANTOM: chr18: 52341963-52342477, eRNA Score: 32, | | | 1.55E-51; Brain Frontal Cortex |

TABLE 2A-continued

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| rs1373178-G/EUR | | Cells: neural progenitor cells Enhancer, hippocampus, ERNA score 21 (ENCODE, VISTA) | | | 1E−15; Brain Amygdala |
| rs1925950-G/EUR | MEF2D_2 (chr1: 156490647-156490706) MEF2D_1 (chr1: 156500765-156500824) | Enhancer, bipolar neurons, brain (ENCODE, Ensembl, dbSUPER, GeneHancer Double Eite); FANTOM: chr1: 156502901-156503160, eRNA Score: 319; Cells: Neural progenitor cells | | SE_04141 (Brain - Anterior caudate); SE_08791 (Brain - Mid frontal lobe); SE_05851 SE_06826 (Brain - Hippocampus middle); SE_04925 (Brain - Cingulate gyrus); SE_07824 (Brain - Inferior temporal lobe); SE_03183 (Brain - Angular gyrus); SE_02565 (Astrocytes); | 1E−89; Brain Cingulate Gyrus |
| rs8084280-T/EUR | DCC_2 (chr18: 52340148-52340207) | Enhancer, neural progenitor cell (ENCODE) | | | 1.0E−09; Brain Cingulate Cortex |
| rs7111031-A/EUR | ANKK1_1 (chr11: 113387730-113387789) | Enhancer, H1 neuronal progenitor cells, brain, astrocytes, bipolar neurons; GH11J113505: chr11: 113375857-113378219; (ENCODE, Ensemble, Vista, MASTERMIND); FANTOM: chr11: 113375857-113376013 (chr11: 113505135-113505291, eRNA Score: 2) | | | 1E−06; Brain Hippocampus |
| rs1925950-G/EUR | MEF2D_2 (chr1: 156490647-156490706) MEF2D_1 (chr1: 156500765-156500824) | Enhancer, bipolar neurons, brain (ENCODE, Ensembl, dbSUPER, GeneHancer Double Eite); FANTOM: chr1: 156502901-156503160, eRNA Score: 319; Cells: Neural progenitor cells | | SE_04141 (Brain - Anterior caudate); SE_08791 (Brain - Mid frontal lobe); SE_05851 SE_06826 (Brain - Hippocampus middle); SE_04925 (Brain - Cingulate gyrus); SE_07824 (Brain - Inferior temporal lobe); | 1E−89; Brain Cingulate Gyrus |

TABLE 2A-continued

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer- promoter pairs | Superenhancers (dbSUPER) | eQTL |
|---|---|---|---|---|---|
| rs12520354- A/EUR | | Enhancer, Bipolar neurons, brain; ENSR00000183204 (chr5: 80955800- 80956401) | | SE_03183 (Brain - Angular gyrus); SE_02565 (Astrocytes); SE_33104 (Brain - Cingulate gyrus) | |
| rs599550- A/EUR | TCF4_2 (chr18: 55588182- 55588241) TCF4_3 (chr18: 55588605- 55588664) | Enhancer, neural progenitor cells, brain (GeneHancer Elite, Vista, MASTERMIND) | DE_00452: chr18: 55401678- 55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate), SE_33242 (H1-ESC) | 1E−52; Brain Frontal Cortex |
| rs613872- C/EUR | TCF4_2 (chr18: 55588182- 55588241) TCF4_3 (chr18: 55588605- 55588664) | Enhancer, neural progenitor cells, brain (GeneHancer Elite, Vista, MASTERMIND) | DE_00452: chr18: 55401678- 55401737; Depression | SE_33242 (H1-ESC) | 1E−12; Brain Cingulate Gyrus |
| rs8084280- T/EUR | DCC_2 (chr18: 52340148- 52340207) | Enhancer, neural progenitor cell (ENCODE) | | | 1.0E−09; Brain Cingulate Cortex |
| rs11662271- T/EUR | DCC_2 (chr18: 52340148- 52340207) | Enhancer, prefrontal cortex, cingulate cortex; FANTOM: chr18: 52341963- 52342477, eRNA Score: 32, Cells: neural progenitor cells | | | 1.55E−51; Brain Frontal Cortex |
| rs12967143- C/EUR | TCF4_1 (chr18: 55401678- 55401737) TCF4_9 (chr18: 55401970- 55402029) TCF4_4 (chr18: 55403630- 55403689) | Enhancer, prefrontal cortex, cingulate cortex (Vista, GeneHancer Elite) | DE_00452: chr18: 55401678- 55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 | 1E−11; Brain Frontal Cortex |

TABLE 2A-continued

Part 2. Regulatory element associated with enhancer and superenhancer
SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| rs8181326-A/EUR | SLIT1_4 (chr10: 97185502-97185561) | Enhancer, Brain Hippocampus Middle, Brain Anterior Caudate, Brain Cingulate Gyrus (ENCODE) | | (Brain - Angular gyrus); SE_04070 (Brain - Anterior caudate) SE_33104 (Brain - Cingulate gyrus) | |
| rs72930774-A/EUR | TCF4_1 (chr18: 55401678-55401737) TCF4_9 (chr18: 55401970-55402029) TCF4_4 (chr18: 55403630-55403689) | Enhancer, prefrontal cortex, cingulate cortex (Vista, GeneHancer Elite) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate) | 1E-11; Brain Frontal Cortex |
| rs2958162/ EUR | TCF4_2 (chr18: 55588182-55588241) TCF4_3 (chr18: 55588605-55588664) | Enhancer, prefrontal cortex, cingulate cortex (Vista, GeneHancer Elite) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate) | 1.36E-20; Brain Cingulate Gyrus |
| rs7949802-T/EUR | ANKK1_1 (chr11: 113387730-113387789) | Enhancer, H1 neuronal progenitor cells, brain, astrocytes, bipolar neurons; GH11J113505; chr11: 113375857-113378219; (ENCODE, Ensemble, Vista, MASTERMIND); FANTOM: chr11: 113375857-113376013 (chr11: 113505135- | | | 1E-06; Brain Hippocampus |

TABLE 2A-continued

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| rs1660237-T/EUR | | 113505291, eRNA Score: 2) Enhancer, prefrontal cortex, cingulate cortex (Vista, GeneHancer Elite) | DE_00452: chr18: 55401678-55401737; Depression | | |
| rs674437-M/EUR | | Enhancer, H1 progenitor neurons; ENSR00000438504 (chr11: 89119401-89120000 | | | 1E−27; Brain Amygdala |
| rs624244/EUR | TCF4_2 (chr18: 55588182-55588241) TCF4_3 (chr18: 55588605-55588664) | Enhancer, prefrontal cortex, cingulate cortex (Vista, GeneHancer Elite) | DE_00452: chr18: 55401678-55401737; Depression | SE_06352 SE_06762 (Brain - Hippocampus middle) SE_08840 (Brain - Mid frontal lobe) SE_04109 (Brain - Anterior caudate) SE_07745 (Brain - Inferior temporal lobe); SE_04840 (Brain - Cingulate gyrus) SE_03237 (Brain - Angular gyrus) | 1.36E−20; Brain Cingulate Gyrus |
| rs8099160/EUR | DCC_2 (chr18: 52340148-52340207) | Enhancer, prefrontal cortex, cingulate cortex; FANTOM: chr18: 52341963-52342477, eRNA Score: 32, Cells: neural progenitor cells | | | 1E−12; Brain Cingulate Gyrus |
| rs674437-A/EUR | | Enhancer, H1 progenitor neurons; ENSR00000438504 (chr11: 89119401-89120000 | | | 1E−27; Brain Amygdala |
| rs599550-A/EUR | TCF4_2 (chr18: 55588182-55588241) TCF4_3 (chr18: 55588605-55588664) | Enhancer, neural progenitor cells, brain (GeneHancer Elite, Vista, MASTERMIND) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior | 1E−52; Brain Cingulate Gyrus |

TABLE 2A-continued

Part 2. Regulatory element associated with enhancer and superenhancer
SNPs that have been found in the ketamine efficacy sub-network.

| GWAS SNP Reported/ Population(s) | Promoters (EPD new); PromID | Enhancers | Validated casual human disease enhancer- promoter pairs | Superenhancers (dbSUPER) | eQTL |
|---|---|---|---|---|---|
| | | | | caudate), SE_33242 (H1-ESC) | |
| rs7117514- G/EUR | | Enhancer, prefrontal cortex | | | 1E−05; Brain Frontal Cortex |
| rs2163971- T/EUR | | Enhancer, Brain: ENSR00000692682 (chr3: 84983601- 84985999, Type: Proximal) | | | 1E−11; Brain Frontal Cortex |
| rs4936277- A/EUR | ANKK1_1 (chr11: 113387730- 113387789) | Enhancer, H1 neuronal progenitorcells, brain, astrocytes, bipolar neurons; GH11J113505: chr11: 113375857- 113378219; (ENCODE, Ensemble, Vista, MASTERMIND); FANTOM: chr11: 113375857- 113376013 (chr11: 113505135- 113505291, eRNA Score: 2) | | | 1E−06; Brain Hippocampus |
| rs13357015/ EUR | RASG RF2_1 (chr5: 80960623- 80960682) | Enhancer, Bipolar Neuron, Brain, Astrocytes; GH05J080966 | | SE_33104 (Brain - Cingulate gyrus) | 1E−10; Brain Cingulate Gyrus |
| rs17601612- C/EUR | ANKK1_1 (chr11: 113387730- 113387789) | Enhancer, H1 neuronal progenitor cells, brain, astrocytes, bipolar neurons; GH11J113505: chr11: 113375857- 113378219; (ENCODE, Ensemble, Vista, MASTERMIND); FANTOM: chr11: 113375857- 113376013 (chr11: 113505135- 113505291, eRNA Score: 2) | | | 1E−06; Nucleus accumbens |
| rs8084351/ EUR | DCC_2 (chr18: 52340148- 52340207) | Enhancer, prefrontal cortex, cortex; cingulate FANTOM: chr18: 52341963- 52342477, | | SE_08791 (Brain - Mid frontal lobe) | 1.0E−21; Brain Cingiulate Gyrus |

TABLE 2A-continued

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| rs61687445-A/EUR | TTC12_1 (chr11: 113314539-113314598) | eRNA Score: 32, Cells: neural progenitor Enhancer, Bipolar neuron, Brain; ENSR00000045120 (chr11: 113313800-113315601) (ENCODE, FANTOM, Ensmbl) | | | 1E−37; Brain Anterior Caudate |
| rs35738585/ EUR | TTC12_1 (chr11: 113314539-113314598) | Enhancer, Bipolar neuron, Brain; ENSR00000045120 (chr11: 113313800-113315601) (ENCODE, FANTOM, Ensmbl) | | | 1E−37; Brain Anterior Caudate |
| rs9636107-G/EUR | TCF4_2 (chr18: 55588182-55588241) TCF4_3 (chr18: 55588605-55588664) | Enhancer, neural progenitor cells, brain (GeneHancer Elite, Vista, MASTERMIND) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate), SE_33242 (H1-ESC) | 1E−20; Brain Cingulate Gyrus |
| rs12968428-A/EUR | DCC_2 (chr18: 52340148-52340207) | Enhancer, prefrontal cortex, cingulate cortex; FANTOM: chr18: 52341963-52342477, eRNA Score: 32, Cells: neural progenitor cells | | SE_08791 (Brain - Mid frontal lobe) | 1.0E−21; Brain Cingiulate Gyrus |
| rs8138473/ EUR | | Enhancer, neural progenitor cells, brain (GeneHancer Elite, Vista, MASTERMIND) | | SE_08247 (Brain - Inferior temporal lobe) SE_53463 (Spleen) SE_03550 (Brain - Angular gyrus) SE_06357 (Brain - Hippocampus middle) SE_04497 (Brain - Anterior caudate) SE_09211 (Brain - Amygdala) | 1E−20; Brain Amygdala |

TABLE 2A-continued

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| rs619466-G/EUR | TCF4_2 (chr18: 55588182-55588241) TCF4_3 (chr18: 55588605-55588664) | Enhancer, neural progenitor cells, brain (GeneHancer Elite, Vista, MASTERMIND) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate), SE_33242 (H1-ESC) | 1E−20; Brain Cingulate Gyrus |
| rs1431181-A/EUR | DCC_2 (chr18: 52340148-52340207)/ | Enhancer, neural progenitor cell (ENCODE) | | | 1.0E−09; Brain Cingulate Gyrus |
| rs1261070-?/EUR | TCF4_1 (chr18: 55401678-55401737) TCF4_9 (chr18: 55401970-55402029) TCF4_4 (chr18: 55403630-55403689) | Enhancer, prefrontal cortex, cingulate cortex (Vista, GeneHancer Elite) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate) | 1E−11; Brain Frontal Cortex |
| rs611439-?/EUR | TCF4_1 (chr18: 55401678-55401737) TCF4_9 (chr18: 55401970-55402029) TCF4_4 (chr18: 55403630-55403689) | Enhancer, prefrontal cortex, cingulate cortex (Vista, GeneHancer Elite) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate) | 1E−11; Brain Frontal Cortex |
| rs7231748-A/EUR | TCF4_2 (chr18: 55588182-55588241) TCF4_3 (chr18: | Enhancer, neural progenitor cells, brain (GeneHancer Elite, Vista, | DE_00452: chr18: 55401678-55401737; Depression | SE_06758 SE_06128 (Brain - Hippocampus middle); SE_08823 | 1E−20; Brain Cingulate Gyrus |

TABLE 2A-continued

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| | 55588605-55588664) | MASTERMIND) | | (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate), SE_33242 (H1-ESC) | |
| rs4277413-A/EUR | DCC_2 (chr18: 52340148-52340207) | Enhancer, neural progenitor cells, (ENCODE) | | | 1.0E−09; Brain Cingulate Gyrus |
| rs1050316/EUR | MEF2D_2 (chr1: 156490647-156490706) MEF2D_1 (chr1: 156500765-156500824) | Enhancer, bipolar neurons, brain (ENCODE, Ensembl, dbSUPER, GeneHancer Double Eite); FANTOM: chr1: 156502901-156503160, eRNA Score: 319; Cells: Neural progenitor cells | | SE_04141 (Brain - Anterior caudate); SE_08791 (Brain - Mid frontal lobe); SE_05851 SE_06826 (Brain - Hippocampus middle); SE_04925 (Brain - Cingulate gyrus); SE_07824 (Brain - Inferior temporal lobe); SE_03183 (Brain - Angular gyrus); SE_02565 (Astrocytes); | 1E−89; Brain Cingulate Gyrus |
| rs139438618/AFR | SEMA3A_2 (chr7: 84194779-84194838) SEMA3A_1 (chr7: 84194983-84195042) | Enhacner, Bipolar neurons, Brain, neural progenitor cells; ENSR00000214578 (chr7: 84190600-84196801) | — | — | 1E−10; Brain occipital Cortex |
| rs8089865-A/EUR | DCC_2 (chr18: 52340148-52340207) | Enhancer, neural progenitor cell (ENCODE) | | | 1.0E−09; Brain Cingulate Gyrus |
| rs12958048-A/EUR | TCF4_2 (chr18: 55588182-55588241) TCF4_3 (chr18: 55588605-55588664) | Enhancer, neural progenitor cells, brain (GeneHancer Elite, Vista, MASTERMIND) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe) SE_33496 (H2171); SE_03220 (Brain - Angular | 1E−20; Brain Cingulate Gyrus |

TABLE 2A-continued

Part 2. Regulatory element associated with enhancer and superenhancer
SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| rs9636107/ EUR | TCF4_1 (chr18: 55401678-55401737) TCF4_9 (chr18: 55401970-55402029) TCF4_4 (chr18: 55403630-55403689) | Enhancer, prefrontal cortex, cingulate cortex (Vista, GeneHancer Elite) | DE_00452: chr18: 55401678-55401737; Depression | gyrus); SE_04070 (Brain - Anterior caudate) SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate) | 1E−11; Brain Frontal Cortex |
| rs17598729-C/ASN | TCF4_1 (chr18: 55401678-55401737) TCF4_9 (chr18: 55401970-55402029) TCF4_4 (chr18: 55403630-55403689) | Enhancer, prefrontal cortex, cingulate cortex (Vista, GeneHancer Elite) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate) | 1E−11; Brain Frontal Cortex |
| rs4801157/ EUR | TCF4_2 (chr18: 55588182-55588241) TCF4_3 (chr18: 55588605-55588664) | Enhancer, neural progenitor cells, brain (GeneHancer Elite, Vista, MASTERMIND) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe) SE_33496 (H2171); SE_03220 (Brain - Angular gyrus); SE_04070 (Brain - Anterior caudate) | 1E−20; Brain Cingulate Gyrus |
| rs4384683-G/EUR | DCC_2 (chr18: 52340148-52340207) | Enhancer, neural progenitor cell (ENCODE) | | | 1.0E−09; Brain Cingulate Gyrus |
| rs674437-A/EUR | — | Enhancer, H1 progenitor | | | 1E−27; Brain |

TABLE 2A-continued

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| | | neurons; ENSR00000438504 (chr11: 89119401-89120000 | | | Amygdala |
| rs4938021-T/EUR | TMPRSS5_1 (chr11: 113706292-113706351) | Enhancer, neural progenitor cell; GH11J11370: chr11: 113705465-113707068) | | | 1.0E-21; Brain Cingiulate Gyrus |
| rs624244-A/EUR | TCF4_1 (chr18: 55401678-55401737) TCF4_9 (chr18: 55401970-55402029) TCF4_4 (chr18: 55403630-55403689) | Enhancer, prefrontal cortex, cingulate cortex (Vista, GeneHancer Elite) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate) | 1E-11; Brain Frontal Cortex |
| rs674437-M/EUR | | Enhancer, H1 progenitor neurons; ENSR00000438504 (chr11: 89119401-89120000 | | | 1E-27; Brain Amygdala |
| rs7228159-A/EUR | TCF4_1 (chr18: 55401678-55401737) TCF4_9 (chr18: 55401970-55402029) TCF4_4 (chr18: 55403630-55403689) | Enhancer, prefrontal cortex, cingulate cortex (Vista, GeneHancer Elite) | DE_00452: chr18: 55401678-55401737; Depression | SE_06758 SE_06128 (Brain - Hippocampus middle); SE_08823 (Brain - Mid frontal lobe); SE_04894 (Brain - Cingulate gyrus); SE_07784 (Brain - Inferior temporal lobe); SE_03220 (Brain - Angular gyrus); SE_04070 (Brain - Anterior caudate) | 1E-11; Brain Frontal Cortex |
| rs61905363-T/EUR | ANKK1_1 (chr11: 113387730-113387789) | Enhancer, H1 neuronal progenitor cells, brain, astrocytes, bipolar neurons; GH11J113505: chr11: 113375857-113378219; (ENCODE, Ensemble, Vista, | | | 1E-06; Brain Hippocampus |

TABLE 2A-continued

Part 2. Regulatory element associated with enhancer and superenhancer
SNPs that have been found in the ketamine efficacy sub-network.

| GWAS SNP Reported/ Population(s) | Promoters (EPD new); PromID | Enhancers | Validated casual human disease enhancer- promoter pairs | Superenhancers (dbSUPER) | eQTL |
|---|---|---|---|---|---|
| | | MASTERMIND); FANTOM: chr11: 113375857- 113376013 (chr11: 113505135- 113505291, eRNA Score: 2) | | | |
| rs4936277- G/EUR | ANKK1_1 (chr11: 113387730- 113387789) | Enhancer, H1 neuronal progenitor cells, brain, astrocytes, bipolar neurons; GH11J113505: chr11: 113375857- 113378219; (ENCODE, Ensemble, Vista, MASTERMIND); FANTOM: chr11: 113375857- 113376013 (chr11: 113505135- 113505291, eRNA Score: 2) | | | 1E−06; Brain Hippocampus |
| rs17041417- A/EUR | | Enhancer, neural stem progenitor cell | | | 1E−16; Brain Amygdala |
| rs17041417- A/EUR | | Enhancer, neural stem progenitor cell | | | 1E−16; Brain Amygdala |
| rs17041417- A/EUR | | Enhancer, neural stem progenitor cell | | | 1E−16; Brain Amygdala |
| rs9811546- A/EUR | | Enhancer, Brain: ENSR00000692682 (chr3: 84983601- 84985999, Type: Proximal) | | | 1E11; Brain Cingulate Gyrus |
| rs17041417- A/EUR | | Enhancer, Brain: ENSR00000692682 (chr3: 84983601- 84985999, Type: Proximal) | | | 1E−16; Brain Amygdala |
| rs12575685/ EUR | | Enhancer, brain (chr11: 70367951- 70368077) FANTOM, Ensembl, VISTA | | SE_69042 (H9 neurons) | |
| rs2274316- C/EUR | MEF2D_2 (chr1: 156490647- 156490706) MEF2D_1 (chr1: 156500765- 156500824) | Enhancer, bipolar neurons, brain (ENCODE, Ensembl, dbSUPER, GeneHancer Double Eite); FANTOM: chr1: 156502901- | | SE_04141 (Brain - Anterior caudate); SE_08791 (Brain - Mid frontal lobe); SE_05851 SE_06826 (Brain - Hippocampus middle); | 1E−89; Brain Cingulate Gyrus |

TABLE 2A-continued

Part 2. Regulatory element associated with enhancer and superenhancer
SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| | | 156503160, eRNA Score: 319; Cells: Neural progenitor cells | | SE_04925 (Brain - Cingulate gyrus); SE_07824 (Brain - Inferior temporal lobe); SE_03183 (Brain - Angular gyrus); SE_02565 (Astrocytes); SE_33104 (Brain - Cingulate gyrus) | |
| rs775766-A/EUR | | Enhancer, neural stem progenitor cell, embryonic human cerebral cortex | | | |
| rs310763-C/EUR | PPARG_2 (chr3: 12287875-12287934) PPARG_3 (chr3: 12288326-12288385) PPARG_1 (chr3: 12289021-12289080) | Enhancer, bipolar neurons, brain (ENCODE, Ensembl, dbSUPER, GeneHancer Double Eite); FANTOM: chr1: 156502901-156503160, eRNA Score: 319; Cells: Neural progenitor cells | | | |
| rs310763-C/EUR | PPARG_2 (chr3: 12287875-12287934) PPARG_3 (chr3: 12288326-12288385) PPARG_1 (chr3: 12289021-12289080) | Enhancer, bipolar neurons, brain (ENCODE, Ensembl, dbSUPER, GeneHancer Double Eite); FANTOM: chr1: 156502901-156503160, eRNA Score: 319; Cells: Neural progenitor cells | | | |
| rs310763-C/EUR | PPARG_2 (chr3: 12287875-12287934) PPARG_3 (chr3: 12288326-12288385) PPARG_1 (chr3: 12289021-12289080) | Enhancer, bipolar neurons, brain (ENCODE, Ensembl, dbSUPER, GeneHancer Double Eite); FANTOM: chr1: 156502901-156503160, eRNA Score: 319; Cells: Neural progenitor cells | | | |
| rs1016306-T/EUR | — | Enhancer, Brain: ENSR00000692682 (chr3: 84983601-84985999, Type: Proximal) | — | — | |
| rs935526-T/EUR | | Enhancer, fronatl cortex, | | SE_33104 (Brain - Cingulate | |

TABLE 2A-continued

Part 2. Regulatory element associated with enhancer and superenhancer SNPs that have been found in the ketamine efficacy sub-network.

| GWAS SNP Reported/ Population(s) | Promoters (EPD new); PromID | Enhancers | Validated casual human disease enhancer-promoter pairs | Superenhancers (dbSUPER) | eQTL |
|---|---|---|---|---|---|
| rs161645-A/EUR | | cingulate cortex, neurons; ENSR00000691539 (chr3: 75936001-75936200, | | gyrus) | |
| rs17211233-T/EUR | RASGRF21 (chr5: 80960623-80960682) | Enhancer, Bipolar Neuron, Brain, Astrocytes; GH05J080966 | | SE_33104 (Brain - Cingulate gyrus) | |
| rs11214606/ EUR | TMPRSS5_1 (chr11: 113706292-113706351) | Enhancer, neural progenitor cell; GH11J11370: chr11: 113705465-113707068) | | | 1.0E-21; Brain Anterior Caudate |
| rs1400237/ EUR | | Enhancer, fronatl cortex, cingulate cortex, neurons; ENSR00000691539 (chr3: 75936001-75936200, | | SE_33104 (Brain - Cingulate gyrus) | |
| rs1846786-T/EUR | | | | | |
| rs4855976/ EUR | | Enhancer, fronatl cortex, cingulate cortex, neurons; ENSR00000691539 (chr3: 75936001-75936200, | | SE_33104 (Brain - Cingulate gyrus) | |
| rs79749176-A/EUR | SLC2 2A15_1 (chr1: 115976484-115976543) | Enhancer, frontal cortex (chr1: 116520279-116520650) | | SE_06669 SE_06902 (Brain - Hippocampus middle) SE_05076 (Brain - Cingulate gyrus) SE_09933 (CD14+ monocytes) SE_03600 (Brain - Angular gyrus) SE_04498 (Brain - Anterior caudate) SE_08098 (Brain - Inferior temporal lobe) | 1E-08; Brain Anterior Caudate |

TABLE 2A

Part 3. Chromatin interactions for enhancer and superenhancer SNPs that have been found in the ketamine efficacy sub-network..

| GWAS SNP Reported/ Population(s) | Hi-C Score | HGREEN score | Enhancer RNA co-expression p-value | Judged by machine learning to be causal in neural cell lines but not HepG2? |
|---|---|---|---|---|
| rs7623659-T/ EUR | 0.0001: Cingulate cortex | 1.00E−12 | 2.00E−06 | Yes |
| rs12229654-G/ ASN | 0.0001: Frontal cortex | 1.00E−18 | 2.20E−09 | Yes |
| rs30266-A/ EUR | 0.01: Frontal cortex | | | Yes |
| rs61902811-G/ EUR | 0.0001: Hipoocampus | 1.00E−07 | | Yes |
| rs12229654-G/ ASN | 0.001: Frontal cortex | 1.00E−18 | 2.20E−23 | Yes |
| rs6265-T/ EUR | | 1.10E−10 | | Yes |
| rs7227069-A/ EUR | 0.0000000001: Cingulate cortex | 1.50E−20 | 1.00E−05 | Yes |
| rs12967143-G/ EUR | 0.0000000001: Frontal cortex | 1.00E−05 | 1.10E−10 | Yes |
| rs4938021-T/ EUR | 0.0000000001: Amygdala | | | Yes |
| rs6589377-A/ EUR | 0.0001: Hippocampus | 1.00E−07 | | |
| rs6589377-A/ EUR | 0.00000000011: Cingulate cortex | 1.00E−10 | | Yes |
| rs7932640-T/ EUR | 0.0001: Cingulate cortex | 1.50E−10 | | Yes |
| rs7111031-A/ EUR | 0.00000000011: Anterior caudate | | | Yes |
| rs11662271-T/ EUR | 0.00000000011: Frontal cortex | 1.00E−07 | | Yes |
| rs1373178-G/ EUR | 0.0001: Amygdala | 1.50E−10 | | Yes |
| rs1925950-G/ EUR | 0.0000000001: Cingulate cortex | | 6.10E−11 | Yes |
| rs8084280-T/ EUR | 0.0000000001: Cingulate cortex | | 6.30E−10 | No |
| rs7111031-A/ EUR | 0.0000001: Hippocampus | | 3.30E−06 | Yes |
| rs1925950-G/ EUR | 0.00000000000000000000000000000011: Cingulate cortex | | 6.10E−11 | Yes |
| rs12520354-A/ EUR | 0.0000000001: Cingulate cortex | | | Yes |
| rs599550-A/ EUR | 0.00000000011: Frontal cortex | 2.00E−05 | | Yes |
| rs613872-C/ EUR | 0.0001: Cingulate cortex | | | Yes |
| rs8084280-T/ EUR | 0.00000000011: Cingulate cortex | | 6.30E−10 | Yes |
| rs11662271-T/ EUR | 0.0000000001: Frontal cortex | 1.00E−07 | | Yes |
| rs12967143-C/ EUR | 0.0000000001: Frontal cortex | 1.00E−05 | 1.10E−10 | Yes |
| rs8181326-A/ EUR | 0.00000001: Cingulate cortex | | | Yes |
| rs72930774-A/ EUR | 0.0000000001: Frontal cortex | 1.00E−05 | 1.10E−10 | Yes |
| rs2958162/ EUR | 0.0000000001: Cingulate cortex | | | Yes |
| rs7949802-T/ EUR | 0.0000000001: Hippocampus | | 3.30E−06 | Yes |
| rs1660237-T/ EUR | 0.00001: Frontal cortex | | | Yes |
| rs674437-A/ EUR | 0.0000000001: Amygdala | 1.80E−09 | | Yes |
| rs624244/ EUR | 0.0000000001: Cingulate cortex | | | Yes |
| rs8099160/ EUR | 0.0000000001: Cingulate cortex | 1.00E−07 | 1.00E−21 | Yes |

TABLE 2A-continued

Part 3. Chromatin interactions for enhancer and superenhancer SNPs that have been found in the ketamine efficacy sub-network..

| GWAS SNP Reported/ Population(s) | Hi-C Score | HGREEN score | Enhancer RNA co-expression p-value | Judged by machine learning to be causal in neural cell lines but not HepG2? |
|---|---|---|---|---|
| rs674437-A/ EUR | 0.0000000001: Amygdala | 1.80E−09 | | Yes |
| rs599550-A/ EUR | 0.0000000001: Cingulate cortex | 2.00E−05 | | |
| rs7117514-G/ EUR | 0.001: Frontal cortex | | | Yes |
| rs2163971-T/ EUR | 0.00000001: Frontal cortex | | | |
| rs4936277-A/ EUR | 0.000001: Nucleus Accumbens | | 4.00E−05 | |
| rs13357015/ EUR | 0.0001: Cingulate cortex | | | Yes |
| rs17601612-C/ EUR | 0.000001: Nucleus Accumbens | | 4.00E−05 | |
| rs8084351/ EUR | 0.0000000001: Cingulate cortex | 1.50E−20 | 1.00E−05 | Yes |
| rs61687445-A/ EUR | 0.0000000001: Anterior caudate | | | Yes |
| rs35738585/ EUR | 0.0000000001: Anterior caudate | | | |
| rs9636107-G/ EUR | 0.0000000001: Cingulate cortex | 2.00E−05 | | |
| rs12968428-A/ EUR | 0.0000000001: Cingulate cortex | 1.50E−20 | 1.00E−05 | |
| rs8138473/ EUR | 0.000000001: Amygdala | 1.00E−04 | | Yes |
| rs619466-G/ EUR | 0.0000000001: Cingulate cortex | 2.00E−05 | | Yes |
| rs1431181-A/ EUR | 0.0000000001: Cingulate cortex | | 6.30E−10 | Yes |
| rs1261070-?/ EUR | 0.000000001: Frontal cortex | 1.00E−05 | 1.10E−10 | Yes |
| rs611439-?/ EUR | 0.00001: Frontal cortex | 1.00E−05 | 1.10E−10 | Yes |
| rs7231748-A/ EUR | 0.0000000001: Cingulate cortex | 2.00E−05 | 1.00E−11 | Yes |
| rs4277413-A/ EUR | 0.0000000001: Cingulate cortex | | 6.30E−10 | Yes |
| rs1050316/ EUR | 0.000001: Cingulate cortex | | 6.10E−11 | Yes |
| rs139438618/ AFR | 0.0000000001: Nucleus Accumbens | — | — | Yes |
| rs8089865-A/ EUR | 0.00000001: Cingulate cortex | | 6.30E−10 | Yes |
| rs12958048-A/ EUR | 0.0000000001: Cingulate cortex | 2.00E−05 | 1.00E−11 | Yes |
| rs9636107/ EUR | 0.0000000001: Frontal cortex | 1.00E−05 | 1.10E−10 | Yes |
| rs17598729-C/ ASN | 0.0000000001: Frontal cortex | 1.00E−05 | 1.10E−10 | Yes |
| rs4801157/ EUR | 0.0000000001: Cingulate cortex | 2.00E−05 | 1.00E−11 | Yes |
| rs4384683-G/ EUR | 0.0000000001: Cingulate cortex | | 6.30E−10 | Yes |
| rs674437-A/ EUR | 0.0000000001: Amygdala | 1.80E−09 | — | |
| rs4938021-T/ EUR | 0.0000000001: Cingulate cortex | 1.00E−10 | — | Yes |
| rs624244-A/ EUR | 0.0000000001: Frontal cortex | 1.00E−05 | 1.10E−10 | Yes |
| rs674437-A/ EUR | 0.0000000001: Amygdala | 1.80E−09 | | |
| rs7228159-A/ EUR | 0.0000000001: Frontal cortex | 1.00E−05 | 1.10E−10 | Yes |
| rs61905363-T/ EUR | 0.0000000001: Hippocampus | | 4.00E−05 | Yes |

TABLE 2A-continued

Part 3. Chromatin interactions for enhancer and superenhancer SNPs that have been found in the ketamine efficacy sub-network..

| GWAS SNP Reported/ Population(s) | Hi-C Score | HGREEN score | Enhancer RNA co-expression p-value | Judged by machine learning to be causal in neural cell lines but not HepG2? |
|---|---|---|---|---|
| rs4936277-G/ EUR | 0.0000000001: Hippocampus | | 8.00E−08 | Yes |
| rs17041417-A/ EUR | 0.0000000001: Amygdala | | 5.00E−11 | Yes |
| rs17041417-A/ EUR | 0.0000000001: Amygdala | | 5.00E−11 | Yes |
| rs17041417-A/ EUR | 0.0000000001: Amygdala | | 5.00E−11 | |
| rs9811546-A/ EUR | 0.0000000001: Cingulate cortex | | 6.10E−11 | Yes |
| rs17041417-A/ EUR | 0.0000000001: Amygdala | | 1.00E−11 | |
| rs12575685/ EUR | 0.000000001: Fetal brain, female | | 5.00E−07 | Yes |
| rs2274316-C/ EUR | 0.0000000001: Cingulate cortex | | 6.10E−11 | Yes |
| rs775766-A/ EUR | 0.00000000000001: Cingulate cortex | 1.00E−10 | | Yes |
| rs310763-C/ EUR | 0.0000000001: Frontal cortex | | | Yes |
| rs310763-C/ EUR | 0.0000000001: Frontal cortex | | | |
| rs310763-C/ EUR | 0.0000000001: Frontal cortex | | | |
| rs1016306-T/ EUR | 0.0000000001: Amygdala | — | — | Yes |
| rs935526-T/ EUR | 0.01: Cingulate cortex | 1.00E−10 | | Yes |
| rs161645-A/ EUR | | | | Yes |
| rs17211233-T/ EUR | 0.00000000000000000000000001: Cingulate cortex | 1.00E−10 | 2.00E−05 | Yes |
| rs11214606/ EUR | 0.0000000001: Anterior caudate | | 5.00E−18 | Yes |
| rs1400237/ EUR | 0.000000001: Cingulate cortex | 1.00E−10 | | Yes |
| rs1846786-T/ EUR | | | | Yes |
| rs4855976/ EUR | 0.000000001: Cingulate cortex | 1.00E−10 | | Yes |
| rs79749176-A/ EUR | 0.0000000001: Anterior caudate | 1.00E−10 | | Yes |

TABLE 2B

Part 1. Enhancer and superenhancer SNPs that have been found in the ketamine adverse event sub-network.

| GWAS SNP Reported/ Population(s) | Reported gene(s) | Variant type | Reported trait | P-value | Odds ratio or beta | Confidence Interval (95%) | PubMed ID | EBI-NHGRI Accension Number |
|---|---|---|---|---|---|---|---|---|
| rs1051730-A/ASN, EUR | CHRNA5, CHRNA3 | Intergenic | Smoking status | 6.00E−121 | 0.1 unit increase | [0.091-0.111] | 30617275 | GCST007602 |
| rs1051730-G/EUR | CHRNA5, CHRNA3 | Intergenic | Smoking status | 3.00E−73 | 1.02 CPD decrease | [0.91-1.13] | 20418890 | GCST000666 |
| rs1051730-A/EUR | CHRNA5, CHRNA3 | Intergenic | Smoking status | 7.00E−69 | 0.8 CPD increase | [0.70-0.90] | 20418888 | GCST000667 |
| rs1051730-G/EUR | CHRNA5, CHRNA3 | Intergenic | Smoking status | 2.00E−66 | 0.08 unit decrease | [0.07-0.09] | 20418889 | GCST000668 |

TABLE 2B-continued

Part 1. Enhancer and superenhancer SNPs that have been found in the ketamine adverse event sub-network.

| GWAS SNP Reported/ Population(s) | Reported gene(s) | Variant type | Reported trait | P-value | Odds ratio or beta | Confidence Interval (95%) | PubMed ID | EBI-NHGRI Accession Number |
|---|---|---|---|---|---|---|---|---|
| rs2155646-C/EUR | NCAM1 | Intragenic | Smoking status | 3.00E−61 | 0.0181277 unit increase | [0.016-0.02] | 30643251 | GCST007468 |
| rs7938812-T/EUR | NCAM1 | Intragenic | Smoking status | 7.00E−48 | 0.029930087 unit decrease | [0.026-0.034] | 30643258 | GCST007474 |
| rs3130820/EUR | TRIM28 | Intergenic | Schizophrenia, chronic (F20) | 2.00E−44 | 1.281 | [1.25-1.32] | 29483656 | GCST006803 |
| rs3918226-T/EUR | NOS3 | Intragenic | Medication use (agents acting on the renin-angiotensin system) | 2.00E−37 | 0.145321 unit increase | [0.12-0.17] | 31015401 | GCST007930 |
| rs3918226/EA (Han Chinese) | NOS3 | Intragenic | Diastolic blood pressure and smoking status | 4.00E−33 | | | 29455858 | GCS006187 |
| rs3918226-T/AFR, AMR, ASN, EUR | NOS3 | Intragenic | Diastolic blood pressure × alcohol consumption interaction (2df test) | 4.00E−31 | | | 29912962 | GCST006166 |
| rs3918226-T/EUR | NOS3 | Intragenic | Medication use (diuretics) | 7.00E−29 | 0.1665414 unit increase | [0.14-0.2] | 31015401 | GCST007928 |
| rs3918226-T/EUR | NOS3 | Intragenic | Medication use (calcium channel blockers) | 4.00E−26 | 0.16126491 unit increase | [0.13-0.19] | 31015401 | GCST007929 |
| rs2155290/EUR | NCAM1 | Intragenic | Risk-taking behavior | 4.00E−24 | 0.026843483 unit decrease | [0.022-0.032] | 30643258 | GCST007323 |
| rs182812355-A/ASN | TRIM27, TRIM28 | Intergenic | Schizophrenia, chronic (F20) | 7.00E−23 | 1.206 | [1.17-1.24 | 30285260 | GCST007201 |
| rs3918226-T/EUR | NOS3 | Intragenic | Medication use (beta blocking agents) | 8.00E−21 | 0.14636576 unit increase | [0.12-0.18] | 31015401 | GCST007927 |
| rs12764899/EUR | BORCS7-ASMT, AS3MT | Intergenic | Cognitive ability, years of educational attainment or schizophrenia (pleiotropy) | 3.00E−20 | 0.02186565 unit increase | [0.017-0.027] | 31374203 | GCST008595 |
| rs11191424-G/EUR | BORCS7-ASMT, AS3MT | Intergenic | Schizophrenia, chronic (F20) | 4.00E−20 | 1.0905125 | [1.07-1.11] | 28991256 | GCST004946 |
| rs2007044/ASN | CACNA1C | Intragenic | Schizophrenia, chronic (F20) | 6.00E−20 | 1.0928961 | 1.07-1.11 | 29483656 | GCST006803 |
| rs2159100/ASN, EUR | CACNA1C | Intragenic | Schizophrenia, chronic (F20) | 3.00E−19 | 1.102 | 1.08-1.12 | 28991256 | GCST004946 |
| rs514465-A/EUR | GABRA2 | Intragenic | Risk-taking behavior | 2.00E−18 | 0.0104 unit increase | 0.008-0.0128 | 30643258 | GCST007323 |
| rs2007044-G/ASN, EUR | CACNA1C | Intragenic | Schizophrenia, chronic (F20) | 3.00E−18 | 1.0964912 | [1.07-1.12] | 25056061 | GCST002539 |
| rs1024582-A/ASN | CACNA1C | Intragenic | Schizophrenia, chronic (F20) | 9.00E−18 | 1.1037527 | 1.08-1.13 | 30285260 | GCST007201 |
| rs2007044/EUR | CACNA1C | Intragenic | Schizophrenia, chronic (F20) | 1.00E−17 | 1.098901 | | 26198764 | GCST002539 |
| rs10774909/EUR | NOS1 | Intragenic | Neuroticism, general | 5.00E−16 | 0.009250518 unit increase | 0.007-0.0115 | 30643256 | GCST007339 |
| rs2007044/EUR | CACNA1C | Intragenic | Cognitive ability, years of | 2.00E−15 | 0.016178014 unit increase | [0.012-0.02] | 31374203 | GCST008595 |

TABLE 2B-continued

Part 1. Enhancer and superenhancer SNPs that have been found in the ketamine adverse event sub-network.

| GWAS SNP Reported/ Population(s) | Reported gene(s) | Variant type | Reported trait | P-value | Odds ratio or beta | Confidence Interval (95%) | PubMed ID | EBI-NHGRI Accession Number |
|---|---|---|---|---|---|---|---|---|
| | | | educational attainment or schizophrenia (pleiotropy) | | | | | |
| rs7192140 | GRIN2A | Intra genic | Smoking status | 2.00E-15 | 0.00854911 unit decrease | [0.0064-0.0107] | 30643251 | GCST007468 |
| rs2239030-A/EUR | CACNA1C | Intra genic | Risk-taking behavior | 6.00E-15 | 0.0093 unit increase | 0.0069-0.0117 | 30643258 | GCST007323 |
| rs3918226-T/EA (Han Chinese) | NOS3 | Intra genic | Systolic blood pressure × alcohol consumption interaction (2df test) | 2.00E-14 | | | 29912962 | GCST006434 |
| rs11055991-A/EUR | ATF7IP | Intra genic | Cognitive performance (MTAG) | 5.00E-14 | 0.0175 unit decrease | [0.013-0.022] | 30038396 | GCST006570 |
| rs2007044/ EUR | CACNA1C | Intra genic | Autism spectrum disorder or schizophrenia | 6.00E-14 | 1.0752687 | 1.05-1.1 | 28540026 | GCST004521 |
| rs1024582-A/EUR | CACNA1C | Intra genic | Autism spectrum disorder or schizophrenia | 8.00E-14 | 1.093 | | 28540026 | GCST004521 |
| rs7893279-T/ASN, EUR | CACNB2 | Intra genic | Schizophrenia, chronic (F20) | 9.00E-14 | 1.122 | 1.09-1.15 | 30285260 | GCST007201 |
| rs8042374-A/EA (Han Chinese) | CHRNA3 | Intra genic | Schizophrenia, chronic (F20) | 2.00E-13 | 1.093 | [1.067-1.119] | 28991256 | GCST004946 |
| rs7893279-T/ASN, EUR | CACNB2 | Intra genic | Schizophrenia, chronic (F20) | 3.00E-13 | 1.117 | [1.09-1.15] | 28991256 | GCST004946 |
| rs7893279-T, ASN, EUR | CACNB2 | Intra genic | Schizophrenia, chronic (F20) | 5.00E-13 | 1.118 | [1.09-1.15] | 28991256 | GCST004946 |
| rs1006737/ EUR | CACNA1C | Intra genic | Schizophrenia or bipolar I disorder | 6.00E-13 | | | 24280982 | GCST002295 |
| rs28681284-C/ASN | CHRNA5, CHRNA3 | Inter genic | Schizophrenia, chronic (F20) | 6.00E-13 | 1.121 | 1.09-1.15 | 30285260 | GCST007201 |
| rs7893279-T/ASN, EUR | CACNB2 | Intra genic | Schizophrenia, chronic (F20) | 9.00E-13 | 1.117 | 1.09-1.15 | 28991256 | GCST004946 |
| rs3918226/ EUR | NOS3 | Intra genic | Systolic blood pressure (cigarette smoking interaction) | 2.00E-12 | | | 29455858 | GCST006188 |
| rs7893279-T/ASN (Han Chinese), EUR | CACNB2 | Intra genic | Schizophrenia, chronic (F20) | 2.00E-12 | 1.125 | [1.088-1.162] | 25056061 | GCST002539 |
| rs1006737-A/EUR | CACNA1C | Intra genic | Schizophrenia, chronic (F20) | 5.00E-12 | 1.103 | [1.08-1.13] | 23974872 | GCST002149 |
| rs111294930-A/EUR | LINC01470, GRIA1 | Inter genic | Schizophrenia, chronic (F20) | 9.00E-12 | 1.086 | [1.06-1.11] | 29483656 | GCST006803 |
| rs7688285-C/AFR, EUR | GLRB | Intronic | Panic disorder, startle response, fear | 7.00E-12 | 1.50163 unit increase | 1.27-1.67 | 28167838 | |
| rs641574-A/ EUR | GRIA4 | Intra genic | Cognitive function | 1.00E-11 | 0.016 unit decrease | 0.011-0.021 | 30038396 | GCST006570 |
| rs2298527- | NCAM1 | Intra | Increased | 3.00E-11 | 6.653 z | | 29255261 | GCST005232 |

TABLE 2B-continued

Part 1. Enhancer and superenhancer SNPs that have been found in the ketamine adverse event sub-network.

| GWAS SNP Reported/ Population(s) | Reported gene(s) | Variant type | Reported trait | P-value | Odds ratio or beta | Confidence Interval (95%) | PubMed ID | EBI-NHGRI Accession Number |
|---|---|---|---|---|---|---|---|---|
| C/EUR | | genic | neuroticism | | score decrease | | | |
| rs7192140-C/EUR | GRIN2A | Intra genic | Smoking status | 3.00E−11 | 0.016883379 unit decrease | [0.012-0.022] | 30643251 | GCST007468 |
| rs9292918-G/ASN | HCN1 | Intra genic | Schizophrenia, chronic (F20) | 4.00E−11 | 1.0729614 unit increase | 1.05-1.09 | 28991256 | GCST004946 |
| rs2155290-C/EUR | NCAM1 | Intra genic | Risky sexual behavior measurement | 5.00E−11 | 0.015957858 unit decrease | [0.011-0.021] | 30643258 | GCST007326 |
| rs16902086/ EUR | HCN1 | Intra genic | Schizophrenia, chronic (F20) | 6.00E−11 | 1.0683761 unit increase | 1.05-1.09 | 29283656 | GCST006803 |
| rs7893279-T/ASN (Han Chinese), EUR | CACNB2 | Intra genic | Schizophrenia, chronic (F20) | 6.00E−11 | 1.12 | | 26198764 | GCST003048 |
| rs2239030-A/EUR | CACNA1C | Intra genic | Risk-taking behavior | 7.00E−11 | 0.012764932 unit increase | 0.0089-0.0166 | 30643258 | GCST007323 |
| rs1837016-T/EUR | NQO1 | Intra genic | Risk-taking tendency (4-domain principal component model) | 7.00E−11 | 0.017263984 unit decrease | [0.012-0.022] | 30643258 | GCST007323 |
| rs111294930-A/ASN, EUR | LINC01470, GRIA1 | Inter genic | Schizophrenia, chronic (F20) | 1.00E−10 | 1.094 | [1.064-1.124] | 25056061 | GCST002539 |
| rs62367520/ EUR | HCN1 | Intra genic | Smoking status | 1.00E−10 | 0.186 | | 29283656 | GCST007468 |
| rs11647445-G/EUR | GRIN2A | Intra genic | Bipolar I disorder | 1.00E−10 | 1.0785276 | | 31043756 | GCST008103 |
| rs7893279-T/ASN (Han Chinese), EUR | CACNB2 | Intra genic | Schizophrenia, chronic (F20) | 1.00E−10 | 1.119 | [1.08-1.15] | 30285260 | GCST007201 |
| rs4782271-A/EUR | GRIN2A | Intra genic | Risk-taking behavior | 2.00E−10 | 0.01 unit increase | [0.0069-0.0131] | 30643258 | GCST007325 |
| rs7893279-T/EUR | CACNB2 | Intra genic | Schizophrenia, autism spectrum disorder | 3.00E−10 | 1.1 | [1.07-1.14] | 28540026 | GCST004521 |
| rs73047488/ EUR | GRIN2B | Intra genic | Risk-taking behavior | 3.00E−10 | 0.0078 unit increase | 0.0054-0.0102 | 30643258 | GCST007325 |
| rs3825845-C/ASN | CHRNA3 | Intra genic | Schizophrenia, chronic (F20) | 4.00E−10 | 1.12 | | 30285260 | GCST007201 |
| rs10744560/ EUR | CACNA1C, CACNA1C-IT3 | Intra genic | Bipolar I, II disorder | 4.00E−10 | 1.07595 | [1.05-1.1] | 31043756 | GCST008103 |
| rs113551349/ EUR | SLC6A9 | Intra genic | ADHD and lifetime cannabis use | 5.00E−10 | 1.098901 | [1.08-1.14] | 30610198 | GCST006983 |
| rs2973155-C/EUR | GRIA1, LINC01470 | Inter genic | Schizophrenia, chronic (F20) | 8.00E−10 | 1.0638298 | | 26198764 | GCST003048 |
| rs13233131/ EUR | CHRM2 | Intra genic | Risk-taking behavior | 8.00E−10 | 0.0095 unit decrease | [0.0066-0.0124] | 30643258 | GCST007325 |
| rs758117-C/ASN | CACNA1C | Intra genic | Schizophrenia, chronic (F20) | 8.00E−10 | 1.0695187 | [1.05-1.09] | 30285260 | GCST007201 |
| rs872123/ EUR | GAD1 | Intra genic | Cognitive function | 1.00E−09 | 0.0208 unit increase | [0.014-0.027] | 30038396 | GCST006572 |
| rs2973155-C/EUR | GRIA1 | Intra genic | Schizophrenia, chronic (F20) | 1.00E−09 | 1.0638298 | | 26198764 | GCST003048 |
| rs13176930-T/ASN | LINC01470, GRIA1 | Inter genic | Schizophrenia, chronic (F20) | 1.00E−09 | 1.0718113 | 1.05-1.09 | 26198764 | GCST007201 |
| rs9292918/ | HCN1 | Intra | Schizophrenia, | 1.00E−09 | 1.0683761 | [1.05-1.09] | 29283656 | GCST007201 |

TABLE 2B-continued

Part 1. Enhancer and superenhancer SNPs that have been found in the ketamine adverse event sub-network.

| GWAS SNP Reported/ Population(s) | Reported gene(s) | Variant type | Reported trait | P-value | Odds ratio or beta | Confidence Interval (95%) | PubMed ID | EBI-NHGRI Accession Number |
|---|---|---|---|---|---|---|---|---|
| EUR | | genic | chronic (F20) | | | | | |
| rs1478364-T/EUR | GRIA1, LINC01470 | Intragenic | Risk-taking behavior | 2.00E−09 | 0.0091 unit decrease | [0.0062-0.012] | 30643258 | GCST007325 |
| rs9922678 (rs9926303)/ EUR | GRIN2A | Intragenic | Schizophrenia, chronic (F20) | 2.00E−09 | 1.07 | | 26198764 | GCST003048 |
| rs7191183/ EUR | GRIN2A | Intragenic | Autism spectrum disorder or schizophrenia | 2.00E−09 | 1.0638298 | [1.04-1.09] | 28540026 | GCST004521 |
| rs9922678-A/ASN, EUR | GRIN2A | Intragenic | Schizophrenia, chronic (F20) | 3.00E−09 | 1.065 | [1.04-1.09] | 28991256 | GCST004946 |
| rs17504622-T/ASN, EUR | GRIN2A | Intragenic | Schizophrenia, chronic (F20) | 3.00E−09 | 1.238 | [1.17-1.31] | 28991256 | GCST004946 |
| rs728022696/ EUR | LINC01470, GRIA1 | Intragenic | Schizophrenia, chronic (F20) | 3.00E−09 | 1.24 | [1.17-1.31] | 23974872 | GCST002149 |
| rs4765913/ EUR | CACNA1C | Intragenic | Bipolar I, II disorder | 3.00E−09 | 1.13 | | 28072414 | GCST003962 |
| rs9922678/ ASN, EUR | GRIN2A | Intragenic | Schizophrenia, chronic (F20) | 3.00E−09 | | | 28991256 | |
| rs13176930/ EUR | GRIA1, LINC01470 | Intergenic | Schizophrenia, chronic (F20) | 1.00E−09 | 1.0638298 | | 26198764 | GCST003048 |
| rs117578877-T/EUR | GRIN2B | Intragenic | Risk-taking behavior | 4.00E−09 | | | 30643258 | GCST007324 |
| rs1501357-C/ASN, EUR | HCN1 | Intragenic | Schizophrenia, chronic (F20) | 5.00E−09 | 1.08E+00 | [1.05-1.11] | 25056061 | GCST002539 |
| rs4765914/ EUR | CACNA1C | Intragenic | Bipolar disorder | 5.00E−09 | | | 30626913 | |
| rs1006737/ EUR | CACNA1C | Intragenic | Attention deficit hyperactivity disorder, unipolar depression, schizophrenia, autism spectrum disorder, bipolar disorder | 5.00E−09 | 1.071 | [1.05-1.10] | 23453885 | GCST001877 |
| rs9922678-A/ASN | GRIN2A | Intragenic | Schizophrenia, chronic (F20) | 6.00E−09 | 1.0708 | [1.05-1.09] | 30285260 | GCST007201 |
| rs10744560-T | CACNA1C, CACNA1C-IT3 | Intergenic | Bipolar I disorder | 8.00E−09 | 1.123444 | | 31043756 | GCST008115 |
| rs1501357-C/EUR | HCN1 | Intragenic | Schizophrenia, chronic (F20) | 1.00E−08 | 1.0752687 | | 29283656 | GCST003048 |
| rs9922678-A/ASN, EUR | GRIN2A | Intragenic | Schizophrenia, chronic (F20) | 1.00E−08 | 1.062 | [1.04-1.08] | | GCST007201 |
| rs68081839/ EUR | GRIA4 | Intragenic | Nicotine dependence and major depression | 2.00E−08 | 0.6587 unit increase | [0.43-0.89] | 30287806 | GCST006631 |
| rs28607014-C/EA (Han Chinese) | NOS1 | Intragenic | Schizophrenia, chronic (F20) | 2.00E−08 | 1.0570824 | [1.04-1.08] | 28991256 | GCST004946 |
| rs12522290-C/EUR | LINC01470, GRIA1 | Intergenic | Autism spectrum disorder, schizophrenia | 2.00E−08 | 1.08 | [1.05-1.11] | 28540026 | GCST004521 |
| rs1006737-A/EUR | CACNA1C | Intragenic | Bipolar II disorder or major | 3.00E−08 | | | 20351715 | GCST000641 |

TABLE 2B-continued

Part 1. Enhancer and superenhancer SNPs that have been found in the ketamine adverse event sub-network.

| GWAS SNP Reported/ Population(s) | Reported gene(s) | Variant type | Reported trait | P-value | Odds ratio or beta | Confidence Interval (95%) | PubMed ID | EBI-NHGRI Accension Number |
|---|---|---|---|---|---|---|---|---|
| | | | depressive disorder | | | | | |
| rs73568641-C/AFR | OPRM1 | Intra genic | Methadone maintenance, heroin addiction | 3.00E−08 | 0.6808 unit increase | [0.44-0.92] | 26377243 | GCST004136 |
| rs13170232-T/EUR | GRIA1 | Intra genic | Schizophrenia, chronic (F20) | 5.00E−08 | 1.098901 | | 26198764 | GCST003048 |
| rs9292918/EUR | HCN1 | Intra genic | Autism spectrum disorder, schizophrenia | 5.00E−08 | 1.0638298 | [1.04-1.1] | 28540026 | GCST004521 |
| rs12522290-C | GRIA1 | Intra genic | Schizophrenia, chronic (F20) | 5.00E−08 | 1.08 | | 26198764 | GCST003048 |
| rs13008299-G/EUR | TOGARAM2 | Intra genic | Diastolic blood pressure and alcoholism | 7.00E−07* | 0.068 unit decrease | 0.033-0.103 | 24376456 | GCST002309 |
| rs117578877-T/EUR | AC007527.1, GRIN2B | Inter genic | Schizophrenia, chronic (F20) | 9.00E−07* | 1.15 | | 26198764 | GCST003048 |
| rs11127199-G/EUR | TOGARAM2 | Intra genic | Response to ketamine in bipolar disorder or major depression (increase, dissociation effects) | 7.00E−06* | 11.445 unit increase | 6.82-16.07 | 30552317 | GCST007317 |

TABLE 2B

Part 2. Regulatory elements associated with enhancer and superenhancer SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| rs1051730-A/ASN, EUR | CHRNA3_1 (chr15: 78620986-78621045) | Enhancer: neural stem progenitor cell, SK-N-SH cells; ENCODE(ZLab), Ensembl; FANTOM: eRNA score = 40 | | SE_07079 SE_05923 (Brain-Hippocampus middle)SE_07917 (Brain-Inferior temporal lobe)SE_32861 (H1-ESC)SE_05045 (Brain-Cingulate gyrus)SE_68844 (H9) | 5E−06, Brain-Nucleus accumbens (basal ganglia) |
| rs1051730-G/EUR | CHRNA3_1 (chr15: 78620986-78621045) | Enhancer: neural stem progenitor cell, SK-N-SH cells; ENCODE(ZLab), Ensembl; FANTOM: eRNA score = 40 | | SE_07079 SE_05923 (Brain-Hippocampus middle)SE_07917 (Brain-Inferior temporal lobe)SE_32861 (H1-ESC)SE_05045 (Brain-Cingulate gyrus)SE_68844 (H9) | 5E−06, Brain-Nucleus accumbens (basal ganglia) |

TABLE 2B-continued

Part 2. Regulatory elements associated with enhancer and superenhancer
SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| rs1051730-A/EUR | CHRNA3_1 (chr15: 78620986-78621045) | Enhancer: neural stem progenitor cell, SK-N-SH cells; ENCODE(ZLab), Ensembl; FANTOM: eRNA score = 40 | | SE_07079 SE_05923 (Brain-Hippocampus middle)SE_07917 (Brain-Inferior temporal lobe)SE_32861 (H1-ESC)SE_05045 (Brain-Cingulate gyrus)SE_68844 (H9) | 5E−06, Brain-Nucleus accumbens (basal ganglia) |
| rs1051730-G/EUR | CHRNA3_1 (chr15: 78620986-78621045) | Enhancer: neural stem progenitor cell, SK-N-SH cells; ENCODE(ZLab), Ensembl; FANTOM: eRNA score = 40 | | SE_07079 SE_05923 (Brain-Hippocampus middle)SE_07917 (Brain-Inferior temporal lobe)SE_32861 (H1-ESC)SE_05045 (Brain-Cingulate gyrus)SE_68844 (H9) | 5E−06, Brain-Nucleus accumbens (basal ganglia) |
| rs2155646-C/EUR | | Enhancer: H1-hESC, neural stem progenitor cell, Brain (chr11:113059055-113059658 (chr11:113188333-113188936, eRNA Score: 482) ENCODE, Ensembl, FANTOM, Vista | | SE_05136 (Brain-Cingulate gyrus) | 8.2E−111, Brain Cingulate Gyrus |
| rs7938812-T/EUR | | Enhancer: H1-hESC, neural stem progenitor cell | | SE_05136 (Brain-Cingulate gyrus) | 1.1E−17, Brain Cingulate Gyrus |
| rs3130820/ EUR | TRIM28_1 (chr19: 58544407-58544466) TRIM28_2 (chr19: 58544703-58544762) | Enhancer, Astrocytes, bipolar neuron, brain; ENSR00000111889 (chr19:58543000-58546201); ENSR00000594490 (chr19:58546400-58547001) | | SE_33104 (Brain-Cingulate gyrus) | 1E−23; Brain Cingulate Gyrus |
| rs3918226-T/EUR | NOS3_2 (chr7: 150991010-150991069) | Enhancer, Astrocytes, bipolar neuron, brain; ENSR00000843798 (chr7:151007800-151009201); ENSR00000843799 (chr7:151013000-151014601) ENSR00000843800 (chr7:151010400-151011201) | | | 1.1E−07, Brain Cerebellum |
| rs3918226/ EA (Han Chinese) | NOS3_2 (chr7: 150991010-150991069) | Enhancer, Astrocytes, bipolar neuron, brain; ENSR00000843798 (chr7:151007800-151009201); ENSR00000843799 (chr7:151013000-151014601) ENSR00000843800 (chr7:151010400-151011201) | | | 1.1E−07, Brain Cerebellum |
| rs3918226-T/AFR, | NOS3_2 (chr7: | Enhancer, Astrocytes, bipolar neuron, brain; | | | 1.1E−07, Brain |

TABLE 2B-continued

Part 2. Regulatory elements associated with enhancer and superenhancer SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| AMR, ASN, EUR | 150991010-150991069) | ENSR00000843798 (chr7:151007800-151009201); ENSR00000843799 (chr7:151013000-151014601) ENSR00000843800 (chr7:151010400-151011201) | | | Cerebellum |
| rs3918226-T/EUR | NOS3_2 (chr7: 150991010-150991069) | Enhancer, Astrocytes, bipolar neuron, brain; ENSR00000843798 (chr7:151007800-151009201); ENSR00000843799 (chr7:151013000-151014601) ENSR00000843800 (chr7:151010400-151011201) | | | 1.1E−07, Brain Cerebellum |
| rs3918226-T/EUR | NOS3_2 (chr7: 150991010-150991069) | Enhancer, Astrocytes, bipolar neuron, brain; ENSR00000843798 (chr7:151007800-151009201); ENSR00000843799 (chr7:151013000-151014601) ENSR00000843800 (chr7:151010400-151011201) | | | 1.1E−07, Brain Cerebellum |
| rs 2155290/ EUR | | Enhancer: H1-hESC, neural stem progenitor cell, Brain (chr11:113059055-113059658 (chr11:113188333-113188936, eRNA Score: 482) ENCODE, Ensembl, FANTOM, Vista | | SE_05136 (Brain-Cingulate gyrus) | 8.2E−111, Brain Cingulate Gyrus |
| rs182812355-A/ASN | TRIM28_1 (chr19: 58544407-58544466) TRIM28_2 (chr19: 58544703-58544762) | Enhancer, Astrocytes, bipolar neuron, brain; ENSR00000111889 (chr19:58543000-58546201); ENSR00000594490 (chr19:58546400-58547001) | | SE_33104 (Brain-Cingulate gyrus) | 1E−23; Brain Cingulate Gyrus |
| rs3918226-T/EUR | NOS3_2 (chr7: 150991010-150991069) | Enhancer, Astrocytes, bipolar neuron, brain; ENSR00000843798 (chr7:151007800-151009201); ENSR00000843799 (chr7:151013000-151014601) ENSR00000843800 (chr7:151010400-151011201) | | | 1.1E−07, Brain Cerebellum |
| rs12764899/ EUR | BORCS7_1 (chr10: 102854213-102854272) | Enhancer, ENSR00000414241 (chr10:102782600-102782801) | | SE_04641 (Brain-Anterior caudate) SE_06458 (Brain-Hippocampus middle) | 1.1E−19, Brain Hippocampus |
| rs11191424-G/EUR | BORCS7_1 (chr10: 102854213-102854272) | Enhancer, ENSR00000414241 (chr10:102782600-102782801) | | SE_04641 (Brain-Anterior caudate) SE_06458 (Brain- | 1.1E−19, Brain Hippocampus |

TABLE 2B-continued

Part 2. Regulatory elements associated with enhancer and superenhancer SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| | | | | Hippocampus middle) | |
| rs2007044/ ASN | | Enhancer: H1-hESC, neural stem progenitor cell | DE_00452: chr12: 2339802-2367400; Schizophrenia | | 3.0E−15, Brain Cingulate Gyrus |
| rs2159100/ ASN, EUR | | Enhancer: H1-hESC, neural stem progenitor cell | DE_00452: chr12: 2339802-2367400; Schizophrenia | | 3.0E−15, Brain Cingulate Gyrus |
| rs514465-A/EUR | GABRA2_3 (chr4: 46389456-46389515) GABRA2_1 (chr4: 46389970-46390029) GABRA2_2 (chr4: 46390118-46390177) | Enhancer, Bipolar neuron, Brain; GH04J046508: | | | 6E−20; Nerve tibial |
| rs2007044-G/ASN, EUR | | Enhancer: H1-hESC, neural stem progenitor cell | DE_00452: chr12: 2339802-2367400; Schizophrenia | | 3.0E−15, Brain Cingulate Gyrus |
| rs1024582-A/ASN | | Enhancer, Bipolar neuron, Brain | DE_00452: chr12: 2339802-2367400; Schizophrenia | | 3.0E−15, Brain Cingulate Gyrus |
| rs2007044/ EUR | | Enhancer: H1-hESC, neural stem progenitor cell | DE_00452: chr12: 2339802-2367400; Schizophrenia | | 3.0E−15, Brain Cingulate Gyrus |
| rs10774909/ EUR | | Enhancer: H1-hESC, neural stem progenitor cell, SK-N-SH cells; GH12J117579: chr12:118017798-118019205; ENCODE(ZLab), Ensembl; FANTOM: eRNA score = 3 | | | |
| rs2007044/ EUR | | Enhancer: H1-hESC, neural stem progenitor cell | DE_00452: chr12: 2339802-2367400; Schizophrenia | | 3.0E−15, Brain Cingulate Gyrus |
| rs7192140 | GRIN2A_3 (chr16: 10181941-10182000) GRIN2A_2 (chr16: 10182377-10182436) GRIN2A_4 (chr16: 10182692-10182751) GRIN2A_1 (chr16: 10182872-10182931) | Enhancer, Bipolar neuron, H1 neuronal progenitor cells; GH16J010079: chr16:10173268-10175436; ENCODE(ZLab), Ensembl, dbSUPER | | | 1.1E−12, Brain Frontal Cortex |
| rs2239030-A/EUR | | Enhancer, Cingulate Gyrus; GH12J002226: chr12:2335414-2336748; dbSUPER, MASTERMIND | DE_00452: chr12: 2339802-2367400; Schizophrenia | | 7E−25: Brain Cingulate Gyrus |
| rs3918226-T/EA | NOS3_2 (chr7: | Enhancer, Astrocytes, bipolar neuron, brain; | | | 1.1E−07, Brain |

TABLE 2B-continued

Part 2. Regulatory elements associated with enhancer and superenhancer SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| (Han Chinese) | 150991010-150991069 | ENSR00000843798 (chr7:151007800-151009201); ENSR00000843799 (chr7:151013000-151014601) ENSR00000843800 (chr7:151010400-151011201) | | | Cerebellum |
| rs11055991-A/EUR | | | | | |
| rs2007044/ EUR | | Enhancer: H1-hESC, neural stem progenitor cell | DE_00452: chr12: 2339802- 2367400; Schizophrenia | | 3.0E-15, Brain Cingulate Gyrus |
| rs1024582-A/EUR | | Enhancer: H1-hESC, neural stem progenitor cell | DE_00452: chr12: 2339802- 2367400; Schizophrenia | | 5.5E-35, Brain Cingulate Gyrus |
| rs7893279-T/ASN, EUR | | Enhacer, Astrocytes, Bipolar neuron, Brain | | | 2.00E-15; Brain Frontal Cortex |
| rs8042374-A/EA (Han Chinese) | CHRNA3_2 (chr15: 78621269-78621328) | Enhancer: neural stem progenitor cell, SK-N-SH cells; ENCODE(ZLab), Ensembl; FANTOM: eRNA score = 40 | | SE_07079 SE_05923 (Brain-Hippocampus middle)SE_07917 (Brain-Inferior temporal lobe)SE_32861 (H1-ESC)SE_05045 (Brain-Cingulate gyrus)SE_68844 (H9) | 5.5E-35, Brain Cingulate Gryus |
| rs7893279-T/ASN, EUR | | Enhacer, Astrocytes, Bipolar neuron, Brain | | | 2.00E-15; Brain Frontal Cortex |
| rs7893279-T, ASN, EUR | | Enhacer, Astrocytes, Bipolar neuron, Brain | | | 2.00E-15; Brain Frontal Cortex |
| rs1006737/ EUR | | Enhancer, Cingulate Gyrus; GH12J002226: chr12:2335414-2336748; dbSUPER | DE_00452: chr12: 2339802-2367400; Schizophrenia; 23andMe blog rs1006737 or (rs2159100) Each T at this SNP increased the odds of bipolar disorder by 1.9-fold | | 1E-12: Brain Frontal Cortex |
| rs28681284-C/ASN | | Enhancer: neural stem progenitor cell, SK-N-SH cells; ENCODE(ZLab), Ensembl; FANTOM: eRNA score = 40 | | SE_07079 SE_05923 (Brain-Hippocampus middle)SE_07917 (Brain-Inferior temporal lobe)SE_32861 (H1-ESC)SE_05045 (Brain-Cingulate gyrus)SE_68844 (H9) | 5.5E-35, Brain Cingulate Gryus |
| rs7893279-T/ASN, EUR | | Enhacer, Astrocytes, Bipolar neuron, Brain | | | 2.00E-15; Brain Frontal Cortex |
| rs3918226/ EUR | NOS3_2 (chr7: 150991010- | Enhancer, Astrocytes, bipolar neuron, brain; ENSR00000843798 | | | 1.1E-07, Brain Cere- |

TABLE 2B-continued

Part 2. Regulatory elements associated with enhancer and superenhancer SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| | 150991069) | (chr7:151007800-151009201); ENSR00000843799 (chr7:151013000-151014601) ENSR00000843800 (chr7:151010400-151011201) | | | bellum |
| rs7893279-T/ASN (Han Chinese), EUR | | Enhacer, Astrocytes, Bipolar neuron, Brain | | | 2.00E-15; Brain Frontal Cortex |
| rs1006737-A/EUR | | Enhancer, Cingulate Gyrus; GH12J002226; chr12:2335414-2336748; dbSUPER | DE_00452: chr12: 2339802-2367400; Schizophrenia; 23andMe blog rs1006737 or (rs2159100) Each T at this SNP increased the odds of bipolar disorder by 1.9-fold | | 1E-12: Brain Frontal Cortex |
| rs111294930-A/EUR | GRIA1_1 (chr5: 153490621-153490680) | Enhancer, Brain, neural progenitor cell: ENSR00000774341 (chr5:153490200-153492801) Ensemble, ENCODE. FANTOm | | | 1E-25; Brain Cingulate Gyrus |
| rs7688285-C/AFR, EUR | GLRB_1 (chr4: 157076101-157076160) | Enhancer, GLRB, GRIA2, PDGFC, Astrocytes, Brain; ENCODE(ZLab), Ensembl, dbSUPER | | | 1E-22, Amygdala |
| rs641574-A/EUR | GRIA4_1 (chr11: 105610024-105610083) GRIA4_3 (chr11: 105610666-105610725) GRIA4_2 (chr11: 105610842-105610901) | chr11:105609674-105612903 | | SE_05045 (Brain-Cingulate gyrus) | 1E-25; Brain Cingulate Gyrus |
| rs2298527-C/EUR | | Enhancer: H1-hESC, neural stem progenitor cell, Brain (chr11:113059055-113059658 (chr11:113188333-113188936, eRNA Score: 482) ENCODE, Ensembl, FANTOM, Vista | | SE_05136 (Brain-Cingulate gyrus) | 8.2E-111, Brain Cingulate Gyrus |
| rs7192140-C/EUR | GRIN2A_3 (chr16: 10181941-10182000) GRIN2A_2 (chr16: 10182377-10182436) GRIN2A_4 (chr16: 10182692-10182751) GRIN2A_1 (chr16: 10182872-10182931) | Enhancer, Bipolar neuron, H1 neuronal progenitor cells; GH16J010079: chr16:10173268-10175436; ENCODE(ZLab), Ensembl, dbSUPER | | | 1.1E-12, Brain Frontal Cortex |

TABLE 2B-continued

Part 2. Regulatory elements associated with enhancer and superenhancer
SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| rs9292918-G/ASN | HCN1_1 (chr5: 45696271-45696330) | Enhancer, Bipoar Neuron, Brain, neural progenitor cell; ENSR00000754146 (chr5:45453802-45454473, Type: Proximal): ENOCDE, Ensmbl, FANTOM | | SE_05045 (Brain-Cingulate gyrus) | 1E-11; Frontal Cortex |
| rs2155290-C/EUR | | Enhancer: H1-hESC, neural stem progenitor cell, Brain (chr11:113059055-113059658 (chr11:113188333-113188936, eRNA Score: 482) ENCODE, Ensembl, FANTOM, Vista | | SE 05136 (Brain-Cingulate gyrus) | 8.2E-111, Brain Cingulate Gyrus |
| rs16902086/ EUR | HCN1_1 (chr5: 45696271-45696330) | Enhancer, Bipoar Neuron, Brain, neural progenitor cell; ENSR00000754146 (chr5:45453802-45454473, Type: Proximal): ENOCDE, Ensmbl, FANTOM | | SE_05045 (Brain-Cingulate gyrus) | 1E-11; Brain Frontal Cortex |
| rs7893279-T/ASN (Han Chinese), EUR | | Enhacer, Astrocytes, Bipolar neuron, Brain | | | 2.00E-15; Brain Frontal Cortex |
| rs2239030-A/EUR | | Enhancer, Cingulate Gyrus; GH12J002226: chr12:2335414-2336748; dbSUPER | DE_00452: chr12:2339802-2367400; Schizophrenia; 23andMe blog rs1006737 or (rs2159100) Each T at this SNP increased the odds of bipolar disorder by 1.9-fold | | 1E-12: Brain Frontal Cortex |
| rs1837016-T/EUR | NQO1_1 (chr16: 69726550-69726609) NQO1_2 (chr16: 69726912-69726971) | Promoter/Enhancer, Brain, Bipolar neurons, neural progenitor cells, liver; GH16J069721: chr16:69755550-69762759 ;ENCODE(Z-Lab), EPDnew, Ensembl, FANTOM5, dbSUPER; Elite | — | SE_35409 (HepG2) SE_05045 (Brain-Cingulate Gyrus) | — |
| rs111294930-A/ASN, EUR | GRIA1_1 (chr5: 153490621-153490680) | Enhancer, Brain, neural progenitor cell: ENSR00000774341 (chr5:153490200-153492801) Ensemble, ENCODE. FANTOM | | | 1E-25; Brain Cingulate Gyrus |
| rs62367520/ EUR | HCN1_1 (chr5: 45696271-45696330) | Enhancer, Bipoar Neuron, Brain, neural progenitor cell; ENSR00000754146 (chr5:45453802-45454473, Type: Proximal): ENOCDE, Ensmbl, FANTOM | | SE_05045 (Brain-Cingulate gyrus) | 1E-11; Brain Frontal Cortex |
| rs11647445-G/EUR | GRIN2A_3 (chr16: 10181941-10182000) GRIN2A_2 (chr16: 10182377-10182436) | Enhancer, Bipolar neuron, H1 neuronal progenitor cells; GH16J010079: ch16:10173268-10175436; ENCODE(ZLab), Ensmbl, dbSUPER | | | 1.1E-12, Brain Frontal Cortex |

TABLE 2B-continued

Part 2. Regulatory elements associated with enhancer and superenhancer SNPs that have been found in the ketamine adverse event sub-network.

| GWAS SNP Reported/ Population(s) | Promoters (EPDnew); PromID | Enhancers | Validated casual human disease enhancer- promoter pairs | Superenhancers (dbSUPER) | eQTL |
|---|---|---|---|---|---|
| | GRIN2A_4 (chr16: 10182692- 10182751) GRIN2A_1 (chr16: 10182872- 10182931) | | | | |
| rs7893279- T/ASN (Han Chinese), EUR | | Enhacer, Astrocytes, Bipolar neuron, Brain | | | 2.00E−15; Brain Frontal Cortex |
| rs4782271- A/EUR | GRIN2A_3 (chr16: 10181941- 10182000) GRIN2A_2 (chr16: 10182377- 10182436) GRIN2A_4 (chr16: 10182692- 10182751) GRIN2A_1 (chr16: 10182872- 10182931) | Enhancer, Bipolar neuron, H1 neuronal progenitor cells; GH16J010079: chr16:10173268- 10175436; ENCODE(ZLab), Ensembl, dbSUPER | | | 1.1E−12, Brain Frontal Cortex |
| rs7893279- T/EUR | | Enhacer, Astrocytes, Bipolar neuron, Brain | | | 2.00E−15; Brain Frontal Cortex |
| rs73047488/ EUR | GRIN2B_1 (chr12: 13980410- 13980469) GRIN2B_2 (chr12: 13981966- 13982025) | Enhancer, Bipola Neuron, Brain; ENSR00000451168 (chr12:13980400- 13982401) Ensembl, VISTA, FANTOM | | SE_33104 (Brain- Cingulate gyrus) | 3.00E−10; Amy- gala |
| rs3825845- C/ASN | CHRNA3_2 (chr15: 78621269- 78621328) | Enhancer: neural stem progenitor cell, SK-N-SH cells; ENCODE(ZLab), Ensembl; FANTOM: eRNA score = 40 | | SE_07079 SE_05923 (Brain- Hippocampus middle)SE_07917 (Brain-Inferior temporal lobe)SE_32861 (H1- ESC)SE_05045 (Brain-Cingulate gyrus)SE_68844 (H9) | 5.5E−35, Brain Cingulate Gryus |
| rs10744560/ EUR | — | Enhancer, Cingulate Gyrus; GH12J002226: chr12:2335414-2336748; dbSUPER | DE_00452: chr12: 2339802-2367400; Schizophrenia; 23andMe blog rs1006737 or (rs2159100) Each T at this SNP increased the odds of bipolar disorder by 1.9-fold | | 1E−12: Brain Frontal Cortex |
| rs113551349/ EUR | SLC6A9_1 (chr1: 44031452- 44031511) SLC6A9_4 (chr1: 44032187- 44032246) | Enhancer, Brain, H1 neuronal progenitor, H9, H9 neuron progenitor cells, H9 neuron cells; Ensembl: ENSR00000355772 (chr1:44016001- 44017400); MASTERMIND | — | SE_05770 SE_06677 (Brain- Hippocampus middle)SE_08888 (Brain-Mid frontal lobe)SE_03147 (Brain-Angular gyrus)SE_03879 (Brain-Anterior | — |

TABLE 2B-continued

Part 2. Regulatory elements associated with enhancer and superenhancer
SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| | | | | caudate)SE_04765 (Brain-Cingulate gyrus)SE_07718 (Brain-Inferior temporal lobe) | |
| rs2973155-C/EUR | GRIA1_1 (chr5: 153490621-153490680) | Enhancer, Brain, neural progenitor cell: ENSR00000774341 (chr5:153490200-153492801) Ensemble, ENCODE. FANTOM | | | 1E−25; Brain Cingulate Gyrus |
| rs13233131/ EUR | | Enhancer, Bipolar Neuron, Brain; ENSR00000840912 (chr7:136997601-136998801 (Ensembl, Vista0 | | SE_05136 (Brain-Cingulate gyrus) | 1E−32, Brain Cingulate Gyrus |
| rs758117-C/ASN | | Enhancer, Cingulate Gyrus; GH12J002226: chr12:2335414-2336748; dbSUPER | DE_00452: chr12: 2339802-2367400; Schizophrenia; 23andMe blog rs1006737 or (rs2159100) Each T at this SNP increased the odds of bipolar disorder by 1.9-fold | | 1E−12: Brain Frontal Cortex |
| rs872123/ EUR | — | Enhancer, Brain, neural progenitor cells, H1 ESC cells; ENSR00000627779 (chr2:170809001-170814605, Type: Proximal) ENCODE, Z labs | — | — | 1E−05, Brain Aanterior Caudate |
| rs2973155-C/EUR | GRIA1_1 (chr5: 153490621-153490680) | Enhancer, Brain, neural progenitor cell: ENSR00000774341 (chr5:153490200-153492801) Ensemble, ENCODE. FANTOM | | | 1E−25; Brain Cingulate Gyrus |
| rs13176930-T/ASN | GRIA1_1 (chr5: 153490621-153490680) | Enhancer, Brain, neural progenitor cell: ENSR00000774341 (chr5:153490200-153492801) Ensemble, ENCODE. FANTOM | | | 1E−25; Brain Cingulate Gyrus |
| rs9292918/ EUR | HCN1_1 (chr5: 45696271-45696330) | Enhancer, Bipoar Neuron, Brain, neural progenitor cell; ENSR00000754146 (chr5:45453802-45454473, Type: Proximal): ENOCDE, Ensmbl, FANTOM | | SE_05045 (Brain-Cingulate gyrus) | 1E−11; Frontal Cortex |
| rs1478364-T/EUR | GRIA1_1 (chr5: 153490621-153490680) | Enhancer, Brain, neural progenitor cell: ENSR00000774341 (chr5:153490200-153492801) Ensemble, ENCODE. FANTOM | | | 1E−25; Brain Cingulate Gyrus |
| rs9922678 (rs9926303)/ EUR | GRIN2A_3 (chr16: 10181941-10182000) GRIN2A_2 (chr16: 10182377-10182436) GRIN2A_4 (chr16: 10182692- | Enhancer, dorsolateral frontal cortex, atrocytes, bipolar neurons, neural progenitor cells; ENCODE, FANTOM5, Vista. | | | 1.1E−12, Brain Frontal Cortex |

TABLE 2B-continued

Part 2. Regulatory elements associated with enhancer and superenhancer
SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| | 10182751) GRIN2A_1 (chr16: 10182872-10182931) | | | | |
| rs7191183/ EUR | GRIN2A_3 (chr16: 10181941-10182000) GRIN2A_2 (chr16: 10182377-10182436) GRIN2A_4 (chr16: 10182692-10182751) GRIN2A_1 (chr16: 10182872-10182931) | Enhancer, dorsolateral frontal cortex, atrocytes, bipolar neurons, neural progenitor cells; ENCODE, FANTOM5, Vista. | | | 1.1E−12, Brain Frontal Cortex |
| rs9922678-A/ASN, EUR | GRIN2A_3 (chr16: 10181941-10182000) GRIN2A_2 (chr16:Vista. 10182377-10182436) GRIN2A_4 (chr16: 10182692-10182751) GRIN2A_1 (chr16: 10182872-10182931) | Enhancer, dorsolateral frontal cortex, atrocytes, bipolar neurons, neural progenitor cells; ENCODE, FANTOM5, | | | 1.1E−12, Brain Frontal Cortex |
| rs17504622-T/ASN, EUR | GRIN2A_3 (chr16: 10181941-10182000) GRIN2A_2 (chr16: 10182377-10182436) GRIN2A_4 (chr16: 10182692-10182751) GRIN2A_1 (chr16: 10182872-10182931) | Enhancer, dorsolateral frontal cortex, atrocytes, bipolar neurons, neural progenitor cells; ENCODE, FANTOM5, Vista. | | | 1.1E−12, Brain Frontal Cortex |
| rs728022696/ EUR | GRIA1_1 (chr5: 153490621-153490680) | Enhancer, Brain, neural progenitor cell: ENSR00000774341 (chr5:153490200-153492801) Ensemble, ENCODE. FANTOM | | | 1E−25; Brain Cingulate Gyrus |
| rs4765913/ EUR | | Enhancer, Cingulate Gyrus; GH12J002226: chr12:2335414-2336748; dbSUPER | DE_00452: chr12: 2339802-2367400; Schizophrenia; 23andMe blog rs1006737 or (rs2159100) Each T at this SNP increased the odds of bipolar disorder by 1.9-fold | | 1E−12: Brain Frontal Cortex |
| rs9922678/ ASN, EUR | GRIN2A_3 (chr16: 10181941- | Enhancer, dorsolateral frontal cortex, bipolar neurons, neural | | | 1.1E−12, Brain Frontal |

TABLE 2B-continued

Part 2. Regulatory elements associated with enhancer and superenhancer
SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| | 10182000) GRIN2A_2 (chr16: 10182377-10182436) GRIN2A_4 (chr16: 10182692-10182751) GRIN2A_1 (chr16: 10182872-10182931) | progenitor cells; ENCODE, FANTOM5, Vista. | | | Cortex |
| rs13176930/ EUR | GRIA1_1 (chr5: 153490621-153490680) | Enhancer, Brain, neural progenitor cell: ENSR00000774341 (chr5:153490200-153492801) Ensemble, ENCODE. FANTOM | | | 1E−25; Brain Cingulate Gyrus |
| rs117578877-T/EUR | GRIN2B_1 (chr12: 13980410-13980469) GRIN2B_2 (chr12: 13981966-13982025) | Enhancer, Bipola Neuron, Brain; ENSR00000451168 (chr12:13980400-13982401) Ensembl, VISTA, FANTOM | | SE_33104 (Brain-Cingulate gyrus) | 3.00E−10: Brain Cingulate Gyrus |
| rs1501357-C/ASN, EUR | HCN1_1 (chr5: 45696271-45696330) | Enhancer, Bipoar Neuron, Brain, neural progenitor cell; ENSR00000754146 (chr5:45453802-45454473, Type: Proximal): ENOCDE, Ensmbl, FANTOM | | SE_05045 (Brain-Cingulate gyrus) | 1E−11; Frontal Cortex |
| rs4765914/ EUR | | Enhancer, Cingulate Gyrus; GH12J002226: chr12:2335414-2336748; dbSUPER | DE_00452: chr12: 2339802-2367400; Schizophrenia; 23andMe blog rs1006737 or (rs2159100) Each T at this SNP increased the odds of bipolar disorder by 1.9-fold | | 1E−12: Brain Frontal Cortex |
| rs1006737/ EUR | | Enhancer, Cingulate Gyrus; GH12J002226: chr12:2335414-2336748; dbSUPER | DE_00452: chr12: 2339802-2367400; Schizophrenia; 23andMe blog rs1006737 or (rs2159100) Each T at this SNP increased the odds of bipolar disorder by 1.9-fold | | 1E−12: Brain Frontal Cortex |
| rs9922678-A/ASN | GRIN2A_3 (chr16: 10181941-10182000) GRIN2A_2 (chr16: 10182377-10182436) GRIN2A_4 (chr16: 10182692-10182751) GRIN2A_1 (chr16: 10182872-10182931) | Enhancer, dorsolateral frontal cortex, atrocytes, bipolar neurons, neural progenitor cells; ENCODE, FANTOM5, Vista. | | | 1.1E−12, Brain Frontal Cortex |
| rs10744560-T | | Enhancer, Cingulate Gyrus; GH12J002226: chr12:2335414-2336748; | DE_00452: chr12: 2339802-2367400; Schizophrenia; 23andMe | | 1E−12: Brain Frontal |

TABLE 2B-continued

Part 2. Regulatory elements associated with enhancer and superenhancer
SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| | | dbSUPER | blog rs1006737 or (rs2159100) Each T at this SNP increased the odds of bipolar disorder by 1.9-fold | | Cortex |
| rs1501357-C/EUR | HCN1_1 (chr5: 45696271-45696330) | Enhancer, Bipoar Neuron, Brain, neural progenitor cell; ENSR00000754146 (chr5:45453802-45454473, Type: Proximal): ENOCDE, Ensmbl, FANTOM | | SE_05045 (Brain-Cingulate gyrus) | 1E−11; Frontal Cortex |
| rs9922678-A/ASN, EUR | GRIN2A_3 (chr16: 10181941-10182000) GRIN2A_2 (chr16: 10182377-10182436) GRIN2A_4 (chr16: 10182692-10182751) GRIN2A_1 (chr16: 10182872-10182931) | Enhancer, dorsolateral frontal cortex, atrocytes, bipolar neurons, neural progenitor cells; ENCODE, FANTOM5, Vista. | | | 1.1E−12, Brain Frontal Cortex |
| rs68081839/ EUR | GRIA4_1 (chr11: 105610024-105610083) GRIA4_3 (chr11: 105610666-105610725) GRIA4_2 (chr11: 105610842-105610901) | chr11:105609674-105612903 | | SE_05045 (Brain-Cingulate gyrus) | 1E−25; Brain Cingulate Gyrus |
| rs28607014-C/EA (Han Chinese) | | Enhancer: H1-hESC, neural stem progenitor cell, SK-N-SH cells; GH12J117579: chr12:118017798-118019205; ENCODE(ZLab), Ensembl; FANTOM: eRNA score = 3 | | | |
| rs12522290-C/EUR | GRIA1_1 (chr5: 153490621-153490680) | Enhancer, Brain, neural progenitor cell: ENSR00000774341 (chr5:153490200-153492801) Ensemble, ENCODE. FANTOM | | | 1E−25; Brain Cingulate Gyrus |
| rs1006737-A/EUR | | Enhancer, Cingulate Gyrus; GH12J002226: chr12:2335414-2336748; dbSUPER | DE_00452: chr12: 2339802-2367400; Schizophrenia; 23andMe blog rs1006737 or (rs2159100) Each T at this SNP increased the odds of bipolar disorder by 1.9-fold | | 1E−12: Brain Frontal Cortex |
| rs73568641-C/AFR | OPRM1_2 (chr6: 154039211-154039270) OPRM1_3 (chr6: | Enhancer, Bipolar Neurons, Brain; ENSR00000810176 (chr6:154039001-154040001) Ensembl, ENCODE, FANTOM | | SE_03879 (Brain-Anterior caudate | 1E−30: Brain Nucleus Acumbens |

TABLE 2B-continued

Part 2. Regulatory elements associated with enhancer and superenhancer SNPs that have been found in the ketamine adverse event sub-network.

| GWAS SNP Reported/ Population(s) | Promoters (EPDnew); PromID | Enhancers | Validated casual human disease enhancer-promoter pairs | Superenhancers (dbSUPER) | eQTL |
|---|---|---|---|---|---|
| | 154039315-154039374) OPRM1_4 (chr6: 154039500-154039559) | | | | |
| rs13170232-T/EUR | GRIA1_1 (chr5: 153490621-153490680) | Enhancer, Brain, neural progenitor cell: ENSR00000774341 (chr5:153490200-153492801) Ensemble, ENCODE. FANTOM | | | 1E−25; Brain Cingulate Gyrus |
| rs9292918/EUR | HCN1_1 (chr5: 45696271-45696330) | Enhancer, Bipoar Neuron, Brain, neural progenitor cell; ENSR00000754146 (chr5:45453802-45454473, Type: Proximal): ENOCDE, Ensmbl, FANTOM | | SE_05045 (Brain-Cingulate gyrus) | 1E−11; Frontal Cortex |
| rs12522290-C | GRIA1_1 (chr5: 153490621-153490680) | Enhancer, Brain, neural progenitor cell: ENSR00000774341 (chr5:153490200-153492801) Ensemble, ENCODE. FANTOM | | | 1E−25; Brain Cingulate Gyrus |
| rs13008299-G/EUR | WDR43_1 (chr2: 28894641-28894700) | Enahancer, Brain, H1-hESC, H9, neural stem progenitor cell; ENSR00000114662 (chr2:28893601-28897801) Ensembl, ENOCDE, FANTOM, VISTA | | SE_05045 (Brain-Cingulate gyrus) | |
| rs117578877-T/EUR | GRIN2B_1 (chr12: 13980410-13980469) GRIN2B_2 (chr12: 13981966-13982025) | Enhancer, Bipolar Neuron, Brain; ENSR00000451168 (chr12:13980400-13982401) Ensembl, VISTA, FANTOM | | SE_33104 (Brain-Cingulate gyrus) | 3.00E−10; Amygala |
| rs11127199-G/EUR | WDR43_1 (chr2: 28894641-28894700) | Enahancer, Brain, H1-hESC, H9, neural stem progenitor cell; ENSR00000114662 (chr2:28893601-28897801) Ensembl, ENOCDE, FANTOM, VISTA | | SE_05045 (Brain-Cingulate gyrus) | |

TABLE 2B

Part 3. Chromatin interactions for enhancer and superenhancer SNPs that have been found in the ketamine adverse event sub-network.

| GWAS SNP Reported/ Population(s) | Hi-C Score | HGREEN score | Enhancer RNA co-expression p-value | Judged by machine learning to be causal in neural cell lines but not HepG2? |
|---|---|---|---|---|
| rs1051730-A/ ASN, EUR | 1E-27: Nucleus accumbens | 1.00E-15 | 1.00E-50 | Yes |
| rs1051730-G/ EUR | 1E-27: Nucleus accumbens | 1.00E-15 | 1.00E-50 | Yes |
| rs1051730-A/ EUR | 1E-27: Nucleus accumbens | 1.00E-15 | 1.00E-50 | Yes |
| rs1051730-G/ EUR | 1E-27: Nucleus accumbens | 1.00E-15 | 1.00E-50 | Yes |
| rs2155646-C/ EUR | 1E-35: Cingulate cortex | 1.00E-10 | 1.00E-14 | Yes |
| rs7938812-T/ EUR | 1E-35: Cingulate cortex | 1.00E-10 | 1.00E-10 | Yes |
| rs3130820/ EUR | 1E-10: Cingulate cortex | 1.00E-08 | 1.56E-10 | Yes |
| rs3918226-T/ EUR | 1E.00E-20: Cerebellum | 1.00E-08 | | Yes |
| rs3918226/ EA (Han Chinese) | 1E.00E-20: Cerebellum | 1.00E-08 | | Yes |
| rs3918226-T/ AFR, AMR, ASN, EUR | 1E.00E-20: Cerebellum | 1.00E-08 | | Yes |
| rs3918226-T/ EUR | 1E.00E-20: Cerebellum | 1.00E-08 | | Yes |
| rs3918226-T/ EUR | 1E.00E-20: Cerebellum | 1.00E-08 | | Yes |
| rs2155290/ EUR | 1E-35: Cingulate cortex | 1.00E-10 | 1.00E-14 | Yes |
| rs182812355-A/ ASN | 1E-10: Cingulate cortex | 1.00E-08 | 1.56E-10 | Yes |
| rs3918226-T/ EUR | 1E.00E-20: Cerebellum | | | Yes |
| rs12764899/ EUR | 0.00000001: Hippocampus | 1.00E-11 | 5.00E-34 | Yes |
| rs11191424-G/ EUR | 0.00000001: Hippocampus | 1.00E-11 | 5.00E-34 | Yes |
| rs2007044/ ASN | 0.0000000001: Cingulate cortex | 1.00E-15 | 1.30E-89 | Yes |
| rs2159100/ ASN EUR | 0.0000000001: Cingulate cortex | 1.00E-30 | 1.00E-14 | Yes |
| rs514465-A/ EUR | 0.0000000000001: Frontal cortex | 1.00E-15 | | Yes |
| rs2007044-G/ ASN, EUR | 0.0000000001: Cingulate cortex | 1.00E-30 | 1.30E-89 | Yes |
| rs1024582-A/ ASN | 0.0000000001: Cingulate cortex | 1.00E-30 | | Yes |
| rs2007044/ EUR | 0.0000000001: Cingulate cortex | 1.00E-15 | | Yes |
| rs10774909/ EUR | 0.0000001: Frontal cortex | 1.00E-10 | 1.00E-02 | Yes |
| rs2007044/ EUR | 0.0000000001: Cingulate cortex | 1.00E-30 | 1.30E-89 | Yes |
| rs7192140 | 0.0000000000000001: Frontal cortex | 1.00E-20 | 3.00E-12 | Yes |
| rs2239030-A/ EUR | 0.0000000001: Cingulate cortex | 1.00E-15 | 1.00E-03 | Yes |
| rs3918226-T/ EA (Han Chinese) | 1E.00E-20: Cerebellum | 1.00E-08 | | Yes |
| rs11055991-A/ EUR | 0.01: Frontal cortex | 1.00E-12 | | |
| rs2007044/ EUR | 0.0000000001: Cingulate cortex | 1.00E-15 | 1.30E-89 | Yes |
| rs1024582-A/ EUR | 0.0000000001: Cingulate cortex | 1.00E-15 | 1.00E-17 | Yes |

TABLE 2B-continued

Part 3. Chromatin interactions for enhancer and superenhancer SNPs that have been found in the ketamine adverse event sub-network.

| GWAS SNP Reported/ Population(s) | Hi-C Score | HGREEN score | Enhancer RNA co-expression p-value | Judged by machine learning to be causal in neural cell lines but not HepG2? |
|---|---|---|---|---|
| rs7893279-T/ ASN, EUR | 0.0000000001: Frontal cortex | 1.00E−15 | E−08 | Yes |
| rs8042374-A/ EA (Han Chinese) | 1E−27: Cingulate cortex | 1.00E−27 | 1.00E−50 | Yes |
| rs7893279-T/ ASN, EUR | 0.000001; Frontal cortex | 1.00E−05 | E−23 | |
| rs7893279-T, ASN, EUR | 0.000001; Frontal cortex | 1.00E−05 | E−23 | Yes |
| rs1006737/ EUR | 0.0000000001: Cingulate cortex | 1.00E−10 | 1.00E−03 | Yes |
| rs28681284-C/ ASN | 1E−27: Nucleus accumbens | 1.00E−27 | 1.00E−50 | No |
| rs7893279-T/ ASN, EUR | 0.000001; Frontal cortex | 1.00E−15 | 1.00E−08 | Yes |
| rs3918226/ EUR | 1E.00E−20: Cerebellum | 1.00E−08 | | Yes |
| rs7893279-T/ ASN (Han Chinese), EUR | 0.000001: Frontal cortex | 1.00E−15 | E−08 | Yes |
| rs1006737-A/ EUR | 0.0000000001: Cingulate cortex | 1.00E−10 | 1.00E−03 | Yes |
| rs111294930-A/ EUR | 0.000000000001: Cingulate cortex | 1.00E−25 | 1.25E−19 | Yes |
| rs7688285-C/ AFR, EUR | 0.00000000001: Amygdala | | | Yes |
| rs641574-A/ EUR | 0.000000001: Cingulate cortex | 1.00E−41 | 1.25E−27 | Yes |
| rs2298527-C/ EUR | 1E−35: Cingulate cortex | 1.00E−10 | 1.00E−14 | Yes |
| rs7192140-C/ EUR | 0.0000000000000000001: Frontal cortex | 1.00E−20 | 3.00E−12 | Yes |
| rs9292918-G/ ASN | 0.0001: Frontal cortex | 1.00E−05 | | Yes |
| rs2155290-C/ EUR | 1E−35: Cingulate cortex | 1.00E−10 | 1.00E−14 | Yes |
| rs16902086/ EUR | 0.0001: Frontal cortex | 1.00E−05 | | Yes |
| rs7893279-T/ ASN (Han Chinese), EUR | 0.000001: Frontal cortex | 1.00E−15 | 1.00E−08 | |
| rs2239030-A/ EUR | 0.0000000001: Cingulate cortex | 1.00E−20 | 1.00E−03 | Yes |
| rs1837016-T/ EUR | 0.001: Cingulate cortex | — | — | Yes |
| rs111294930-A/ ASN, EUR | 0.000000000001; Cingulate cortex | 1.00E−25 | 1.25E−19 | Yes |
| rs62367520/ EUR | 0.0001: Frontal cortex | 1.00E−05 | | Yes |
| rs11647445-G/ EUR | 0.0000000000000000001: Frontal cortex | 1.00E−20 | 3.00E−12 | Yes |
| rs7893279-T/ ASN (Han Chinese), EUR | 0.000001: Frontal cortex | 1.00E−15 | 1.00E−08 | Yes |
| rs4782271-A/ EUR | 0.0000000000000000001: Frontal cortex | 1.00E−20 | 3.00E−12 | Yes |
| rs7893279-T/ EUR | 1.00E−10 | 1.00E−15 | 1.00E−08 | Yes |
| rs73047488/ EUR | 0.0000000001: Cingulate cortex | 1.00E−15 | 1.00E−33 | Yes |

TABLE 2B-continued

Part 3. Chromatin interactions for enhancer and superenhancer SNPs that have been found in the ketamine adverse event sub-network.

| GWAS SNP Reported/ Population(s) | Hi-C Score | HGREEN score | Enhancer RNA co-expression p-value | Judged by machine learning to be causal in neural cell lines but not HepG2? |
|---|---|---|---|---|
| rs3825845-C/ ASN | 1E−27: Nucleus accumbens | 1.00E−27 | 1.00E−50 | Yes |
| rs10744560/ EUR | 0.0000000001: Frontal cortex | 1.00E−20 | 1.00E−03 | Yes |
| rs113551349/ EUR | 0.0000000000001: Frontal cortex | 2.00E−20 | 1.00E−53 | Yes |
| rs29731 55-C/ EUR | 0.000000000001: Cingulate cortex | 1.00E−25 | 1.25E−19 | Yes |
| rs13233131/ EUR | 0.00001: Cingulate cortex | 1.00E−10 | 5.00E−12 | Yes |
| rs758117-C/ ASN | 0.0000000001: Frontal cortex | 1.00E−20 | 1.00E−03 | Yes |
| rs872123/ EUR | 0.0000000001: Cingulate cortex | 1.00E−10 | 1.2E−15; Tibial nerve | Yes |
| rs29731 55-C/ EUR | 0.000000000001: Cingulate cortex | 1.00E−25 | 1.25E−19 | Yes |
| rs13176930-T/ ASN | 0.000000000001: Cingulate cortex | 1.00E−25 | 1.25E−19 | Yes |
| rs9292918/ EUR | 0.0001: Frontal cortex | 1.00E−05 |  | Yes |
| rs1478364-T/ EUR | 0.000000000001: Cingulate cortex | 1.00E−25 | 1.25E−19 |  |
| rs9922678 (rs9926303)/ EUR | 0.0000000000000001: Frontal cortex | 1.00E−20 | 3.00E−12 | Yes |
| rs7191183/ EUR | 0.0000000000000001: Frontal cortex | 1.00E−20 | 3.00E−12 | Yes |
| rs9922678-A/ ASN, EUR | 0.0000000000000001: Frontal cortex | 1.00E−20 | 3.00E−12 |  |
| rs17504622-T/ ASN, EUR | 0.0000000000000001: Frontal cortex | 1.00E−20 | 3.00E−12 | Yes |
| rs728022696/ EUR | 0.000000000001: Cingulate cortex | 1.00E−25 | 1.25E−19 | Yes |
| rs4765913/ EUR | 0.0000000001: Frontal cortex | 1.00E−20 | 1.00E−03 | Yes |
| rs9922678/ ASN, EUR | 0.0000000000000001: Frontal cortex | 1.00E−20 | 3.00E−12 | Yes |
| rs13176930/ EUR | 0.000000000001: Cingulate cortex | 1.00E−25 | 1.25E−19 | Yes |
| rs117578877-T/ EUR | 0.000000000000000000000000000000000001: Cingulate cortex | 1.00E−15 | 1.00E−33 | Yes |
| rs1501357-C/ ASN, EUR | 0.0001: Frontal cortex | 1.00E−05 |  | Yes |
| rs4765914/ EUR | 0.0000000001: Frontal cortex | 1.00E−20 | 1.00E−03 | Yes |
| rs1006737/ EUR | 0.0000000001: Frontal cortex | 1.00E−10 | 1.00E−03 | Yes |
| rs9922678-A/ ASN | 0.0000000000000001: Frontal cortex | 1.00E−20 | 3.00E−12 | Yes |
| rs10744560-T | 0.0000000001: Frontal cortex | 1.00E−20 | 1.00E−03 | Yes |
| rs1501357-C/ EUR | 0.0001: Frontal cortex | 1.00E−05 | — | Yes |
| rs9922678-A/ ASN, EUR | 0.0000000000000001: Frontal cortex | 1.00E−20 | 3.00E−12 | Yes |
| rs68081839/ EUR | 0.0000000001: Cingulate cortex | 1.00E−41 | 1.25E−27 | Yes |
| rs28607014-C/ EA (Han Chinese) | 0.0000001: Frontal cortex | 1.00E−10 | 1.00E−02 | Yes |
| rs12522290-C/ EUR | 0.000000000001: Cingulate cortex | 1.00E−25 | 1.25E−19 | Yes |
| rs1006737-A/ EUR | 0.0000000001: Frontal cortex | 1.00E−10 | 1.00E−03 | Yes |

TABLE 2B-continued

Part 3. Chromatin interactions for enhancer and superenhancer SNPs that have been found in the ketamine adverse event sub-network.

| GWAS SNP Reported/ Population(s) | Hi-C Score | HGREEN score | Enhancer RNA co-expression p-value | Judged by machine learning to be causal in neural cell lines but not HepG2? |
|---|---|---|---|---|
| rs73568641-C/ AFR | 0.000000000000001: Nucleus accumbens | 1.00E−10 | 1.00E−41 | Yes |
| rs13170232-T/ EUR | 0.000000000001: Cingulate cortex | 1.00E−25 | 1.25E−19 | Yes |
| rs9292918/ EUR | 0.0001: Frontal cortex | 1.00E−05 | | Yes |
| rs12522290-C | 0.000000000001: Cingulate cortex | 1.00E−25 | 1.25E−19 | Yes |
| rs13008299-G/ EUR | 0.0001: Cingulate cortex | | | Yes |
| rs117578877-T/ EUR | 0.0000000001: Amygdala | 1.00E−15 | 1.00E−33 | Yes |
| rs11127199-G/ EUR | 0.0001: Cingulate cortex | | | Yes |

In another embodiment of the methods in this disclosure, generalization of this method may be used to reveal combinations of FDA-approved medications that may be used to enhance therapeutics in neuropsychiatric disorders through their corresponding network or sub-network mechanisms in biology. FIG. 22 illustrates an example of how the valproic acid pharmacogenomic network and the ketamine pharmacogenomic network work in a complementary manner to support neurogenesis. Valproic acid induces the conversion of neural progenitor cells to committed neural progenitors through the npBAF complex (1, top), and ketamine may act on committed neural progenitors through the human silencing complex (HUSH) to turn progenitors into differentiation neurons (1, bottom).

FIG. 23 illustrates how the process shown in FIG. 22 acts through progressive deacetylation of the histone 3 lysine 9 (H3K9) moiety as caused by the valproic pharmacogenomic network (FIG. 23A), and acetylation of the H3K9 moiety following activation of the ketamine pharmacogenomic network (FIG. 23B).

Figure 24:
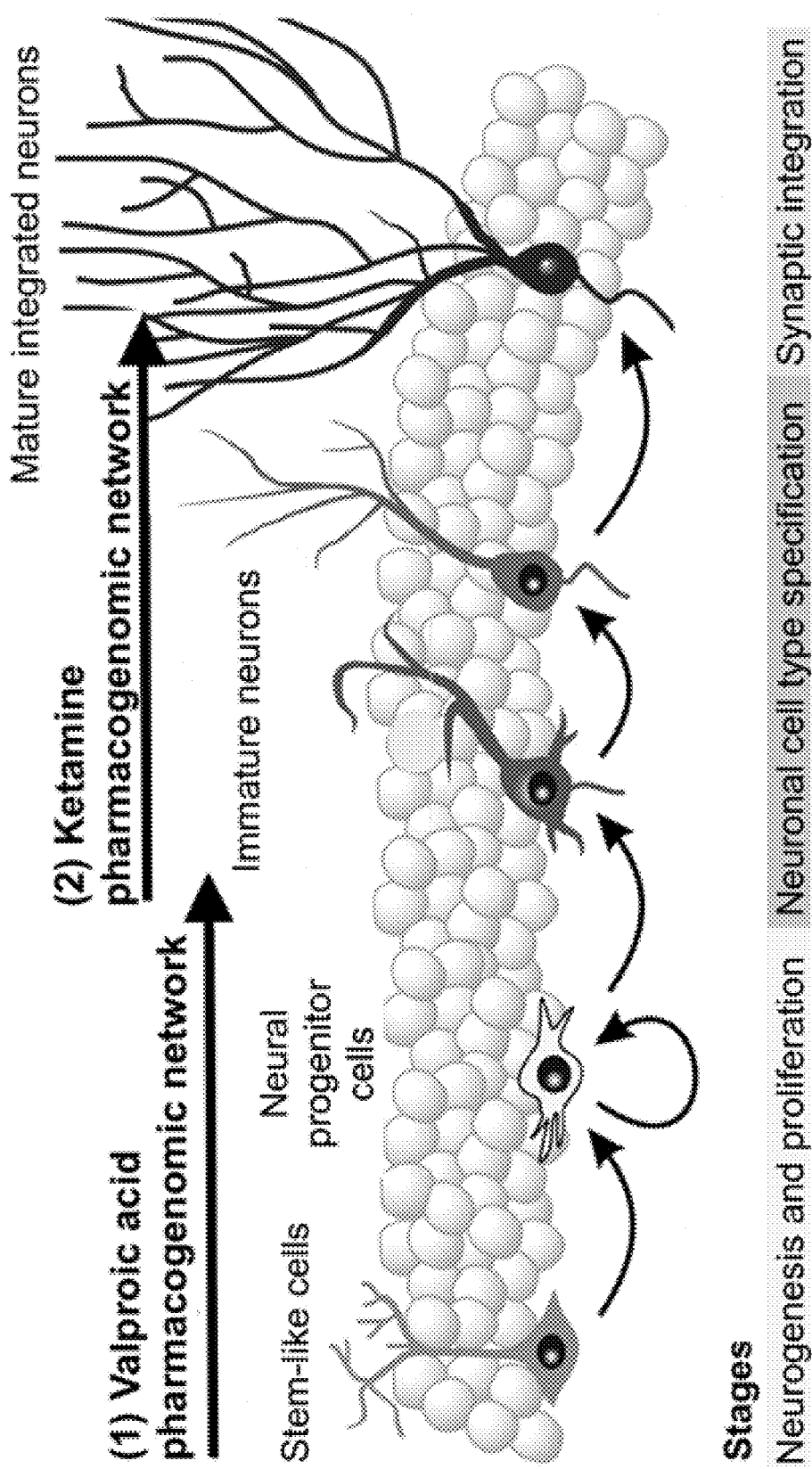
FIG. 24 illustrates the combinatorial and biologically synergistic actions of valproic acid and ketamine pharmacogenomic networks in neurogenesis, neuronal proliferation and terminal neuronal differentiation.

FIG. 24 illustrates how the complementary pharmacogenomic networks of valproic acid and ketamine bring neural progenitors to become mature, differentiated neurons.

In another embodiment of this disclosure, these methods can be used for other antidepressant medications that target the NMDAR network. For example, other NMDAR partial antagonists, including AVP-786 and GLYX-13 (Rapastinel), are in clinical trials as antidepressant medications. Also, blockers of the GLRB on the NMDAR are also under development as antidepressants, including AV101 and D-cycloserine (Seromycin). Selective antagonists of the GRIN2B of the NMDAR are also in development as antidepressants, examples including EVT103, CP101 and MK-0657. Downstream in this pathway is the AMPAR, and several antidepressants are being developed as agonists at GRIA1 and GRIA2 such as ORG 265576.

In another embodiment, these methods can be used for optimization of medication selection for other antidepressants providing greater power than commercially available pharmacogenomic clinical decision support assays that just rely on coding SNPs for classifying patients as to medication. Methods covered by the techniques disclosed herein exploit knowledge of the pharmacogenomic epigenome, including its organization into TADs and TAD-TAD pharmacogenomic connections, which provide enhanced insight into CNS drug mechanisms. In addition, these methods permit objective monitoring of drug-drug interactions and dosing, as well as measurement of parent drugs and their metabolites from serum, as is the case for S-ketamine and its active metabolite nor-ketamine to provide additional insight into individual metabolizer subtypes.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as providing examples only and does not describe every possible embodiment, as describing every possible embodiment would be impractical, if not impossible. One could implement numerous alternate embodiments, using either current technology or technology developed after the filing date of this application.

We claim:

1. A method for treating a patient suffering from neuropsychiatric disorders, the method comprising:
obtaining a biological sample of a patient;
obtaining, from a reference database, a reference drug pharmacogenomic network representation and constituent sub-networks, including at least a reference drug pharmacodynamic efficacy sub-network and a reference drug pharmacodynamic adverse event sub-network, for a glutamate N-methyl-d-aspartate receptor (NMDAR) antagonist or partial antagonist,
wherein a first subset of variants of the reference drug pharmacodynamic adverse event sub-network are causally related to adverse events of the NMDAR antagonist or partial antagonist and a second subset of variants of the reference drug pharmacodynamic efficacy sub-network are causally related to efficacy of the NMDAR antagonist or partial antagonist;
analyzing the biological sample in view of the reference drug pharmacogenomic network representation and the constituent sub-networks using one or more of: targeted single nucleotide polymorphisms (SNP) genotyping, RNA sequencing or expression microarray analysis, chromatin conformation capture, or targeted genotyping based on differential activation and repression of topologically associating domains (TADs) in the biological sample of the patient indicative of drug efficacy and adverse drug events;
determining a patient pharmacogenomic network representation for the NMDAR antagonist or partial antagonist based on the analysis, wherein the patient pharmacogenomic network representation includes a patient drug pharmacodynamic efficacy sub-network and a patient drug pharmacodynamic adverse event sub-network;
determining a similarity score according to at least one of:
a comparison of the patient drug pharmacodynamic efficacy sub-network to the reference drug pharmacodynamic efficacy sub-network, or
a comparison of the patient drug pharmacodynamic adverse event sub-network to the reference drug pharmacodynamic adverse event sub-network;
determining to administer the NMDAR antagonist or partial antagonist to the patient based on the similarity score; and
administering the NMDAR antagonist or partial antagonist to the patient.

2. The method of claim 1, wherein:
the patient pharmacogenomic network representation for the NMDAR antagonist or partial antagonist includes the patient drug pharmacodynamic efficacy sub-network, the patient drug pharmacodynamic adverse event sub-network, a chromatin remodeling sub-network, and a pharmacokinetic enzymes and hormones sub-network, and the constituent sub-networks for the NMDAR antagonist or partial antagonist from the reference database includes the reference drug pharmacodynamic efficacy sub-network, the reference drug pharmacodynamic adverse event sub-network, reference chromatin remodeling sub-networks, and reference pharmacokinetic enzymes and hormones sub-networks spanning human drug response variation, and determining the similarity score includes:
assigning a first score to the patient drug pharmacodynamic efficacy sub-network based on an amount of similarity between the patient drug pharmacodynamic efficacy sub-network and the reference drug pharmacodynamic efficacy sub-network; and
assigning a second score to the patient drug pharmacodynamic adverse event sub-network based on an amount of similarity between the patient drug pharmacodynamic adverse event sub-network and the reference drug pharmacodynamic adverse-event sub-network.

3. The method of claim 2, wherein determining to administer the NMDAR antagonist or partial antagonist to the patient based on the similarity score includes:
determining to administer the NMDAR antagonist or partial antagonist to the patient when the first score is above a first threshold score or the second score is below a second threshold score.

4. The method of claim 3, wherein determining to administer the NMDAR antagonist or partial antagonist to the patient when the first score is above a first threshold score of the second score is below a second threshold score includes:
combining the first and second scores to determine the similarity score; and
determining to administer the NMDAR antagonist or partial antagonist to the patient when the similarity score is above a third threshold score.

5. The method of claim 1, further comprising:
determining a dosage of the NMDAR antagonist or partial antagonist for administering to the patient based on the similarity score; and
administering the determined dosage of the NMDAR antagonist or partial antagonist to the patient.

6. The method of claim 5, wherein determining a dosage of the NMDAR antagonist or partial antagonist for administering to the patient includes:
determining the dosage using a regression model based on a combination of two or more of: the sex of the patient, the age of the patient, whether the patient smokes, ethnicity of the patient, height of the patient, weight of the patient, and mental illness history of the patient.

7. The method of claim 5, further comprising:
obtaining clinical data for the patient;
analyzing data from the biological sample using pharmacometabolomics to determine pre-existing medications and metabolites of the pre-existing medications in the patient; and
determining whether to administer the NMDAR antagonist or partial antagonist to the patient or the dosage based at least in part on drug-gene or drug-drug interactions between the pre-existing medications in the patient and the NMDAR antagonist or partial antagonist.

8. The method of claim 1, wherein the reference drug pharmacogenomic network representation for the NMDAR antagonist or partial antagonist drug obtained from the reference database is a ketamine pharmacogenomic network representation and includes one or more of: Activity regulated cytoskeleton associated protein (ARC) gene, Achaete-Scute family bHLH transcription factor 1 (ASCL1) gene, Brain derived neurotrophic factor (BDNF) gene, BDNF antisense RNA (BDNF-AS) gene, Calcium/calmodulin dependent protein kinase II alpha (CAMK2A) gene, Cyclin dependent kinase inhibitor 1A (CDKN1A) gene, cAMP responsive element modulator (CREM) gene, Cut like homeobox 2 (CUX2) gene, DCC netrin 1 receptor (DCC) gene, Dopamine receptor D2 (DRD2) gene, Fragile X mental retardation 1 (FMR1) gene, Ganglioside induced differentiation associated protein 1 like 1 (GDAP1 L1) gene, Glutamate metabotropic receptor 5 (GRM5) gene, Homer scaffold protein 1 (HOMER1) gene, 5-hydroxytryptamine receptor 1B (HTR1B) gene, 5-hydroxytryptamine receptor 2A (HTR2A) gene, Kruppel like factor 6 (KLF6) gene, Lin-7 homolog C, crumbs cell polarity complex component (LIN7C) long noncoding RNA, LOC105379109 long noncoding RNA, Myocyte enhancer factor 2D (MEF2D) gene, Myosin VI (MYO6) gene, Myelin transcription factor 1 like (MYT1L) gene, Neuronal differentiation 1 (NEUROD1) gene, Neuronal differentiation 2 (NEUROD2) gene, Nescient helix-loop-helix 2 (NHLH2) gene, Neuromedin B (NMB) gene, NMDA receptor synaptonuclear signaling and neuronal migration factor (NSMF) gene, Neurotrophic receptor tyrosine kinase 2 (NTRK2) gene, Phosphatase and tensin homolog (PTEN) gene, Prostaglandin-endoperoxide synthase 2 (PTGS2) gene, Rac family small GTPase 1 (RAC1) gene, Ras protein specific guanine nucleotide releasing factor 2 (RASGRF2) gene, Ras homolog family member A (RHOA) gene, Roundabout guidance receptor 2 (ROBO2) gene, RP11_360A181 long noncoding RNA, Semaphorin 3A (SEMA3A) gene, SH3 and multiple ankyrin repeat domains 1 (SHANK1) gene, SH3 and multiple ankyrin repeat domains 2 (SHANK2) gene, SH3 and multiple ankyrin repeat domains 3 (SHANKS) gene, Solute carrier family 22 member 15 (SLC22A15) gene, Solute carrier family 6 member 2 (SLC6A2) gene, Slit guidance ligand 1 (SLIT1) gene, Slit guidance ligand 2 (SLIT2) gene, Synaptosome associated protein 25 (SNAP25) gene, Synapsin I (SYN1) gene, Synapsin II (SYN2) gene, Synapsin III (SYN3) gene, T-box, brain 1 (TBR1) gene, Transcription factor 4 (TCF4) gene, Acetylcholinesterase (ACHE) gene, Activating transcription factor 7 interacting protein (ATF7IP) gene, Activating transcription factor 7 interacting protein 2 (ATF7IP2) gene, ATPase Na+/K+ Transporting Subunit Alpha 1 (ATP1A1) gene, BLOC-1 related complex unit 7 (BORCS7) gene, Bromodomain containing 4 (BRD4) gene, Calcium voltage-gated channel subunit alpha1 C (CACNA1C) gene, Calcium voltage-gated channel auxiliary subunit beta 1 (CACNB1) gene, Calcium voltage-gated channel auxiliary subunit beta 2 (CACNB2) gene, Calcium voltage-gated channel auxiliary subunit gamma 2 (CACNG2) gene, Cholinergic Receptor Muscarinic 2 (CHRM2) gene, Cholinergic Receptor Nicotinic Alpha 3 Subunit (CHRNA3) gene, Cholinergic Receptor Nicotinic Alpha 5 Subunit (CHRNA5) gene, Cholinergic Receptor Nicotinic Alpha 7 Subunit (CHRNA7) gene, Cannabinoid receptor 1 (CNR1) gene, Disks large homolog 3 (DLG3) gene, Disks large homolog 4 (DLG4) gene, DNA Methyltransferase 1 (DNMT1) gene, Euchromatic histone lysine methyltransferase 1 (EHMT1) gene, Gamma-aminobutyric acid type A receptor alpha2 subunit (GABRA2) gene, Gamma-aminobutyric acid type A receptor alpha5 subunit (GABRA5) gene, Glutamate decarboxylase 1 (GAD1) gene, Glycine receptor alpha 1 (GLRA1) gene, Glycine receptor alpha 2 (GLRA2) gene, Glycine receptor beta (GLRB) gene, Glutamate ionotropic receptor AMPA type subunit 1 (GRIA1) gene, Glutamate ionotropic receptor AMPA type subunit 2 (GRIA2) gene, Glutamate ionotropic receptor AMPA type subunit 4 (GRIA4) gene, Glutamate ionotropic receptor NMDA type subunit 1 (GRIN1) gene, Glutamate ionotropic receptor NMDA type subunit 2A (GRIN2A) gene, Glutamate ionotropic receptor NMDA type subunit 2B (GRIN2B) gene, Glutamate ionotropic receptor NMDA type subunit 2C (GRIN2C) gene, Glutamate ionotropic receptor NMDA type subunit 2D (GRIN2D) gene, Glutamate iono-tropic receptor NMDA type subunit 3A (GRIN3A) gene, Glutamate ionotropic receptor NMDA type subunit 3B (GRIN3B) gene, Hyperpolarization Activated Cyclic Nucleotide Gated Potassium Channel 1 (HCN1) gene, Histone deacetylase 5 (HDAC5) gene, Methyl-CpG binding domain protein 1 (MBD1) gene, M-Phase Phosphoprotein 8 (MPHOSPH8) gene, Neural cell adhesion molecule 1 (NCAM1) gene, Nitric acid synthase 1 (NOS1) gene, Nitric acid synthase 2 (NOS2) gene, Nitric acid synthase 3 (NOS3) gene, NAD(P)H quinone dehydrogenase 1 (NQO1) gene, Opioid receptor kappa 1 (OPRK1) gene, Opioid receptor mu 1 (OPRM1) gene, Roundabout guidance receptor 2 (ROBO2) gene, SET domain bifurcated 1 (SETDB1) gene, SH3 and Multiple Ankyrin Repeat Domains 2 (SHANK2) gene, Sigma Non-Opioid Intracellular Receptor 1 (SIGMAR1) gene, Solute carrier family 6 member 9 (SLC6A9) gene, Transcription Activation Suppressor (TASOR) gene, TOG array regulator of axonemal microtubules 2 (TOGORAM2) gene, Tripartite Motif Containing 28 (TRIM28) gene, Zinc Finger Protein 274 (ZNF274) gene, Anaphase promoting complex subunit 2 (ANAPC2) gene, Cytochrome P450 family 2 subfamily A member 6 (CYP2A6) gene, Cytochrome P450 family 2 subfamily B member 6 (CYP2B6) gene, Cytochrome P450 family 3 subfamily A member 4 (CYP3A4) gene, Eukaryotic Elongation Factor 2 Kinase (EEF2K) gene, Estrogen Receptor 1 (ESR1) gene, or Transcription Elongation Regulator 1 (TCERG1) gene.

9. The method of claim 8, wherein the reference drug pharmacodynamic efficacy sub-network includes one or more of: Activity regulated cytoskeleton associated protein (ARC) gene, Achaete-Scute family bHLH transcription factor 1 (ASCL1) gene, Brain derived neurotrophic factor (BDNF) gene, BDNF antisense RNA (BDNF-AS) gene, Calcium/calmodulin dependent protein kinase II alpha (CAMK2A) gene, Cyclin dependent kinase inhibitor 1A (CDKN1A) gene, cAMP responsive element modulator (CREM) gene, Cut like homeobox 2 (CUX2) gene, DCC netrin 1 receptor (DCC) gene, Dopamine receptor D2 (DRD2) gene, Eukaryotic elongation factor 2 kinase (EEF2K) gene, Fragile X mental retardation 1 (FMR1) gene, Ganglioside induced differentiation associated protein 1 like 1 (GDAP1L1) gene, Glutamate metabotropic receptor 5 (GRM5) gene, Homer scaffold protein 1 (HOMER1) gene, 5-hydroxytryptamine receptor 1B (HTR1B) gene, 5-hydroxytryptamine receptor 2A (HTR2A) gene, Kruppel like factor 6 (KLF6) gene, Lin-7 homolog C, crumbs cell polarity complex component (LIN7C) long noncoding RNA, LOC105379109 long noncoding RNA, Myocyte enhancer factor 2D (MEF2D) gene, Myosin VI (MYO6) gene, Myelin transcription factor 1 like (MYT1L) gene, Neuronal differentiation 1 (NEUROD1) gene, Neuronal differentiation 2 (NEUROD2) gene, Nescient helix-loop-helix 2 (NHLH2) gene, Neuromedin B (NMB) gene, NMDA receptor synaptonuclear signaling and neuronal migration factor (NSMF) gene, Neurotrophic receptor tyrosine kinase 2 (NTRK2) gene, Phosphatase and tensin homolog (PTEN) gene, Prostaglandin-endoperoxide synthase 2 (PTGS2) gene, Rac family small GTPase 1 (RAC1) gene, Ras protein specific guanine nucleotide releasing factor 2 (RASGRF2) gene, Ras homolog family member A (RHOA) gene, Roundabout guidance receptor 2 (ROBO2) gene, RP11_360A181 long noncoding RNA, Semaphorin 3A (SEMA3A) gene, SH3 and multiple ankyrin repeat domains 1 (SHANK1) gene, SH3 and multiple ankyrin repeat domains 2 (SHANK2) gene, SH3 and multiple ankyrin repeat domains 3 (SHANKS) gene, Solute carrier family 22 member 15

(SLC22A15) gene, Solute carrier family 6 member 2 (SLC6A2) gene, Slit guidance ligand 1 (SLIT1) gene, Slit guidance ligand 2 (SLIT2) gene, Synaptosome associated protein 25 (SNAP25) gene, Synapsin I (SYN1) gene, Synapsin II (SYN2) gene, Synapsin III (SYN3) gene, T-box, brain 1 (TBR1) gene, or Transcription factor 4 (TCF4) gene.

10. The method of claim 8, wherein the reference drug pharmacodynamic adverse events sub-network includes one or more of: Acetylcholinesterase (ACHE) gene, Activating transcription factor 7 interacting protein (ATF7IP) gene, Activating transcription factor 7 interacting protein 2 (ATF7IP2) gene, ATPase Na+/K+ Transporting Subunit Alpha 1 (ATP1A1) gene, BLOC-1 related complex unit 7 (BORCS7) gene, Bromodomain containing 4 (BRD4) gene, Calcium voltage-gated channel subunit alpha1 C (CACNA1C) gene, Calcium voltage-gated channel auxiliary subunit beta 1 (CACNB1) gene, Calcium voltage-gated channel auxiliary subunit beta 2 (CACNB2) gene, Calcium voltage-gated channel auxiliary subunit gamma 2 (CACNG2) gene, Cholinergic Receptor Muscarinic 2 (CHRM2) gene, Cholinergic Receptor Nicotinic Alpha 3 Subunit (CHRNA3) gene, Cholinergic Receptor Nicotinic Alpha 5 Subunit (CHRNA5) gene, Cholinergic Receptor Nicotinic Alpha 7 Subunit (CHRNA7) gene, Cannabinoid receptor 1 (CNR1) gene, Disks large homolog 3 (DLG3) gene, Disks large homolog 4 (DLG4) gene, DNA Methyltransferase 1 (DNMT1) gene, Euchromatic histone lysine methyltransferase 1 (EHMT1) gene, Gamma-aminobutyric acid type A receptor alpha2 subunit (GABRA2) gene, Gamma-aminobutyric acid type A receptor alpha5 subunit (GABRA5) gene, Glutamate decarboxylase 1 (GAD1) gene, Glycine receptor alpha 1 (GLRA1) gene, Glycine receptor alpha 2 (GLRA2) gene, Glycine receptor beta (GLRB) gene, Glutamate ionotropic receptor AMPA type subunit 1 (GRIA1) gene, Glutamate ionotropic receptor AMPA type subunit 2 (GRIA2) gene, Glutamate ionotropic receptor AMPA type subunit 4 (GRIA4) gene, Glutamate ionotropic receptor NMDA type subunit 1 (GRIN1) gene, Glutamate ionotropic receptor NMDA type subunit 2A (GRIN2A) gene, Glutamate ionotropic receptor NMDA type subunit 2B (GRIN2B) gene, Glutamate ionotropic receptor NMDA type subunit 2C (GRIN2C) gene, Glutamate ionotropic receptor NMDA type subunit 2D (GRIN2D) gene, Glutamate ionotropic receptor NMDA type subunit 3A (GRIN3A) gene, Glutamate ionotropic receptor NMDA type subunit 3B (GRIN3B) gene, Hyperpolarization Activated Cyclic Nucleotide Gated Potassium Channel 1 (HCN1) gene, Histone deacetylase 5 (HDAC5) gene, Methyl-CpG binding domain protein 1 (MBD1) gene, M-Phase Phosphoprotein 8 (MPHOSPH8) gene, Neural cell adhesion molecule 1 (NCAM1) gene, Nitric acid synthase 1 (NOS1) gene, Nitric acid synthase 2 (NOS2) gene, Nitric acid synthase 3 (NOS3) gene, NAD(P)H quinone dehydrogenase 1 (NQO1) gene, Opioid receptor kappa 1 (OPRK1) gene, Opioid receptor mu 1 (OPRM1) gene, Roundabout guidance receptor 2 (ROBO2) gene, SET domain bifurcated 1 (SETDB1) gene, SH3 and Multiple Ankyrin Repeat Domains 2 (SHANK2) gene, Sigma Non-Opioid Intracellular Receptor 1 (SIGMAR1) gene, Solute carrier family 6 member 9 (SLC6A9) gene, Transcription Activation Suppressor (TASOR) gene, TOG array regulator of axonemal microtubules 2 (TOGORAM2) gene, Tripartite Motif Containing 28 (TRIM28) gene, or Zinc Finger Protein 274 (ZNF274) gene.

11. The method of claim 8, wherein the constituent sub-networks for the ketamine pharmacogenomic network representation include a reference pharmacokinetic enzymes and hormones sub-network, and wherein the reference pharmacokinetic enzymes and hormones sub-network includes one or more of: Anaphase promoting complex subunit 2 (ANAPC2) gene, Cytochrome P450 family 2 subfamily A member 6 (CYP2A6) gene, Cytochrome P450 family 2 subfamily B member 6 (CYP2B6) gene, Cytochrome P450 family 3 subfamily A member 4 (CYP3A4) gene, Disks large homolog 4 (DLG4), Eukaryotic Elongation Factor 2 Kinase (EEF2K) gene, Estrogen Receptor 1 (ESR1) gene, Glutamate ionotropic receptor AMPA type subunit 1 (GRIA1) gene, Glutamate ionotropic receptor AMPA type subunit 4 (GRIA4) gene, Glutamate ionotropic receptor NMDA type subunit 1 (GRIN1) gene, Glutamate ionotropic receptor NMDA type subunit 2B (GRIN2B) gene, Myosin VI (MYO6) gene, Roundabout Guidance Receptor 2 (ROBO2) gene, SH3 and Multiple Ankyrin Repeat Domains 2 (SHANK2) gene, or Transcription Elongation Regulator 1 (TCERG1) gene.

\* \* \* \* \*

UNITED STATES PATENT AND TRADEMARK OFFICE
CERTIFICATE OF CORRECTION

PATENT NO. : 12,176,087 B2
APPLICATION NO. : 16/749737
DATED : December 24, 2024
INVENTOR(S) : Brian D. Athey et al.

Page 1 of 1

It is certified that error appears in the above-identified patent and that said Letters Patent is hereby corrected as shown below:

In the Claims

At Column 128, Line 21, "of" should be -- or --.

At Column 128, Line 56, "drug obtained" should be -- obtained --.

At Column 129, Line 2, "(GDAP1 L1)" should be -- (GDAP1L1) --.

At Column 129, Line 26, "(SHANKS)" should be -- (SHANK3) --.

At Column 130, Line 67, "(SHANKS)" should be -- (SHANK3) --.

Signed and Sealed this
Seventeenth Day of June, 2025

Coke Morgan Stewart
*Acting Director of the United States Patent and Trademark Office*